United States Patent [19]

Sugihara et al.

[11] Patent Number: 4,548,932
[45] Date of Patent: Oct. 22, 1985

[54] 3-AMINO-4-OXO-2,3,4,5-TETRAHYDRO-1,5-BENZOXAZEPINE DERIVATIVES

[75] Inventors: Hirosada Sugihara, Osaka; Kohei Nishikawa, Kyoto; Katsumi Ito, Osaka, all of Japan

[73] Assignee: Takeda Chemical Industries, Ltd., Doshomachi, Japan

[21] Appl. No.: 637,620

[22] Filed: Aug. 3, 1984

[30] Foreign Application Priority Data

Aug. 12, 1983 [WO] PCT Int'l Appl. ... PCT/JP83/00264
Apr. 27, 1984 [WO] PCT Int'l Appl. ... PCT/JP84/00221
Jul. 13, 1984 [WO] PCT Int'l Appl. ... PCT/JP84/00362

[51] Int. Cl.[4] .................. A61K 31/55; C07D 513/04
[52] U.S. Cl. ........................... 514/211; 260/239.3 B; 260/239.3 T
[58] Field of Search ............... 260/239.3 B, 239.3 T; 424/244

[56] References Cited

U.S. PATENT DOCUMENTS 3,341,519  9/1967  Krapcho ............... 260/239.3 B
4,477,464 10/1984  Slade et al. ........... 260/239.3 B

FOREIGN PATENT DOCUMENTS 51391  5/1982  European Pat. Off. ............ 564/193
57998  8/1982  European Pat. Off. ............ 564/193
68173  1/1983  European Pat. Off. ......... 260/239.3 R
58-29779  2/1983  Japan ........................... 260/239.3 B
2103614  2/1983  United Kingdom ......... 260/239.3 B

OTHER PUBLICATIONS

Chemical Abstracts, vol. 94, p. 657, (1981), Registry No. 94:156884t.
Central Patent Index, Basic Abstracts Journal, Section B: FARMDOC, 01015 E/01 B02 TANA 02.05.80, J56156-218, (Mar. 3, 1982).
Central Patent Index, Basic Abstracts Journal, Section B: FARMDOC, 82663 E/39 B02 NIPK 18.02.81, J57136-581, (Nov. 24, 1982).
Central Patent Index, Basic Abstracts Journal, Section B: FARMDOC, 01471J/47 B02 HAMA 13.04.81, J57169-474, (Jan. 26, 1983).

Primary Examiner—Robert T. Bond
Attorney, Agent, or Firm—Wegner & Bretschneider

[57] ABSTRACT

Novel 3-amino-4-oxo-2,3,4,5-tetrahydro-1,5-benzoxazepine derivatives of the formula

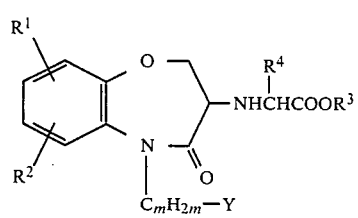

[wherein $R^1$ and $R^2$ are independently hydrogen, halogen, trifluoromethyl, lower alkyl or lower alkoxy, or both jointly form tri- or tetramethylene; $R^3$ is hydrogen, optionally substituted lower alkyl or optionally substituted aralkyl; $R^4$ is hydrogen, optionally substituted alkyl, optionally substituted aralkyl or optionally substituted cycloalkylalkyl; Y is a carboxyl group which may be esterified or amidated; m is 1 or 2] and salts thereof.

These compounds and salts thereof exhibits inhibitory activity on angiotensin converting enzyme and so forth, and are of value as an agent for diagnosis, prevention and treatment of circulatory diseases (e.g. hypertension, cardiopathy, cerebral apoploxy).

19 Claims, No Drawings

3-AMINO-4-OXO-2,3,4,5-TETRAHYDRO-1,5-BENZOXAZEPINE DERIVATIVES

TECHNICAL FIELD

This invention relates to novel 3-amino-4-oxo-2,3,4,5-tetrahydro-1,5-benzoxazepine derivatives useful as pharmaceuticals.

BACKGROUND ART

Several compounds having angiotensin converting enzyme inhibitory activities are known, but compounds having further condensed seven membered ring as a basic moiety are disclosed only in European Patent Publication of Application No. 72352.

The present inventors, after extensive search for compounds which exhibit inhibitory activity on angiotensin converting enzyme and are useful as a therapeutic agent for circulatory diseases (e.g. hypertension, cardiopathy, cerebral apoplexy), succeed in the production of novel 3-amino-4-oxo-2,3,4,5-tetrahydro-1,5-benzoxazepine derivatives having excellent action, and have completed the present invention.

DISCLOSURE OF THE INVENTION

The present invention provides novel compounds represented by the formula:

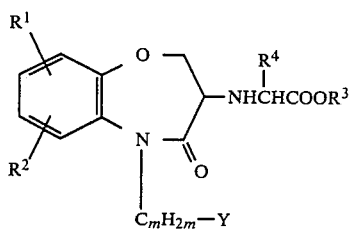

[wherein $R^1$ and $R^2$ are independently hydrogen, halogen, trifluoromethyl, lower alkyl or lower alkoxy, or both jointly form tri- or tetramethylene; $R^3$ is hydrogen, optionally substituted lower alkyl or optionally substituted aralkyl; $R^4$ is hydrogen, optionally substituted alkyl, optionally substituted aralkyl or optionally substituted cycloalkylalkyl; Y is a carboxyl group which may be esterified or amidated; m is 1 or 2] and salts thereof.

Referring to the above formula (I), the halogen represented by $R^1$ or $R^2$ includes, for example, fluorine, chlorine, bromine and iodine, and the lower alkoxy group represented by $R^1$ or $R^2$ includes alkoxy groups containing about 1-4 carbon atoms, such as methoxy, ethoxy, propoxy, isopropoxy, butoxy, isobutoxy, sec-butoxy and tert-butoxy. Also, $R^1$ and $R^2$ may combine with each other to form an alkylene bridge, whose examples include those such as trimethylene and tetramethylene.

The lower alkyl group represented by $R^1$ or $R^2$ includes alkyl groups containing about 1-4 carbon atoms, such as methyl, ethyl, propyl, isopropyl, butyl, isobutyl, sec-butyl and tert-butyl.

The lower alkyl group represented by $R^3$ includes alkyl groups containing about 1-6 carbon atoms, such as methyl, ethyl, propyl, isopropyl, butyl, isobutyl, sec-butyl, tert-butyl, pentyl and hexyl. The said groups may substituted for example by carboxyl, lower-($C_{1-4}$)-alkoxycarbonyl (e.g. methoxycarbonyl, ethoxycarbonyl, propoxycarbonyl, isopropoxycarbonyl, butoxycarbonyl), aryloxycarbonyl (e.g. phenoxycarbonyl) or aralkyloxycarbonyl such as phenyl-lower-($C_{1-4}$)-alkoxycarbonyl (e.g. benzyloxycarbonyl, phenethyloxycarbonyl, 3-phenylpropoxycarbonyl, α-methylbenzyloxycarbonyl, α-ethoxybenzyloxycarbonyl, α-methylphenethyloxycarbonyl, β-methylphenethyloxycarbonyl, β-ethylphenethyloxycarbonyl), wherein the phenyl group in the aryloxycarbonyl and aralkyloxycarbonyl groups may be substituted by 1 to 3 substituents such as halogen (e.g. fluorine, chlorine, bromine, iodine), $C_{1-4}$ alkyl (e.g. methyl, ethyl, propyl, butyl group and the like), $C_{1-4}$ alkoxy (e.g. methoxy, ethoxy, propoxy, isopropoxy, butoxy, methylenedioxy group and the like), amino, nitro or hydroxyl group.

The aralkyl group represented by $R^3$ or $R^4$ includes phenyl-lower-($C_{1-4}$)-alkyl groups, such as benzyl, phenethyl, 3-phenylpropyl, α-methylbenzyl, α-ethylbenzyl, α-methylphenethyl, β-methylphenethyl and β-ethylphenethyl, wherein the phenyl group in said phenyl-lower-alkyl group may be substituted by 1 to 3 substituents such as halogen (e.g. fluorine, chlorine, bromine, iodine), $C_{1-4}$ alkyl group (e.g. methyl, ethyl, propyl, butyl group and the like), $C_{1-4}$ alkoxy group (e.g. methoxy, ethoxy, propoxy, isopropoxy, butoxy), methylenedioxy, amino, nitro or hydroxyl group. Examples of such substituted-phenyl-lower-alkyl groups include 2-(4-chlorophenyl)ethyl, 2-(4-hydroxyphenyl)ethyl, 2-(4-methoxyphenyl)ethyl, 2-(3,4-dimethoxyphenyl)ethyl, 2-(3,4,5-trimethoxyphenyl)ethyl, 2-(3,4-methylenedioxyphenyl)ethyl, 2-(p-tolyl)ethyl, 3,4-dimethoxybenzyl, 3,4-methylenedioxybenzyl, 3,4,5-trimethoxybenzyl, 4-ethylbenzyl, 4-chlorobenzyl.

The alkyl group represented by $R^4$ includes straight chain or branched chain alkyl groups containing about 1–16 carbon atoms (e.g. methyl, ethyl, propyl, isopropyl, butyl, pentyl, isopentyl, 1-ethylpropyl, hexyl, heptyl, octyl, nonyl, decyl, undecyl, dodecyl, tridecyl, tetradecyl, pentadecyl, hexadecyl, 3-ethylpentyl, 4-propylhexyl, 2,2-dimethylbutyl, 3,3-dimethylbutyl, 2,3-dimethylbutyl, 2,2-dimethylhexyl, 3,3-dimethylhexyl), which may have as substituent moiety substituent groups such as hydroxy, lower-($C_{1-4}$)-alkoxy (e.g. methoxy, ethoxy, propoxy, butoxy), mercapto, lower-($C_{1-4}$)-alkylthio (e.g. methylthio, ethylthio, propylthio, butylthio), amino, mono- or di-lower-($C_{1-4}$)-alkylamino (e.g. methylamino, ethylamino, propylamino, isopropylamino, butylamino, isobutylamino, dimethylamino, methylethylamino, methylpropylamino, methylbutylamino, diethylamino, ethylpropylamino, ethylbutylamino, dipropylamino, propylbutylamino, dibutylamino), acylamino such as alkanoylamino containing not more than 5 carbon atoms (e.g. formamido, acetamido, propionamido, butyramido, valeramido, pyvalamido), benzamido, phenyl-lower-($C_{1-4}$)-alkoxycarbonylamino (e.g. benzyloxycarbonylamino) and lower-($C_{1-4}$)-alkoxycarbonylamino (e.g. tert-butoxycarbonylamino), $C_{3-8}$ cycloalkylamino (e.g. cyclopropylamino, cyclobutylamino, cyclopentylamino, cyclohexylamino, cycloheptylamino, cyclooctylamino) or a hetero-alicyclic group. The heteroalicyclic group includes for example condensed or non-condensed hetero-alicyclic groups containing at least one atom of N, O and S as a ring-forming atom, and preferably hetero-mono- or bialicyclic group having a ring or rings composed by 4 to 8 members, the said group being saturated or partially saturated. The said hetero-alicyclic group may contains two or more hetero atoms which are the same kind or two or more kinds. The hetero-alicyclic group includes, for example, oxetanyl, thietanyl, azetidinyl, tetrahydrofuryl, tetrahydrothienyl, pyrrolidinyl, oxanyl (3,4,5,6-tetrahydro-2H-pyranyl), thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiadinyl, oxathianyl, perhydrodiazepinyl, oxathiepanyl, dioxepanyl, dithiepanyl, perhydroxazepinyl, perhydrothiazepinyl, perhydroxazocinyl, perhydrothiazocinyl, oxathiocanyl, perhydrodiazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydrobenzo[b]thienyl, 1,3-dihydrobenzo[c]thienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiazinyl, 2,3-dihydro-1,4-benzoxathienyl, 3,4-dihydro-2H-1,5-benzodioxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydroisoquinolyl, perhydro-1-thianaphthyl and perhydro-2-thianaphthyl.

The said condensed or non-condensed hetero-alicyclic group may have at any substitutive position thereof a substituent or substituents such as oxo, acyl such as lower-($C_{1-5}$)-alkanoyl (e.g. acetyl, propionyl), benzoyl, phenyl-lower-($C_{1-4}$)-alkoxycarbonyl (e.g. benzyloxycarbonyl) or lower-($C_{1-4}$)-alkoxycarbonyl (e.g. tert-butoxycarbonyl), lower-($C_{1-4}$)-alkyl (e.g. methyl, ethyl, propyl, butyl), aryl (e.g. phenyl, naphthyl) and phenyl-lower-($C_{1-4}$)-alkyl (e.g. benzyl, phenethyl, α-methylphenethyl, β-methylphenethyl). The phenyl group in the said aryl or phenyl-lower alkyl group may optionally substituted by halogen (e.g. fluorine, chlorine, bromine), lower-($C_{1-4}$)-alkoxy (e.g. methoxy, ethoxy, propoxy, butoxy) or lower-($C_{1-4}$)-alkyl (e.g. methyl, ethyl, propyl, butyl). The substituted condensed or non-condensed hetero-alicyclic group include, for example, 1-phenylpiperidyl, 1-benzylpiperidyl, 4-phenylpiperidyl, 4-benzylpiperidyl, 1-acetylpiperidyl, 1-benzoylpiperidyl, 4-phenylpiperazinyl, 4-acetylpiperazinyl, 4-benzoylpiperazinyl, 1-oxoisoindolynyl, 1,3-dioxoisoindolynyl, 1,2,3,4-tetrahydro-1-oxoisoquinolyl and 1,2,3,4-tetrahydro-3-oxoisoquinolyl.

When $R^4$ is a substituted alkyl group, the alkyl moiety containing about 2 to 9 carbon atoms is preferable.

The cycloalkylalkyl group represented by $R^4$ includes $C_{3-8}$ cycloalkyl-lower-($C_{1-4}$)-alkyl groups such as cyclopropylethyl, cyclobutylethyl, cyclopentylmethyl, cyclopentylethyl, cyclohexylmethyl, cyclohexylethyl, cyclohexylpropyl, cyclohexylbutyl, cycloheptylethyl and cyclooctylethyl; bicycloalkyl-lower-($C_{1-4}$)-alkyl groups, the bicycloalkyl moiety thereof being exemplified by for example norbornyl, bicyclo[2,2,2]octyl, bicyclo[3,3,1]nonyl or bicyclo[3,3,0]octyl; tricycloalkyl-lower-($C_{1-4}$)-alkyl groups, the tricycloalkyl moiety thereof being exemplified by for example adamantyl. Examples of the bicycloalkyl-lower-alkyl and tricycloalkyl-lower-alkyl groups include norbornylethyl, bicyclo[2,2,2]octylmethyl, bicyclo[3,3,1]nonylpropyl, bicyclo[3,3,0]octylbutyl, adamantylethyl, and the like. The cycloalkyl, bicycloalkyl, tricycloalkyl and lower alkyl groups in said $C_{3-8}$ cycloalkyl-lower-alkyl, bicycloalkyl-lower-alkyl and tricycloalkyl-lower-alkyl groups may be substituted by halogen, $C_{1-4}$ alkyl, $C_{1-4}$ alkoxy, methylenedioxy, amino, nitro or hydroxy.

The esterified carboxyl group represented by Y includes lower-($C_{1-4}$)-alkoxycarbonyl groups, such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl, and phenyl-lower-($C_{1-4}$)-alkoxycarbonyl groups, such as benzyloxycarbonyl, α-phenethyloxycarbonyl, β-phenethyloxycarbonyl, phenylpropoxycarbonyl and phenylbutoxycarbonyl; the amidated carboxyl group includes carboxyl groups amidated with α-amino acids such as glycine, valine, leucine, isoleucine, threonine, $N^α$-lysine, methionine, phenylalanine and tryptophan, wherein the hydrogen atom of the carboxyl group in these α-amino acids may be substituted with lower-($C_{1-4}$)-alkyl (e.g. methyl, ethyl, propyl, butyl, tert-butyl) or phenyl-lower-($C_{1-4}$)-alkyl (e.g. benzyl, phenethyl, phenylpropyl, phenylbutyl).

The group represented by $C_mH_{2m}$ includes methylene ($-CH_2-$) ethylene ($-CH_2CH_2-$) or ethylidene

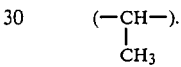

The compounds of the present invention are specifically disclosed in the following:

3(S)-[1-Ethoxycarbonyl-3-phenylpropyl]amino-4-oxo-2,3,4,5-tetrahydro-1,5-benzoxazepine-5-acetic acid and its benzyl ester, 3(S)-[1-Ethoxycarbonyl-3-cyclohexylpropyl]amino-4-oxo-2,3,4,5-tetrahydro-1,5-benzoxazepine-5-acetic acid and its benzyl ester, 3(S)-[1-Ethoxycarbonyl-3-(p-tolyl)propyl]amino-4-oxo-2,3,4,5-tetrahydro-1,5-benzoxazepine-5-acetic acid and its benzyl ester, 3(S)-[1-Isobutoxycarbonyl-3-phenylpropyl]amino-4-oxo-2,3,4,5-tetrahydro-1,5-benzoxazepine-5-acetic acid and its benzyl ester, 7-Chloro-3(S)-[1-ethoxycarbonyl-3-phenylpropyl]amino-4-oxo-2,3,4,5-tetrahydro-1,5-benzoxazepine-5-acetic acid and its benzyl ester, 3(S)-[1-Ethoxycarbonyl-3-phenylpropyl]amino-7-methoxy-4-oxo-2,3,4,5-tetrahydro-1,5-benzoxazepine-5-acetic acid and its benzyl ester, 3(S)-[1-Ethoxycarbonyl-3-phenylpropyl]amino-7-methyl-4-oxo-2,3,4,5-tetrahydro-1,5-benzoxazepine-5-acetic acid and its benzyl ester, 3(S)-[1-Ethoxycarbonyl-3-phenylpropyl]amino-4-oxo-7-trifluoromethyl-2,3,4,5-tetrahydro-1,5-benzoxazepine-5-acetic acid and its benzyl ester, 3(S)-[1-Ethoxycarbonyl-3-phenylpropyl]amino-4-oxo-2,3,4,5,8,9-hexahydro-7H-indeno[5,6-b][1,5]oxazepine-5-acetic acid and its benzyl ester, 3(S)-Ethoxycarbonylmethylamino-4-oxo-2,3,4,5-tetrahydro-1,5-benzoxazepine-5-acetic acid and its benzyl ester, 3(S)-[1-Benzyloxycarbonyl-3-phenylpropyl]amino-4-oxo-2,3,4,5-tetrahydro-1,5-benzoxazepine-5-acetic acid and its benzyl ester, 3(S)-[1-Ethoxycarbonyl-4-methylpentyl]amino-4-oxo-2,3,4,5-tetrahydro-1,5-benzoxazepine-5-acetic acid and its benzyl ester, 3(S)-[1-Ethoxycarbonylnonyl]amino-4-oxo-2,3,4,5-tetrahydro-1,5-benzoxazepine-5-acetic acid and its benzyl ester, 3(S)-[1-Ethoxycarbonyl-3-phenylpropyl]amino-4-oxo-2,3,4,5-tetrahydro-1,5-benzoxazepin-5-yl-N-acetyl-L-phenylalanine and its tert-butyl ester, 3(S)-[1-Ethoxycarbonyl-3-phenylpropyl]amino-4-oxo-2,3,4,5-tetrahydro-1,5-benzoxazepine-5-propionic acid, 3(S)-[1-Ethoxycarbonyl-3-phenylpropyl]amino-4-oxo-2,3,4,5,7,8,9,10-octahydronaphtho[2,3-b][1,5]oxazepine-5-acetic acid and its benzyl ester, 3(S)-[1-Ethoxycarbonyl-3-cyclohexylpropyl]amino-4-oxo-2,3,4,5-tetrahydro-1,5-benzoxazepine-5-α-methylacetic acid, 3(S)-[1-Ethoxycarbonylethyl]amino-4-oxo-2,3,4,5-tetrahydro-1,5-benzoxazepine-5-acetic aicd and its benzyl ester, 3(S)-[1-Ethoxycarbonyl-4-ethylhexyl]amino-4-oxo-2,3,4,5-tetrahydro-1,5-benzoxazepine-5-acetic acid and its benzyl ester, 3(S)-[3-Cycloheptyl-1-ethoxycarbonylpropyl]amino-4-oxo-2,3,4,5-tetrahydro-1,5-benzoxazepine-5-acetic acid and its benzyl ester, 3(S)-[1-Carboxy-3-phenylpropyl]amino-4-oxo-2,3,4,5-tetrahydro-1,5-benzoxazepine-5-acetic acid, 3(S)-[1-Ethoxycarbonyl-3-(3,4,5,6-tetrahydro-2H-pyran-4-yl)propyl]amino-4-oxo-2,3,4,5-tetrahydro-1,5-benzoxazepine-5-acetic aic acid and its benzyl ester, 3(S)-[1-Ethoxycarbonyl-3-(4-thianyl)propyl]amino-4-oxo-2,3,4,5-tetrahydro-1,5-benzoxazepine-5-acetic aicd and its benzyl ester, Benzyl 3(S)-[3-(1-benzyloxycarbonyl-4-piperidyl)-1-ethoxycarbonylpropyl]amino-4-oxo-2,3,4,5-tetrahydro-1,5-benzoxazepine-5-acetate, 3(S)-[1-Ethoxycarbonyl-3-(4-piperidyl)propyl]amino-4-oxo-2,3,4,5-tetrahydro-1,5-benzoxazepine-5-acetic acid, tert-Butyl 3(S)-[3-cyclohexyl-1-ethoxycarbonylpropyl]amino-4-oxo-2,3,4,5-tetrahydro-1,5-benzoxazepine-5-acetate, tert-Butyl 3(S)-[1-carboxy-3-cyclohexylpropyl]amino-4-oxo-2,3,4,5-tetrahydro-1,5-benzoxazepine-5-acetate, 3(S)-[1-Benzyloxycarbonyl-3-cyclohexylpropyl]amino-4-oxo-2,3,4,5-tetrahydro-1,5-benzoxazepine-5-acetic acid and its tert-butyl ester, 3(S)-[3-cyclohexyl-1-ethoxycarbonylmethoxycarbonylpropyl]amino-4-oxo-2,3,4,5-tetrahydro-1,5-benzoxazepine-5-acetic acid and its tert-butyl ester, 3(S)-[1-Butoxycarbonyl-3-cyclohexylpropyl]amino-4-oxo-2,3,4,5-tetrahydro-1,5-benzoxazepine-5-acetic acid and its tert-butyl ester, 3(S)-[1-Carboxy-3-cyclohexylpropyl]amino-4-oxo-2,3,4,5-tetrahydro-1,5-benzoxazepine-5-acetic acid, 3(S)-[1-Carboxy-3-(3,4,5,6-tetrahydro-2H-pyran-4-yl)propyl]amino-4-oxo-2,3,4,5-tetrahydro-1,5-benzoxazepine-5-acetic acid, 3(S)-[1-Carboxy-3-(4-piperidyl)propyl]amino-4-oxo-2,3,4,5-tetrahydro-1,5-benzoxazepine-5-acetic acid, 3(S)-[1-Carboxy-3-(4-thianyl)propyl]amino-4-oxo-2,3,4,5-tetrahydro-1,5-benzoxazepine-5-acetic acid, 3(S)-[1-Ethoxycarbonyl-5-phthalimidopentyl]amino-4-oxo-2,3,4,5-tetrahydro-1,5-benzoxazepine-5-acetic acid and its benzyl ester, 3(S)-[1-Ethoxycarbonyl-7-phthalimidoheptyl]amino-4-oxo-2,3,4,5-tetrahydro-1,5-benzoxazepine-5-acetic acid and its tert-butyl ester, 3(S)-[7-Amino-1-ethoxycarbonylheptyl]amino-4-oxo-2,3,4,5-tetrahydro-1,5-benzoxazepine-5-acetic acid, 3(S)-[7-Amino-1-carboxyheptyl]amino-4-oxo-2,3,4,5-tetrahydro-1,5-benzoxazepine-5-acetic acid, 3(S)-[7-tert-Butoxycarbonylamino-1-ethoxycarbonylheptyl]amino-4-oxo-2,3,4,5-tetrahydro-1,5-benzoxazepine-5-acetic acid and its tert-butyl ester, 3(S)-[1-Ethoxycarbonyl-3-phthalimidopropyl]amino-4-oxo-2,3,4,5-tetrahydro-1,5-benzoxazepine-5-acetic acid, 3(S)-[3-Amino-1-ethoxycarbonylpropyl]amino-4-oxo-2,3,4,5-tetrahydro-1,5-benzoxazepine-5-acetic acid, 3(S)-[3-Amino-1-carboxypropyl]amino-4-oxo-2,3,4,5-tetrahydro-1,5-benzoxazepine-5-acetic acid, 3(S)-[1-Ethoxycarbonyl-4-phthalimidobutyl]amino-4-oxo-2,3,4,5-tetrahydro-1,5-benzoxazepine-5-acetic acid, 3(S)-[4-Amino-1-ethoxycarbonylbutyl]amino-4-oxo-2,3,4,5-tetrahydro-1,5-benzoxazepine-5-acetic acid, 3(S)-[4-Amino-1-carboxybutyl]amino-4-oxo-2,3,4,5-tetrahydro-1,5-benzoxazepine-5-acetic acid, 3(S)-[5-Amino-1-ethoxycarbonylpentyl]amino-4-oxo-2,3,4,5-tetrahydro-1,5-benzoxazepine-5-acetic acid, 3(S)-[5-Amino-1-carboxypentyl]amino-4-oxo-2,3,4,5-tetrahydro-1,5-benzoxazepine-5-acetic acid, 3(S)-[1-Ethoxycarbonyl-6-phthalimidohexyl]amino-4-oxo-2,3,4,5-tetrahydro-1,5-benzoxazepine-5-acetic acid, 3(S)-[6-Amino-1-ethoxycarbonylhexyl]amino-4-oxo-2,3,4,5-tetrahydro-1,5-benzoxazepine-5-acetic acid, 3(S)-[6-Amino-1-carboxyhexyl]amino-4-oxo-2,3,4,5-tetrahydro-1,5-benzoxazepine-5-acetic acid, 3(S)-[1-Ethoxycarbonyl-8-phthalimidooctyl]amino-4-oxo-2,3,4,5-tetrahydro-1,5-benzoxazepine-5-acetic acid, 3(S)-[8-Amino-1-ethoxycarbonyloctyl]amino-4-oxo-2,3,4,5-tetrahydro-1,5-benzoxazepine-5-acetic acid, 3(S)-[8-Amino-1-carboxyoctyl]amino-4-oxo-2,3,4,5-tetrahydro-1,5-benzoxazepine-5-acetic acid, 3(S)-[1-Ethoxycarbonyl-9-phthalimidononyl]amino-4-oxo-2,3,4,5-tetrahydro-1,5-benzoxazepine-5-acetic acid, 3(S)-[9-Amino-1-ethoxycarbonylnonyl]amino-4-oxo-2,3,4,5-tetrahydro-1,5-benzoxazepine-5-acetic acid, 3(S)-[9-Amino-1-carboxynonyl]amino-4-oxo-2,3,4,5-tetrahydro-1,5-benzoxazepine-5-acetic acid, 3(S)-[1-Ethoxycarbonyl-10-phthalimidodecyl]amino-4-oxo-2,3,4,5-tetrahydro-1,5-benzoxazepine-5-acetic acid, 3(S)-[10-Amino-1-ethoxycarbonyldecyl]amino-4-oxo-2,3,4,5-tetrahydro-1,5-benzoxazepine-5-acetic acid, 3(S)-[10-Amino-1-carboxydecyl]amino-4-oxo-2,3,4,5-tetrahydro-1,5-benzoxazepine-5-acetic acid, 3(S)-[1-Ethoxycarbonyl-2-(4-piperidyl)ethyl]amino-4-oxo-2,3,4,5-tetrahydro-1,5-benzoxazepine-5-acetic acid, 3(S)-[1-Carboxy-2-(4-piperidyl)ethyl]amino-4-oxo-2,3,4,5-tetrahydro-1,5-benzoxazepine-5-acetic acid, 3(S)-[1-Ethoxycarbonyl-4-(4-piperidyl)butyl]amino-4-oxo-2,3,4,5-tetrahydro-1,5-benzoxazepine-5-acetic acid, 3(S)-[1-carboxy-4-(4-piperidyl)butyl]amino-4-oxo-2,3,4,5-tetrahydro-1,5-benzoxazepine-5-acetic acid, 3(S)-[1-Ethoxycarbonyl-5-(4-piperidyl)pentyl]amino-4-oxo-2,3,4,5-tetrahydro-1,5-benzoxazepine-5-acetic acid, 3(S)-[1-Carboxy-5-(4-piperidyl)pentyl]amino-4-oxo-2,3,4,5-tetrahydro-1,5-benzoxazepine-5-acetic acid, 3(S)-[1-Ethoxycarbonyl-6-(4-piperidyl)hexyl]amino-4-oxo-2,3,4,5-tetrahydro-1,5-benzoxazepine-5-acetic acid, 3(S)-[1-Carboxy-6-(4-piperidyl)hexyl]amino-4-oxo-2,3,4,5-tetrahydro-1,5-benzoxazepine-5-acetic acid, 3(S)-[1-Ethoxycarbonyl-7-(4-piperidyl)heptyl]amino-4-oxo-2,3,4,5-tetrahydro-1,5-benzoxazepine-5-acetic acid, 3(S)-[1-Carboxy-7-(4-piperidyl)heptyl]amino-4-oxo-2,3,4,5-tetrahydro-1,5-benzoxazepine-5-acetic acid, 3(S)-[1-Ethoxycarbonyl-8-(4-piperidyl)octyl]amino-4-oxo-2,3,4,5-tetrahydro-1,5-benzoxazepine-5-acetic acid, 3(S)-[1-Carboxy-8-(4-piperidyl)octyl]amino-4-oxo-2,3,4,5-tetrahydro-1,5-benzoxazepine-5-acetic acid, 3(S)-[1-Carboxy-7-ethylaminoheptyl]amino-4-oxo-2,3,4,5-tetrahydro-1,5-benzoxazepine-5-acetic acid, 3(S)-[1-Carboxy-7-isopropylaminoheptyl]amino-4-oxo-2,3,4,5-tetrahydro-1,5-benzoxazepine-5-acetic acid, 3(S)-[1-Carboxy-7-dimethylaminoheptyl]amino-4-oxo-2,3,4,5-tetrahydro-1,5-benzoxazepine-5-acetic acid, 3(S)-[1-Carboxy-5-diethylaminopentyl]amino-4-oxo-2,3,4,5-tetrahydro-1,5-benzoxazepine-5-acetic acid, 3(S)-[1-Carboxy-5-dipropylaminopentyl]amino-4-oxo-2,3,4,5-tetrahydro-1,5-benzoxazepine-5-acetic acid, 3(S)-[1-Carboxy-5-dibutylaminopentyl]amino-4-oxo-2,3,4,5-tetrahydro-1,5-benzoxazepine-5-acetic acid, 3(S)-[7-Acetamido-1-carboxyheptyl]amino-4-oxo-2,3,4,5-tetrahydro-1,5-benzoxazepine-5-acetic acid, 3(S)-[7-Benzamido-1-carboxyheptyl]amino-4-oxo-2,3,4,5-tetrahydro-1,5-benzoxazepine-5-acetic acid, 3(S)-[1-Carboxy-5-cyclopentylaminopentyl]amino-4-oxo-2,3,4,5-tetrahydro-1,5-benzoxazepine-5-acetic acid, 3(S)-[1-Carboxy-5-cyclohexylaminopentyl]amino-4-oxo-2,3,4,5-tetrahydro-1,5-benzoxazepine-5-acetic acid, 3(S)-[1-Carboxy-7-cyclohexylaminoheptyl]amino-4-oxo-2,3,4,5-tetrahydro-1,5-benzoxazepine-5-acetic acid, 3(S)-[1-Carboxy-7-dibutylaminoheptyl]amino-4-oxo-2,3,4,5-tetrahydro-1,5-benzoxazepine-5-acetic acid, 3(S)-[5-(1-Acetyl-4-piperidyl)-1-ethoxycarbonylpentyl]amino-4-oxo-2,3,4,5-tetrahydro-1,5-benzoxazepine-5-acetic acid, 3(S)-[5-(1-Benzoyl-4-piperidyl)-1-ethoxycarbonylpentyl]amino-4-oxo-2,3,4,5-tetrahydro-1,5-benzoxazepine-5-acetic acid, 3(S)-[5-(1-Benzyl-4-piperidyl)-1-ethoxycarbonylpentyl]amino-4-oxo-2,3,4,5-tetrahydro-1,5-benzoxazepine-5-acetic acid, 3(S)-[1-Ethoxycarbonyl-3-(1-oxo-2-isoindolinyl)propyl]amino-4-oxo-2,3,4,5-tetrahydro-1,5-benzoxazepine-5-acetic acid, 3(S)-[1-Carboxy-7-piperidinoheptyl]amino-4-oxo-2,3,4,5-tetrahydro-1,5-benzoxazepine-5-acetic acid, 3(S)-[1-Carboxy-5-(1-piperazinyl)pentyl]amino-4-oxo-2,3,4,5-tetrahydro-1,5-benzoxazepine-5-acetic acid, 3(S)-[1-Carboxy-5-(4-phenyl-1-piperazinyl)pentyl]amino-4-oxo-2,3,4,5-tetrahydro-1,5-benzoxazepine-5-acetic acid, 3(S)-[1-Carboxy-5-(4-(2-methoxyphenyl)-1-piperazinyl)pentyl]amino-4-oxo-2,3,4,5-tetrahydro-1,5-benzoxazepine-5-acetic acid, 3(S)-[1-Carboxy-5-(4-methyl-1-piperazinyl)pentyl]amino-4-oxo-2,3,4,5-tetrahydro-1,5-benzoxazepine-5-acetic acid, 3(S)-[1-Ethoxycarbonyl-3-(1-oxo-1,2,3,4-tetrahydroisoquinol-2-yl)propyl]amino-4-oxo-2,3,4,5-tetrahydro-1,5-benzoxazepine-5-acetic acid, 3(S)-[1-Carboxy-5-piperidinopentyl]amino-4-oxo-2,3,4,5-tetrahydro-1,5-benzoxazepine-5-acetic acid, 3(S)-[1-Carboxy-7-morpholinoheptyl]amino-4-oxo-2,3,4,5-tetrahydro-1,5-benzoxazepine-5-acetic acid, 3(S)-[1-Carboxy-7-(4-benzylpiperidino)heptyl]amino-4-oxo-2,3,4,5-tetrahydro-1,5-benzoxazepine-5-acetic acid, 3(S)-[1-Carboxy-7-(2,3,4,5-tetrahydro-3(1H)-benzazepin-3-yl)heptyl]amino-4-oxo-2,3,4,5-tetrahydro-1,5-benzoxazepine-5-acetic acid.

Salts of the compounds (I) include pharmaceutically acceptable salts, such as salts with an inorganic acid being exemplified by hydrochloride, hydrobromide, sulfate, nitrate, phosphate, etc., salts with organic acid being exemplified by acetate, tartarate, citrate, fumarate, maleate, toluenesulfonate, methanesulfonate, etc., metal salts being exemplified by sodium salts, potassium salts, calcium salts, aluminum salts, etc., and salts with bases being exemplified by triethylamine salts, guanidine salts, ammonium salts, hydrazine salts, quinine salts, cinchonine salts, etc.

The compound (I) of the present invention can be produced, for example, by subjecting a compound of the formula:

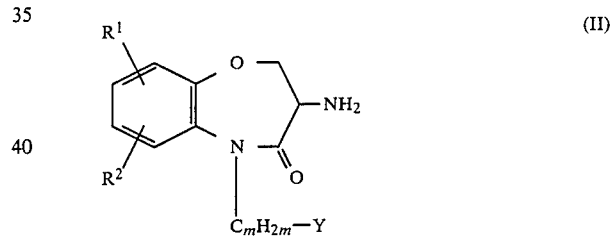

(II)

[wherein each of the symbols is as defined hereinbefore] and a compound of the formula:

(III)

[wherein $R^3$ and $R^4$ are as defined hereinbefore] to a condensation reaction under reductive conditions.

The said reductive conditions include reaction conditions of catalytic reduction using metals, such as platinum, palladium, Raney nickel and rhodium, or mixtures thereof with arbitrary supports as a catalyst; reduction with metal hydride compounds, such as lithium aluminum hydride, lithium borohydride, lithium cyanoborohydride, sodium borohydride and sodium cyanoborohydride; reduction with metallic sodium, metallic magnesium, etc. and alcohols; reduction with metals such as iron or zinc and acids such as hydrochloric acid or acetic acid; electrolytic reduction; reduction with reducing enzymes, and so forth. The above reaction is normally carried out in the presence of water or an organic solvent (e.g. methanol, ethanol, ethyl ether, dioxane, methylene chloride, chloroform, benzene, toluene, acetic acid, dimethylformamide, dimethylacetamide), and the reaction temperature varies with means of reduction employed, but generally is preferably in the range of −20° C. to +100° C. The reaction can be conducted at atmospheric pressure to achieve the desired object satisfactorily but may also be carried out under pressure or under reduced pressure according to the circumstances.

Also, the compound (I) of the present invention can be produced, for example, by subjecting a compound of the formula:

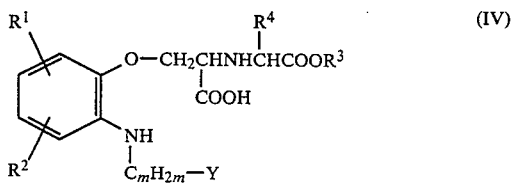

[wherein each of the symbols is as defined hereinbefore] to a dehydrative ring-closure reaction. The said dehydrative ring-closure reaction can be carried out, for example, by means of an ordinary amide bond formation reaction in peptides synthesis. Thus, the reaction can be conducted by employing such a peptide forming reagent as dicyclohexylcarbodiimide, N,N'-carbonyldiimidazole, diphenylphosphorylazide and diethyl phosphorocyanidate solely or adding an ordinary acid (e.g. hydrogen chloride, sulfuric acid, nitric acid, hydrogen bromide) to allow protonation of the amino group of the compound (IV), and then condensing the protonated compound with phenols, such as 2,4,5-trichlorophenol, pentachlorophenol, pentafluorophenol, 2-nitrophenol or 4-nitrophenol, or N-hydroxy compounds, such as N-hydroxysuccinimide, 1-hydroxybenzotriazole and N-hydroxypiperidine, in the presence of such a catalyst as dicyclohexylcarbodiimide to convert to the active ester derivative, followed by cyclization. The cyclization reaction, in any cases of cylizing the compound (IV) as such or after converting to its activated ester, can be promoted by adding preferably organic bases, for example, quaternary ammonium salts or tertiary amines (e.g. triethylamine, N-methylpiperidine). The reaction temperature is normally −20° to +50° C., preferably in the neighborhood of room temperature, and the solvent which is normally employed includes, for example, dioxane, tetrahydrofuran, acetonitrile, pyridine, N,N-dimethylformamide, N,N-dimethylacetamide, dimethylsulfoxide, N-methylpyrrolidone, chloroform, methylene chloride, etc., which may be used alone or as a solvent mixture.

The compound of the present invention can also be produced, for example, by subjecting a compound of the formula:

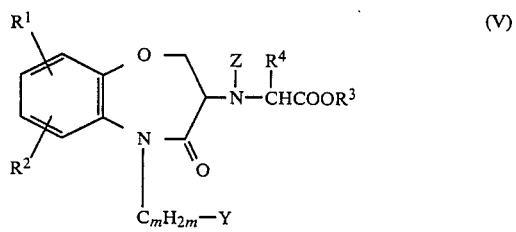

[wherein Z is a protective group removable by hydrolysis or catalytic reduction; other symbols are as defined hereinbefore] to a hydrolysis or catalytic reduction reaction. The protective group removable by hydrolysis as represented by Z in (V) includes all kinds of acyl groups and trityl group, and benzyloxycarbonyl, tert-butoxycarbonyl, trifluoroacetyl, trityl, etc., among others, are advantageous in the case of reactions under relatively mild reaction conditions. The protective group removable by catalytic reduction as represented by Z includes, for example, benzyl, diphenylmethyl, benzyloxycarbonyl, etc. The hydrolysis reaction in the said method is carried out in water or an organic solvent, such as methanol, ethanol, dioxane, pyridine, acetic acid, acetone and methylene chloride, or a solvent mixture thereof, and for the purpose of accelerating the reaction rate, it can be conducted as well by adding an acid (e.g. hydrochloric acid, hydrobromic acid, hydroiodic acid, hydrofluoric acid, sulfuric acid, methanesulfonic acid, p-toluenesulfonic acid, trifluoroacetic acid) or a base (e.g. sodium hydroxide, potassium hydroxide, potassium carbonate, sodium bicarbonate, sodium acetate, triethylamine). The above reaction is carried out normally within the range of about −20° to +150° C. The catalytic reduction reaction in the said method is conducted in water or an organic solvent, such as methanol, ethanol, dioxane and tetrahydrofuran, or a solvent mixture thereof in the presence of an appropriate catalyst, such as platinum and palladium-carbon. This reaction is carried out at atmospheric pressure or under pressure up to about 150 kg/cm$^2$ and at ordinary temperature or at a temperature up to +150° C., but the reaction generally proceeds satisfactorily at ordinary temperature and at atmospheric pressure.

The compound (I) of the present invention can be produced as well, for example, by subjecting the cyano group in a compound of the formula:

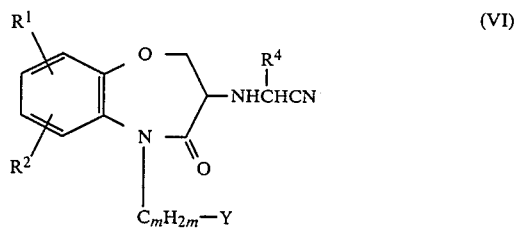

[wherein each of the symbols is as defined hereinbefore] to solvolysis.

The above solvolysis reaction is carried out in water or an organic solvent, such as methanol, ethanol, dioxane, pyridine, acetic acid, acetone and methylene chloride, or a solvent mixture thereof, and can also be conducted by adding an acid (e.g. hydrochloric acid, hydrobromic acid, hydroiodic acid, hydrofluoric acid, sulfuric acid, methanesulfonic acid, p-toluenesulfonic acid, trifluoroacetic acid) or a base (e.g. sodium hydroxide, potassium hydroxide, potassium carbonate, sodium bicarbonate, sodium acetate, triethylamine) for the purpose of accelerating the reaction rate. The reaction is normally carried out at a temperature within the range of about −20° to +150° C.

The compound (I) can also be produced by reacting the compound (II) with a compound of the formula:

[wherein R³ and R⁴ are as defined hereinbefore; $W^a$ is halogen or a group represented by the formula $R^aSO_2$—O— (wherein $R^a$ is lower alkyl, trifluoromethyl, phenyl or p-tolyl)]. The reaction is allowed to proceed by maintaining both of the compounds in a suitable solvent within the temperature range of about −20° to +150° C. On this occasion, it is also possible for the purpose of accelerating the reaction rate to allow a base such as potassium carbonate, sodium hydroxide, sodium bicarbonate, pyridine and triethylamine to coexist in the reaction system.

The compound (I) of the present invention can also be produced, for example, by reacting a compound of the formula:

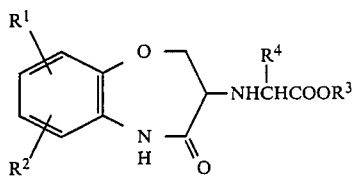
(VIII)

[wherein each of the symbols is as defined hereinbefore] with a compound of the formula:

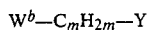
(IX)

[wherein $W^b$ is halogen or a group represented by the formula $R^bSO_2$—O— (wherein $R^b$ is lower alkyl, trifluoromethyl, phenyl or p-tolyl); m and Y are as defined hereinbefore]. The reaction is allowed to proceed by maintaining both of the compounds in a suitable solvent within the temperature ranging about −20° to +150° C. On this occasion, the reaction can be conducted by allowing a base, such as potassium carbonate, sodium hydroxide and sodium hydride, to coexist in the reaction system.

In the case of the compound (I) wherein R³ is hydrogen and/or Y is carboxyl, the compound (I) can also be produced by subjecting the ester compound wherein R³ is lower-($C_{1-4}$)-alkyl or/and Y is lower-($C_{1-4}$)-alkoxycarbonyl to a hydrolysis or elimination reaction, or by catalytic reduction of the benzyl ester compound wherein R³ is benzyl or/and Y is benzyloxycarbonyl.

In the case of the compound (I) wherein R³ is lower-($C_{1-4}$)-alkyl or/and Y is lower-($C_{1-4}$)-alkoxycarbonyl, further, such a compound can also be produced by subjecting the compound wherein R³ is hydrogen or/and Y is carboxyl to an esterification reaction.

In the case of the compound (I) wherein Y is esterified or amidated carboxyl, such a compound can also be produced, for example, by condensing a compound of the formula:

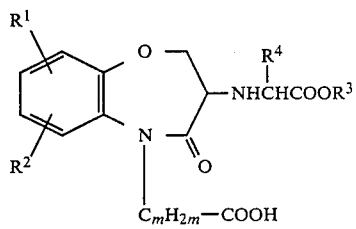
(X)

[wherein each of the symbols is as defined hereinbefore] with a compound of the formula:

(XI)

[wherein R⁵ is a lower alcohol residue, phenyl-lower-alcohol residue or α-amino acid residue whose carboxyl group may be protected with lower alkyl or phenyl-lower-alkyl].

Furthermore, the compound of the formula:

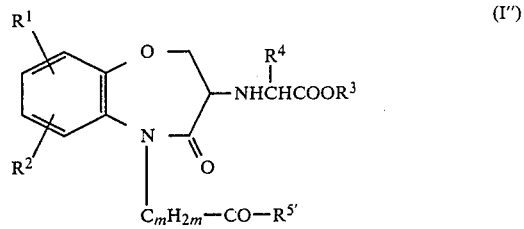
(I″)

[wherein $R^{5'}$ is an α-amino acid residue; other symbols are as defined hereinbefore] can also be obtained by subjecting the compound obtained in the above condensation reaction as represented by the formula:

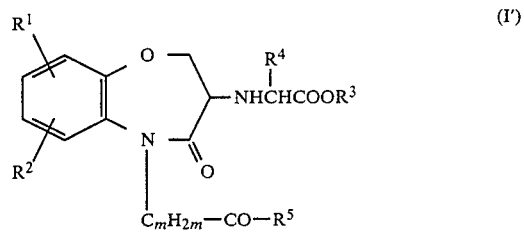
(I′)

[wherein R⁵ is α-amino acid residue whose carboxyl group is protected with lower alkyl or phenyl-lower alkyl and the other symbols is as defined hereinbefore], for example, to a hydrolysis reaction, elimination reaction or catalytic reduction.

In case compounds having a group which may interfere with a reaction are used [e.g. reaction of the compound (II) with the compound (III) or (IV)], compounds wherein the said group is protected with a known protecting group [e.g. benzyloxycarbonyl, tert-butoxycarbonyl, chloroacetyl, phthalimide, succinimide] are subjected to the reaction, followed by per se known deprotection reaction to give the desired compound.

In case R⁴ in the formula (I) is, for example, an alkyl group substituted by amino, mono- or di-loweralkylamino, acylamino or cycloalkylamino, the compound (I) can be represented by the formula:

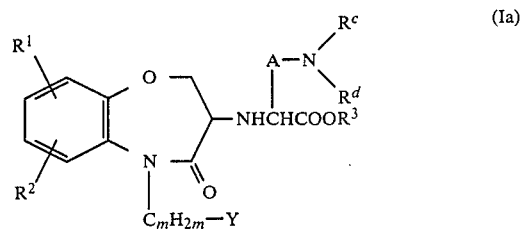
(Ia)

[wherein A is straight chain or branched chain alkylene group containing about 1–16 carbon atoms, $R^c$ and $R^d$ are independently hydrogen, lower-($C_{1-4}$)-alkyl, acyl or cycloalkyl, and the other symbols are as defined hereinbefore] and can be produced, for example, by the following method.

The compound (II) is reacted with a compound of the formula:

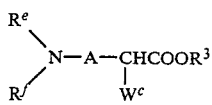  (VII')

[wherein $W^c$ is halogen or a group represented by the formula $R^gSO_2$—O— (wherein $R^g$ is lower alkyl, trifluoromethyl, phenyl or p-tolyl); one of $R^e$ and $R^f$ is hydrogen and the other is a protective group (e.g. benzoyl, acetyl) or both are cyclized with the adjacent nitrogen atom to form phthalimido or succinimido and the other symbols are as defined hereinbefore] to give a compound of the formula:

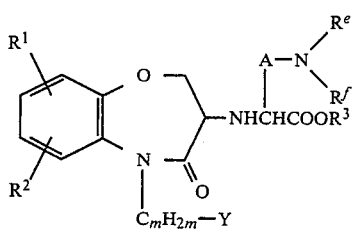  (Ia')

[wherein each of the symbols is as defined hereinbefore], and then the compound (Ia') is subjected to deprotection reaction to give the compound of the formula:

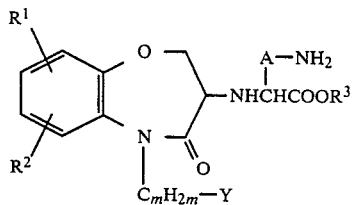  (Ib)

[wherein each of the symbols is as defined hereinbefore].

A compound of the formula (Ia) wherein $R^c$ and/or $R^b$ is lower alkyl or cycloalkyl, can be produced for example by reacting a corresponding aldehyde or ketone with the compound (Ib) under reductive conditions in water or an organic solvent (e.g. alcohol, ether, tetrahydrofuran, dimethylformamide, acetonitrile) or a mixture thereof, at a temperature ranging about $-20°$ to $+100°$ C.

The said reductive conditions include reaction conditions of catalytic reduction using metals, such as platinum, Raney nickel, palladium, or mixtures thereof with arbitrary supports as a catalyst; reduction with metal hydride compounds, such as lithium aluminum hydride, lithium borohydride, lithium cyanoborohydride, sodium borohydride and sodium cyanoborohydride; reduction with metallic sodium, metallic magnesium, etc. and alcohols; reduction with metals such as iron or zinc and acids such as hydrochloric acid or acetic acid; electrolytic reduction reduction with reducing enzymes, and so forth.

A compound of the formula (Ia) wherein $R^c$ and/or $R^d$ is acyl, can be produced for example by reacting an activated organic acid derivative such as acid anhydride or acid halide with the compound (Ib) in water or an organic solvent (e.g. ethyl acetate, methylene chloride, ether, benzene, toluene, triethylamine, dimethylformamide) or a mixture thereof, at a temperature ranging from about $-20°$ to $+150°$ C. For accelerating the reaction rate, an organic base (e.g. triethylamine, picoline, pyridine) or an inorganic base (e.g. sodium bicarbonate) may be added.

The compound of the formula (I) wherein $R^4$ is an alkyl group substituted by a hetero-alicyclic group and the nitrogen atom of the hetero-alicyclic group is bound to the alkyl group can be produced by subjecting the compound (Ib) and a compound of the formula:

  (XII)

[wherein $X^1$ is a ring-forming group and it represents a hetero-alicyclic group as the group of the formula

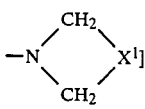]

to condensation reaction under reductive conditions.

The said reductive conditions include reaction conditions of catalystic reduction using metals, such as platinum, palladium, Raney nickel and rhodium, or mixtures thereof with arbitrary supports as a catalyst; reduction with metal hydride compounds, such as lithium aluminum hydride, lithium borohydride, lithium cyanoborohydride, sodium borohydride and sodium cyanoborohydride; reduction with metallic sodium, metallic magnesium, etc. and alcohols; reduction with metals such as iron or zinc and acids such as hydrochloric acid or acetic acid; electrolytic reduction; reduction with reducing enzymes, and so forth. The above reaction is normally carried out in the presence of water or organic solvent (e.g. methanol, ethanol, ethyl ether, dioxane, methylene chloride, chloroform, benzene, toluene, acetic acid, dimethylformamide, dimethylacetamide), and the reaction temperature varies with means of reduction employed, but generally is preferably in the range of $-20°$ C. to $+100°$ C. The reaction can be conducted at atmospheric pressure to achieve the desired object satisfactorily but may also be carried out under pressure or under reduced pressure depending on the circumstances.

The compound of the formula (I) wherein $R^4$ is an alkyl group substituted by a hetero-alicyclic group and the nitrogen atom of the hetero-alicyclic group is bound to the alkyl group can be produced by reacting the compound (Ib) and a compound of the formula:

  (XIII')

[wherein $W^d$ is halogen or a group represented by the formula $R^hSO_2$—O— (wherein $R^h$ is lower alkyl, trifluoromethyl, phenyl or p-tolyl) and $X^2$ is a ring-forming group and it represents a heteroalicyclic group as the group of the formula —N͟  X²]. The reaction is allowed to proceed by maintaining both of the compounds in a suitable solvent within the temperature range of about −20° to +150° C. On this occasion, it is also possible for the purpose of accelerating the reaction rate to allow a base such as potassium carbonate, sodium hydroxide, sodium bicarbonate, pyridine and triethylamine to coexist in the reaction system.

The compound of the compound (I) wherein $R^4$ is an alkyl group substituted by a hetero-alicyclic group and the hetero-alicyclic group has an unsubstituted imino group therein can be produced by subjecting the compound of the formula (I) wherein $R^4$ is an alkyl group substituted by a hetero-alicyclic group and the hetero-alicyclic group has an benzylimino or acylimino group, to catalytic reduction reaction, elimination reaction or solvolysis reaction.

The catalytic reduction reaction in the said method is conducted in water or an organic solvent, such as methanol, ethyl acetate, ethanol, dioxane and tetrahydrofuran, or a solvent mixture thereof in the presence of an appropriate catalyst, such as palladium-carbon. This reaction is carried out at atmospheric pressure or under pressure up to about 150 kg/cm² and at ordinary temperature or at a temperature up to +150° C.

The solvolysis or elimination reaction in the said method is carried out in water or an organic solvent such as methanol, ethanol, ethyl acetate, chloroform, tetrahydrofuran, dioxane, pyridine, acetic acid, acetone or methylene chloride or a solvent mixture thereof, and for the purpose of accelerating the reaction rate, it can be conducted as well by adding an acid (e.g. hydrochloric acid, hydrobromic acid, hydrofluoric acid, hydroiodic acid, sulfuric acid, methanesulfonic acid, p-toluenesulfonic acid, trifluoroacetic acid) or a base (e.g. sodium hydroxide, potassium hydroxide, potassium carbonate, sodium bicarbonate, sodium carbonate, sodium acetate). The above reaction is carried out normally within the range of about −20° to +150° C.

The compound of the formula (I) wherein $R^4$ is an alkyl group substituted by a hetero-alicyclic group and the hetero-alicyclic group has therein an imino group substituted by lower-($C_{1-4}$)-alkyl, aralkyl or acyl can be produced by reacting the compound of the formula (I) wherein $R^4$ is an alkyl group substituted by a hetero-alicyclic group and the hetero-alicyclic group has an unsubstituted imino group with a compound of the formula:

$$R^6-W^e \qquad (XIV)$$

[wherein $R^6$ is lower alkyl, aralkyl or acyl, and $W^e$ is halogen or a group represented by the formula $R^iSO_2-O-$ (wherein $R^i$ is lower alkyl, trifluoromethyl, phenyl or p-tolyl)]. The reaction is allowed to proceed by maintaining both of the compounds in a suitable solvent within the temperature range of about −20° to +150° C. On this occasion, it is also possible for the purpose of accelerating the reaction rate to allow a base such as potassium carbonate, sodium hydroxide, sodium bicarbonate, pyridine or triethylamine to coexist in the reaction system.

The compound of the formula (I) wherein $R^4$ is an alkyl group substituted by a hetero-alicyclic group and the hetero-alicyclic group has therein an imino group substituted by lower-($C_{1-4}$)-alkyl or aralkyl can be produced by subjecting the compound of the formula (I) wherein $R^4$ is an alkyl group substituted by a heteroalicyclic group and the hetero-alicyclic group has an unsubstituted imino group therein and a lower-($C_{1-4}$)- alkylaldehyde or aralkylaldehyde to condensation reaction under reductive conditions.

The said reductive conditions include reaction conditions of catalystic reduction using metals, such as platinum, palladium, Raney nickel and rhodium, or mixtures thereof with arbitrary supports as a catalyst; reduction with metal hydride compounds, such as lithium aluminum hydride, lithium borohydride, lithium cyanoborohydride, sodium borohydride and sodium cyanoborohydride; reduction with metallic sodium, metallic magnesium, etc. and alcohols; reduction with metals such as iron or zinc and acids such as hydrochloric acid or acetic acid; electrolytic reduction; reduction with reducing enzymes, and so forth. The above reaction is normally carried out in the presence of water or an organic solvent (e.g. methanol, ethanol, ethyl ether, dioxane, methylene chloride, chloroform, benzene, toluene, acetic acid, dimethylformamide, dimethylacetamide), and the reaction temperature varies with means of reduction employed, but generally is preferably in the range of −20° C. to +100° C. The reaction can be conducted at atmospheric pressure to achieve the desired object satisfactorily but may also be carried out under pressure or under reduced pressure depending on the circumstances.

The compound of the formula (I) wherein $R^4$ is an alkyl group substituted by an hetero-alicyclic group and the hetero-alicyclic group has an acylimino group therein can be produced by reacting the compound of the formula (I) wherein $R^4$ is an alkyl group substituted by a heteroalicyclic group and the hetero-alicyclic group has an unsubstituted imino group therein with a compound of the formula:

$$(R^7)_2O \qquad (XV)$$

[wherein $R^7$ is acyl].

The reaction is allowed to proceed by maintaining both of the compounds in water or a suitable solvent or a mixture thereof within the temperature range of about −20° to +150° C. On this occasion, it is also possible for the purpose of accelerating the reaction rate to allow a base such as potassium carbonate, sodium hydroxide, sodium bicarbonate, pyridine or triethylamine to coexist in the reaction system.

The salt of the compound (I) can be produced by the reaction for producing the compound (I) per se, and if desired, it can be produced by adding acid, alkali or base to the compound (I).

The object compound (I) of the present invention thus obtained can be isolated from the reaction mixture by utilizing conventional separation and purification means, for example, means such as extraction, concentration, neutralization, filtration, recrystallization, column chromatography and thin layer chromatography.

Depending on the kind of the substituents represented by $R^4$, there may exist at least two stereoisomers of the compound (I). These individual isomers and mixture thereof, naturally, both fall within the scope of the present invention, and such isomers can be produced individually, if desired. For example, a single optical isomer of the compound (I) can be obtained by carrying out the above reaction using a single isomer each of the starting compounds (II), (IV), (V), (VI), (VII), (VII') and (VIII), and when the product is a mixture of two or more isomers, it can be separated into individual isomers by a usual separation technique, for example, separation means such as methods of forming salts with optically active acids (e.g. camphorsulfonic acid, tartaric acid, dibenzoyltartaric acid, etc.) or optically active bases (e.g. cinchonine, cinchonidine, quinine, quinidine, α-methylbenzylamine, dehydroabiethylamine, etc.), a variety of chromatographic techniques and fractional recrystallization.

The compound of the present invention, namely the condensed, seven-membered ring compounds represented by the formula (I) and a salt thereof, exhibit inhibitory activities on angiotensin converting enzyme, bradikinin decomposing enzyme (kininase), etc. in animals, in particular, mammals (e.g. human, dog, cat, rabbit, guinea pig, rat), and are useful, for example, as drugs for diagnosis, prevention or treatment of hypertension and hypertension-induced circulatory diseases (e.g. cardiopathy, cerebral apoplexy). The compound of the present invention is of low toxicity, well absorbed even on oral administration and highly stable and has long-lasting effect. Therefore, when it is used as the above-mentioned drugs, it can be administered orally or parenterally, per se or in admixture with suitable, pharmaceutically acceptable carriers, excipients or diluents in various pharmaceutical formulations such as powders, granules, tablets, capsules injectable solutions, etc. While the dosage level generally varies depending upon the conditions of the diseases to be treated as well as the administration route used, in the case of administration to human adult for the purpose of treatment of renal or essential hypertention, for example, the compound may be desirably administered orally at a single dose of about 0.02–20 mg/kg, preferably about 0.02–2 mg/kg, more preferably about 0.04–0.8 mg/kg, or intravenously at about 0.002–1 mg/kg, preferably about 0.02–0.2 mg/kg, about 1 to 5 times, preferably about 1 to 3 times, more preferably about once or twice per day according to the conditions.

The starting compounds (II), (IV), (V), (VI) and (VIII) of the present invention can be easily prepared, for example, by the methods as illustrated in the following reaction schema.

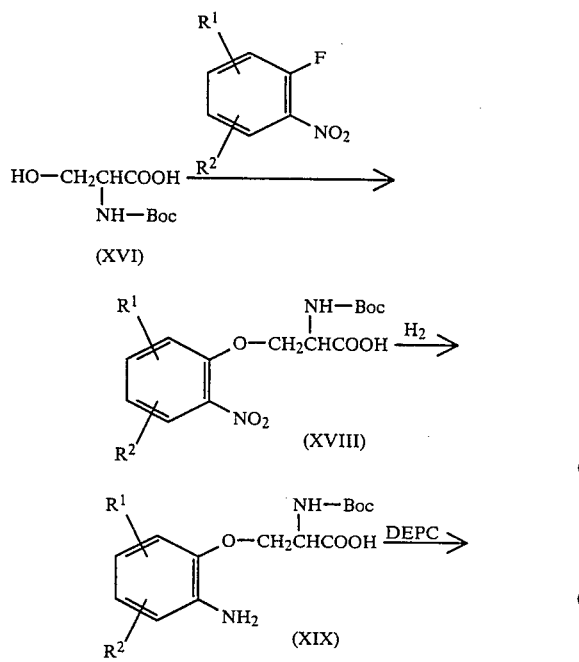

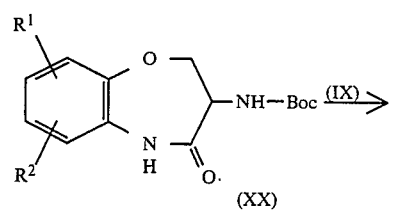

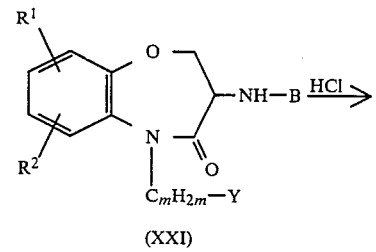

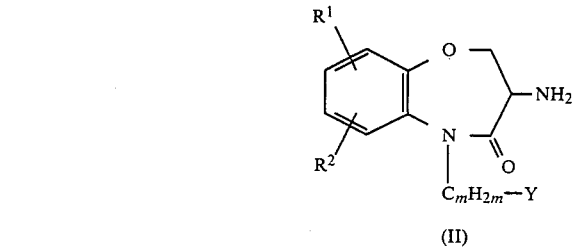

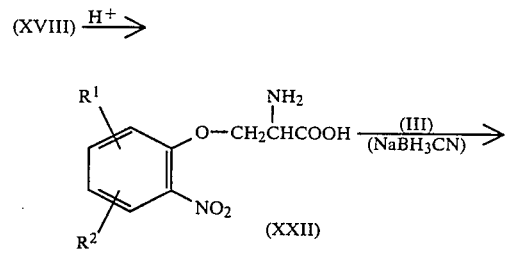

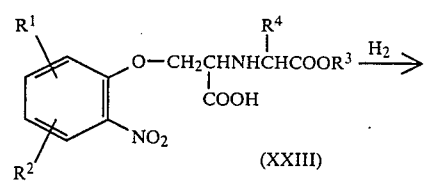

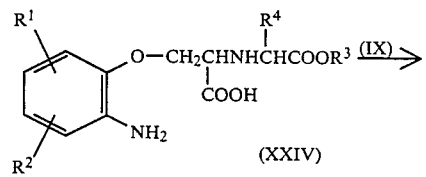

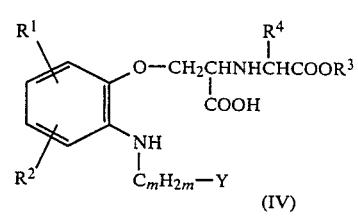

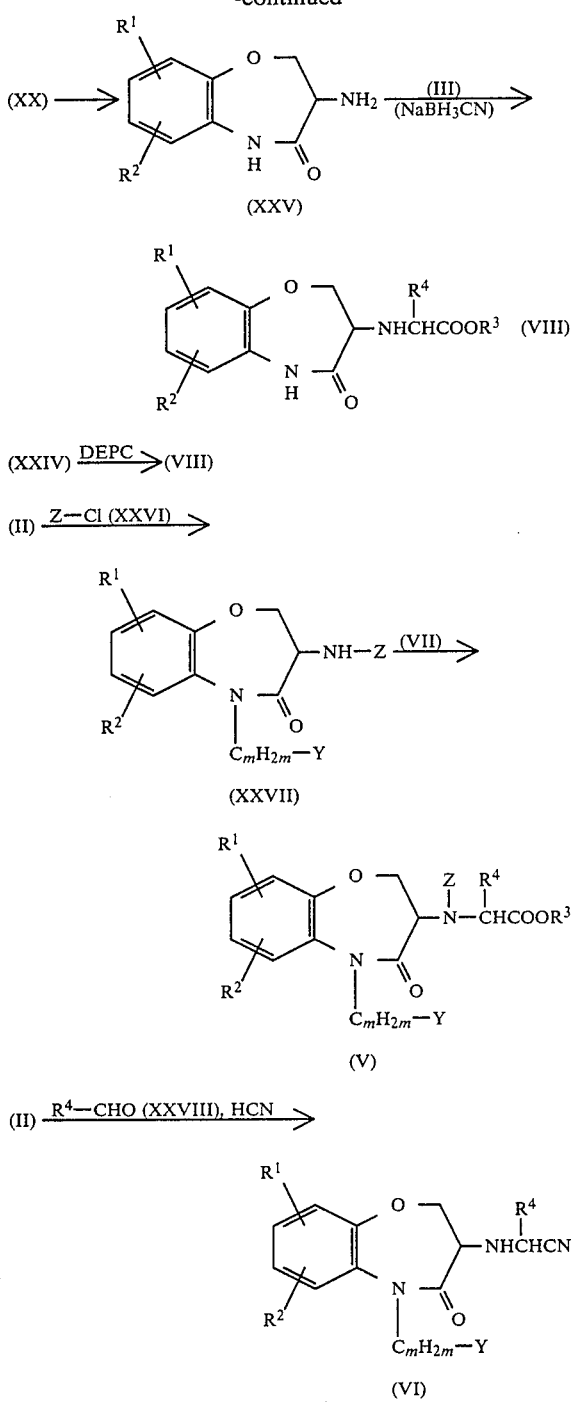

In the above reactions, Boc is tert-butoxycarbonyl; DEPC is diethyl phosphorocyanidate; and the other symbols are as defined hereinbefore.

The process for preparing the compound (II) as shown in the above reaction schema is now illustrated in more detail. The compound (XVI) as a starting compound is treated with 2 equivalents of sodium hydride in a polar solvent such as N,N-dimethylformamide and then the compound is reacted with the compound (XVII) to give the compound (XVIII).

The reaction of (XVIII)→(XIX) is a reduction reaction of the nitro group to the amino group, and conventionally known reduction techniques can be employed. Thus, the reduction techniques include catalytic reduction using as a catalyst for example palladium-carbon, palladium supported with barium sulfate, sulfided palladium, Raney nickel, platinum, etc., reduction with such a metal as zinc, tin, stannous chloride or iron and acid or alkali, and so forth. The dehydrative ring-closure reaction of the resultant compound (XIX) to the compound (XX) can be advantageously carried out in the presence of a known dehydrative coupling agent. Such dehydrative coupling agent includes, for example, dicyclohexylcarbodiimide, carbonyldiimidazole, diethyl phosphorocyanidate, etc. As the solvent, use is made for example of dioxane, methylene chloride, acetonitrile, N,N-dimethylformamide, tetrahydrofuran, etc. and the reaction is normally conducted at a temperature in the range of $-10°$ to $+100°$ C. For the purpose of allowing the reaction to proceed advantageously, a base such as triethylamine or pyridine can also be added to the reaction solution as a catalyst. The preparation of the compound (XXI) through a condensation reaction between the compounds (XX) and (IX) can be effected normally by condensation in a solvent such as N,N-dimethylformamide, dimethylsulfoxide or acetonitrile in the presence of such a base as sodium hydride or potassium carbonate at a temperature in the range of about $-10°$ to $+100°$ C. Then, the reaction of (XXI)→(II) can be conducted by treating with hydrogen chloride in a solvent such as ethyl acetate at a temperature in the range of about $-10°$ to $+100°$ C.

In the process for producing the compound (IV), the reaction of (XVIII)→(XXII) can be conducted in a manner similar to the reaction of (XXI)→(II). The compound (XXIII) can be produced by subjecting the compounds (XXII) and (III) to a condensation reaction. The compound (IV) can be prepared by subjecting the compound (XXIII) to an ordinary reduction reaction of the nitro group to the amino group and subsequently a condensation reaction with the compound (IX).

In the process for producing the compound (V), the compound (XXVII) can be produced by applying a per se known amino protecting reaction for amino acids to the compound (II). The reaction of the compounds (XXVII) and (VII) is allowed to proceed by maintaining both of the compounds in an appropriate solvent within the temperature range of about $-20°$ to $+150°$ C. On this occasion, a base such as potassium carbonate, sodium hydroxide, sodium bicarbonate, pyridine or triethylamine can be made to coexist as a deacidifying agent in the reaction system for the purpose of accelerating the reaction rate.

In the process for producing the compound (VI), the compound (VI) can be obtained from the compounds (II) and (XXVIII) and hydrogen cyanide used as starting compounds according to the Strecker reaction which is per se known.

In the process for producing the compound (VIII), the reaction of (XX)→(XXV) can be promoted in a manner similar to the reaction of (XXI)→(II). The compound (VIII) can be produced by subjecting the compounds (XXV) and (III) to a reaction similar to that of compounds (XXII) and (III). The compound (VIII) can also be produced by subjecting the compound (XXIV) to a reaction similar to that of (XIX)→(XX).

The compound (II) can be produced, for example, according to the following reaction scheme besides the reaction (XXI)→(II).

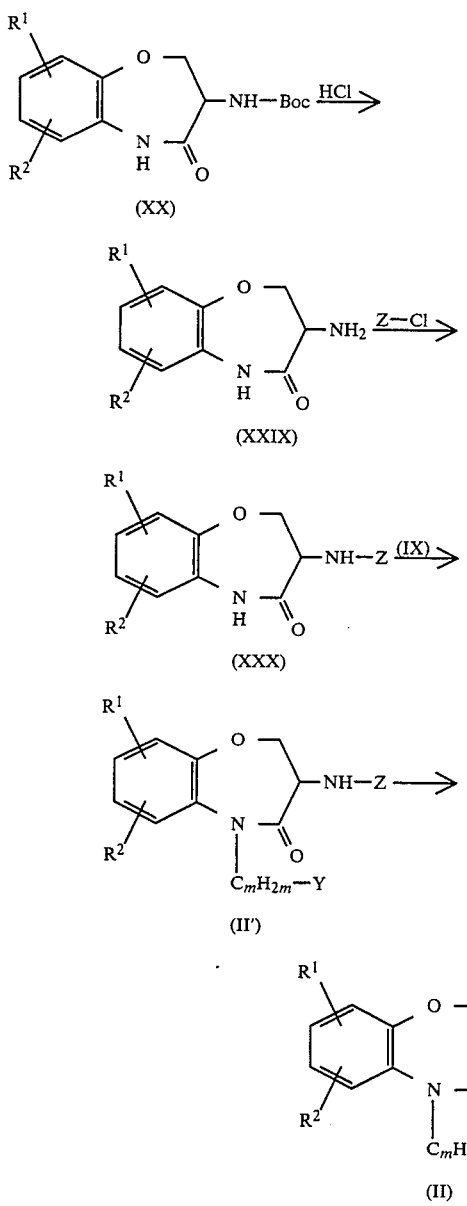

(XX)

(XXIX)

(XXX)

(II')

(II)

In the above reaction scheme, each of the symbols is as defined hereinbefore.

The reaction (XX)→(XXIX) can be conducted under the conditions similar to those of the reaction (XXI)→(II) and the reaction (XXIX)→(XXX) can be conducted under the conditions similar to those of the reaction (II)→(XXVII).

The compound (II') can be produced by subjecting the compounds (XXX) and (IX) to the reaction similar to that of the compounds (XX) and (IX).

The compound (II) can be produced by subjecting the compound (II') to hydrolysis or catalytic reduction under the conditions similar to those of the reaction (V)→(I).

This invention also provides the compounds (II) which is industrially advantageous as an intermediate for synthesis of the novel compound (I) having the remarkable activities.

The compounds of the formulae (III) and (VII) wherein $R^4$ is an alkyl group substituted by an hetero-alicyclic group, which are used for the production of the compound (I), can be produced, for example, by the method as shown in the following reaction scheme.

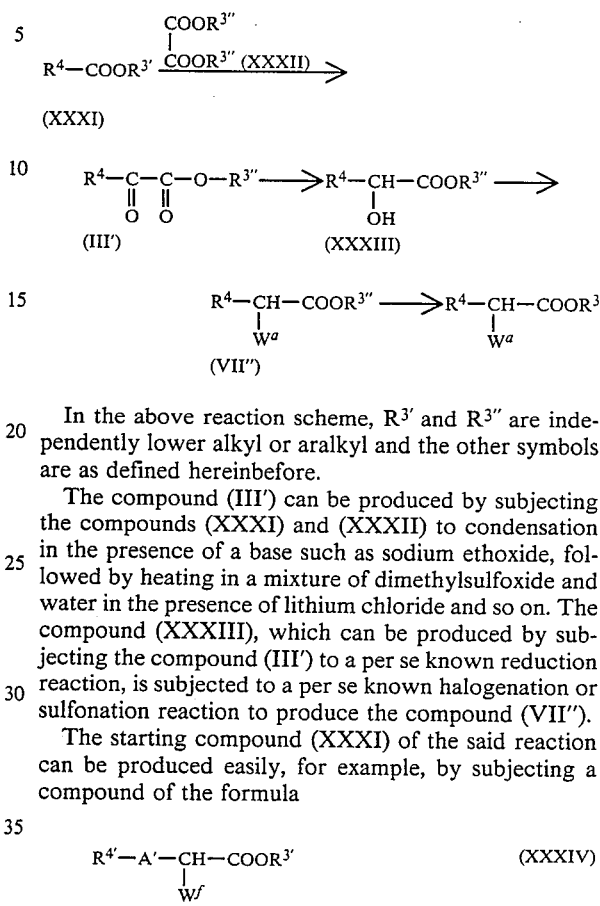

In the above reaction scheme, $R^{3'}$ and $R^{3''}$ are independently lower alkyl or aralkyl and the other symbols are as defined hereinbefore.

The compound (III') can be produced by subjecting the compounds (XXXI) and (XXXII) to condensation in the presence of a base such as sodium ethoxide, followed by heating in a mixture of dimethylsulfoxide and water in the presence of lithium chloride and so on. The compound (XXXIII), which can be produced by subjecting the compound (III') to a per se known reduction reaction, is subjected to a per se known halogenation or sulfonation reaction to produce the compound (VII'').

The starting compound (XXXI) of the said reaction can be produced easily, for example, by subjecting a compound of the formula $$R^{4'}-A'-CH-COOR^{3'} \quad (XXXIV)$$
$$\quad\quad\quad\quad\quad | \quad\quad\quad$$
$$\quad\quad\quad\quad\quad W^f$$

wherein $R^{4'}$ is a hetero-alicyclic group, $W^f$ is halogen, A' represents A as A'—CH$_2$ and the other symbols are as defined hereinbefore, to a per se known reduction reaction.

In case that compounds wherein $R^{4'}$ has a group which may interfere the reactions, the reaction may be conducted after protecting the group with a protective group such as $C_{1-5}$ alkanoyl (e.g. acetyl), benzoyl, phenyl-lower alkoxycarbonyl (e.g. benzyloxycarbonyl) or lower alkoxycarbonyl (e.g. tert-butoxycarbonyl).

The compounds of the formulae (III'), (XXXIII) and (VII'') wherein $R^{3''}$ is hydrogen can be produced easily, for example, by subjecting the compounds (III'), (XXXIII) and (VII'') to hydrolysis, respectively.

The compounds (VII) and (VII') can be produced easily by known methods described in literature references [e.g.; Methoden der Organischen Chemie (1960), Halogenverbindungen pp. 197-210 (Georg Thieme Verlag); Japanese Patent Unexamined Publication No. 42654/1972; Chemical Abstracts 64 P14139 e (1966); Chemical Abstracts 47, P4361 c (1953); Chemical Abstracts 50, 8503 e (1956); Chemical Abstracts 53, P17908 h (1959)].

In the processes for producing the compound (I) and intermediates thereof, the compounds which are used in the reactions may be used in the form of salts, such as inorganic acid salts being exemplified by hydrochloride, hydrobromide, sulfate, nitrate, phosphate, etc., organic acid salts being exemplified by acetate, tartarate, citrate, fumarate, maleate, toluenesulfonate, methanesulfonate, etc., metal salts being exemplified by sodium salt, potassium salt, calcium salt, aluminum salt, etc., and salts with bases being exemplified by triethylamine salt, guanidine salt, ammonium salt, hydrazine salt, quinine salt, cinchonine salt, etc., so long as they do not interfere with such reactions.

EXAMPLE 1

In 200 ml of N,N-dimethylformamide is suspended 10.1 g of 60% sodium hydride (oily), and a solution of 25 g of Boc-L-serine in 10 ml of N,N-dimethylformamide is added dropwise to the suspension in a stream of nitrogen at 0° C. with stirring. After stirring is continued at 0° C. until the evolution of hydrogen stops, 19 g of o-fluoronitrobenzene is added dropwise to the mixture. After the stirring at room temperature for 4 hours, the reaction mixture is poured in ice-cooled water containing dilute hydrochloric acid, followed by extraction with ethyl acetate. The organic layer is washed with water and dried, and then the solvent is evaporated off under reduced pressure. The resulting residue is purified by silica gel column chromatography (hexane-ethyl acetate=1:1) to give 30 g of O-(o-nitrophenyl)-Boc-L-serine as a colorless oil.

EXAMPLE 2

In 500 ml of methanol is dissolved 30 g of O-(o-nitrophenyl)-Boc-L-serine obtained in Example 1, and catalytic reduction is conducted in a stream of hydrogen at ordinary temperature and at atmospheric pressure with 1 g of 10% palladium-carbon used as a catalyst. The catalyst is filtered off, and the filtrate is concentrated under reduced pressure. The resulting residue is recrystallized from ethyl acetate to give 23 g of O-(o-aminophenyl)-Boc-L-serine as colorless crystals, melting at 90°–91° C.

Elemental Analysis for $C_{14}H_{20}N_2O_5$: Calcd.: C, 56.75; H, 6.80; N, 9.45; Found: C, 56.48; H, 6.82; N, 9.43

EXAMPLE 3

In 120 ml of N,N-dimethylformamide is dissolved 21.4 g of O-(o-aminophenyl)-Boc-L-serine obtained in Example 2, and 14 g of diethyl phosphorocyanidate is added dropwise to the solution with stirring at ice bath temperature. The mixture is stirred for 10 minutes, and 7 g of triethylamine is added dropwise to the mixture. After stirring for 1 hour, the mixture is poured in ice-cooled water. The deposited material is collected by filtration, washed with water, dried and recrystallized from ethyl acetate-hexane to give 12.3 g of 3(S)-tert-butoxycarbonylamino-2,3,4,5-tetrahydro-1,5-benzoxazepine-4-one as colorless plates, melting at 202°–203° C.

$[\alpha]_D^{24.5} -195°$ (c=0.9 in methanol)

Elemental Analysis for $C_{14}H_{18}N_2O_4$: Calcd.: C, 60.42; H, 6.52; N, 10.07; Found: C, 60.69; H, 6.71; N, 9.99

EXAMPLE 4

In 150 ml of N,N-dimethylformamide is dissolved 12.3 g of 3(S)-tert-butoxycarbonylamino-2,3,4,5-tetrahydro-1,5-benzoxazepine-4-one, and 8.7 g of benzyl chloroacetate, 8.7 g of anhydrous potassium carbonate and 1 g of potassium iodide are added to the solution. After stirring for 15 hours, the mixture is poured in ice-cooled water. The deposited material is collected by filtration, washed with water and recrystallized from ethyl acetate-hexane to give 11.7 g of benzyl 3(S)-tert-butoxycarbonylamino-4-oxo-2,3,4,5-tetrahydro-1,5-benzoxazepine-5-acetate as colorless prisms, melting at 122°–124° C.

$[\alpha]_D^{24} -180°$ (c=0.1 in methanol)

Elemental Analysis for $C_{23}H_{26}N_2O_6$; Calcd.: C, 64.78; H, 6.14; N, 6.57; Found: C, 64.65; H, 6.21; N, 6.69

EXAMPLE 5

To 7.6 g of benzyl 3(S)-tert-butoxycarbonylamino-4-oxo-2,3,4,5-tetrahydro-1,5-benzoxazepine-5-acetate is added 30 ml of hydrogen chloride-ethyl acetate solution (5N) and the mixture stands for 3 hours at room temperature. The mixture is concentrated under reduced pressure and the resulting residue is crystallized from a mixture of ethyl acetate and ether to give 6.2 g of benzyl 3(S)-amino-4-oxo-2,3,4,5-tetrahydro-1,5-benzoxazepine-5-acetate hydrochloride as a colorless crystalline powder, melting at 169°–172° C.

Elemental Analysis for $C_{18}H_{18}N_2O_4 \cdot HCl$: Calcd.: C, 59.59; H, 5.28; N, 7.72; Found: C, 59.09; H, 5.12; N, 7.55

$[\alpha]_D^{24} -202°$ (c=0.6 in methanol)

EXAMPLE 6

In 100 ml of ethanol is dissolved 4.5 g of sodium, and 27.8 g of ethyl 4-ethylhexanoate and 29 g of diethyl oxalate are added to the solution, and the low-boiling substance is removed by evaporation under reduced pressure at about 70° C. for 40 minutes. After cooling, 500 ml of water and 300 ml of petroleum ether are added to the brown viscous residue, and the mixture is thoroughly shaken. The aqueous layer is separated off and the petroleum layer is extracted twice with 50 ml each of 1N sodium hydroxide solution. The extracts are combined, acidified slightly with concentrated hydrochloric acid and extracted twice with 200 ml each of ethyl acetate. The extract is dried over anhydrous magnesium sulfate and concentrated under reduced pressure. One hundred and ten (110) ml of 10% aqueous dimethylsulfoxide and 10 g of sodium chloride are added to the oily residue, and the mixture is stirred at 160° C. for 2.5 hours. After the reaction mixture is cooled, 500 ml of water is added, followed by extraction with 300 ml of ethyl acetate. The extract is washed with water, dried over anhydrous magnesium sulfate and concentrated under reduced pressure. The brown oily residue is distilled under reduced pressure to give 16.4 g of ethyl 5-ethyl-2-oxoheptanoate as a pale yellow oil.

Boiling point: 83°–88° C. (2 mmHg).

EXAMPLES 7–12

By carrying out the reaction using the carboxylic acid ethyl ester as shown in Table 1 as a starting compound similarly to the reaction of Example 6, the corresponding α-keto ester derivative is obtained.

TABLE 1

| Ex. No. | Starting Compound | Keto-ester obtained |
|---|---|---|
| 7 | cycloheptyl-CH₂CH₂COOC₂H₅ | cycloheptyl-CH₂CH₂COCOOC₂H₅ |
| 8 | CH₃-C₆H₄-CH₂CH₂COOC₂H₅ | CH₃-C₆H₄-CH₂CH₂COCOOC₂H₅ |
| 9 | (tetrahydropyran-yl)-CH₂CH₂COOC₂H₅ | (tetrahydropyran-yl)-CH₂CH₂COCOOC₂H₅* |
| 10 | (tetrahydrothiopyran-yl)-CH₂CH₂COOC₂H₅ | (tetrahydrothiopyran-yl)-CH₂CH₂COCOOC₂H₅* |
| 11 | C₆H₅-CH₂OC(O)-N(piperidine)-CH₂CH₂COOC₂H₅ | C₆H₅-CH₂OC(O)-N(piperidine)-CH₂CH₂COCOOC₂H₅* |
| 12 | CH₃(CH₂)₇COOC₂H₅ | CH₃(CH₂)₇COCOOC₂H₅ |

*Removal of ethoxycarbonyl is conducted with use of lithium chloride.

EXAMPLE 13

In 30 ml of 5N hydrogen chloride-ethyl acetate solution is dissolved 5 g of 3(S)-tert-butoxycarbonylamino-2,3,4,5-tetrahydro-1,5-benzoxazepine-4-one, and the mixture is allowed to stand at room temperature for 3 hours. The deposited crystals are collected by filtration to give 3.8 g of 3(S)-amino-2,3,4,5-tetrahydro-1,5-benzoxazepine-4-one hydrochloride as a colorless needles, melting at 230°–240° C. (decomposition).

Elemental Analysis for $C_9H_{10}N_2O_2 \cdot HCl$; Calcd.: C, 50.36; H, 5.17; N, 13.05; Found: C, 50.30; H, 5.18; N, 13.02

$[\alpha]_D -277°$ (c=0.4 in methanol)

EXAMPLE 14

To a mixture of 100 ml of ethyl acetate and 50 ml of water is added 1.5 g of 3(S)-amino-2,3,4,5-tetrahydro-1,5-benzoxazepine-4-one hydrochloride, and 1.5 ml of benzyloxycarbonyl chloride is added dropwise to the mixture at ice bath temperature with stirring. After stirring for 1 hour, the ethyl acetate layer separated, washed with water, dried over anhydrous magnesium sulfate and concentrated under reduced pressure. To the residue is added ethyl ether and the deposited crystals are collected by filtration to give 2 g of 3(S)-benzyloxycarbonylamino-2,3,4,5-tetrahydro-1,5-benzoxazepine-4-one. This product is recrystallized from a mixture of ethyl acetate and ether to give colorless needles melting at 157°–159° C.

Elemental Analysis for $C_{17}H_{16}N_2O_4$; Calcd.: C, 65.38; H, 5.16; N, 8.97; Found: C, 65.54; H, 5.19; N, 8.95

$[\alpha]_D -175°$ (c=0.7 in methanol)

EXAMPLE 15

3(S)-Benzyloxycarbonylamino-2,3,4,5-tetrahydro-1,5-benzoxazepine-4-one (1.9 g) obtained in Example 14 is reacted with 1.1 g of tert-butyl chloroacetate in a manner similar to that of Example 4 to give 2.5 g of tert-butyl 3(S)-benzyloxycarbonylamino-4-oxo-2,3,4,5-tetrahydro-1,5-benzoxazepine-5-acetate as a pale yellow oil.

IR $\nu_{max}^{neat}$ cm$^{-1}$: 3350(NH); 1730, 1680 (C=O)

Mass spectrum (m/e): 426 (M⁺)

EXAMPLE 16

In 30 ml of ethanol is dissolved 2 g of benzyl 3(S)-amino-4-oxo-2,3,4,5-tetrahydro-1,5-benzoxazepine-5-acetate hydrochloride obtained in Example 5, and 0.45 g of sodium acetate, 0.35 g of acetic acid, 4.5 g of ethyl 2-oxo-4-phenylbutyrate and 10 g of Molecular sieve 4A are added to the solution. After the mixture is stirred at room temperature for 30 minutes, a solution of 0.34 g of sodium cyanoborohydride in 30 ml of ethanol is added dropwise to the mixture over a period of 3 hours. After a solution of 1 g of sodium cyanoborohydride in 30 ml of ethanol is further added dropwise to the mixture over a period of 1 hour, the reaction mixture is concentrated under reduced pressure. To the residue are added 100 ml of water and 200 ml of ethyl acetate, and the mixture is stirred. After the insoluble substance is removed by filtration, the ethyl acetate layer is dried over anhydrous magnesium sulfate and concentrated under reduced pressure. After 50 ml of ethyl ether and 1 g of oxalic acid is added to the residue, the mixture is shaken and diluted with 300 ml of petroleum ether. The resulting mixture is allowed to stand overnight. The supernatant layer is removed by decantation, and 50 ml of water and 300 ml of ethyl acetate are added to the precipitate, followed by neutralization with an excess of sodium bicarbonate. The ethyl acetate layer is dried over anhydrous magnesium sulfate and concentrated under reduced pressure to give an oil, which is separated and purified by silica gel column chromatography (hexane: ethyl acetate=5:1-2:1) to yield firstly tert-butyl 3(S)-[1(R)-ethoxycarbonyl-3-phenylpropyl]amino-4-oxo-2,3,4,5-tetrahydro-1,5-benzoxazepine-5-acetate as an oil. This product is dissolved in a mixture of 100 ml of petroleum ether and 20 ml of ether, and 1 ml of a solution of hydrogen chlorideethyl acetate (5N) is added to the solution to yield 0.9 g of hydrochloride salt of the product as a colorless powder.

Elemental Analysis for $C_{30}H_{32}N_2O_6.HCl$; Calcd.: C, 65.15; H, 6.01; N, 5.07; Found: C, 64.65; H, 6.17; N, 4.94
$[\alpha]_D^{24} - 86.9°$ (c=0.5 in methanol)

From the subsequently succeeding fraction, benzyl 3(S)-[1(S)-ethoxycarbonyl-3-phenylpropyl]amino-4-oxo-2,3,4,5-tetrahydro-1,5-benzoxazepine-5-acetate is obtained as a colorless oil. This product is converted to hydrochloride salt thereof as a colorless powder (yield 1.3 g) in the same manner as mentioned above.

Elemental Analysis for $C_{30}H_{32}N_2O_6.HCl$; Calc.: C, 65.15; H, 6.01; N, 5.07; Found: C, 64.97; H, 6.18; N, 4.99
$[\alpha]_D^{24} - 62.4°$ (c=0.5 in methanol)

EXAMPLE 17

In 100 ml of ethanol is dissolved 0.7 g of benzyl 3(S)-[1(R)-ethoxycarbonyl-3-phenylpropyl]amino-4-oxo-2,3,4,5-tetrahydro-1,5-benzoxazepine-5-acetate hydrochloride obtained in Example 16, and catalytic reduction is conducted at ordinary temperature and under atmospheric pressure using 0.5 g 10% palladium-carbon (containing 50% moisture) as a catalyst, when the absorption of hydrogen stops, the catalyst is filtered off and the filtrate is concentrated under reduced pressure. Petroleum ether is added to the residue to give 0.53 g of 3(S)-[1(R)-ethoxycarbonyl-3-phenylpropyl]amino-4-oxo-2,3,4,5-tetrahydro-1,5-benzoxazepine-5-acetic acid hydrochloride as a colorless powder.

Elemental Analysis for $C_{23}H_{26}N_2O_6.HCl.H_2O$: Calcd.: C, 57.44; H, 6.08; N, 5.83; Found: C, 57.39; H, 5.97; N, 5.74
$[\alpha]_D^{24} - 98.6°$ (c=0.6 in methanol)

EXAMPLE 18

Catalytic reduction of 1.1 g of benzyl 3(S)-[1(S)-ethoxycarbonyl-3-phenylpropyl]amino-4-oxo-2,3,4,5-tetrahydro-1,5-benzoxazepine-5-acetate hydrochloride obtained in Example 16 is carried out in a manner similar to that described in Example 17 to give 0.8 g of 3(S)-[1(S)-ethoxycarbonyl-3-phenylpropyl]amino-4-oxo-2,3,4,5-tetrahydro-1,5-benzoxazepine-5-acetic acid hydrochloride as a colorless powder.

Elemental Analysis for $C_{23}H_{26}N_2O_6.HCl.\frac{1}{2}H_2O$: Calcd.: C, 58.54; H, 5.98; N, 5.94; Found: C, 58.45; H, 6.08; N, 5.71
$[\alpha]_D^{24} - 69.9°$ (c=0.6 in methanol)

To this product is added 10 ml of water and the solution is extracted three times with 50 ml each of ethyl acetate. The extract is dried over anhydrous magnesium sulfate and concentrated under reduced pressure. To the oily residue ethyl ether is added and the resulting mixture is allowed to stand. The deposited crystals are filtered off and the filtrate is treated with hydrogen chloride-ethyl acetate solution to deposit powder, which is collected by filtration to give 3(S)-[1(S)-ethoxycarbonyl-3-phenyl-propyl]amino-4-oxo-2,3,4,5-tetrahydro-1,5-benzoxazepine-5-acetic acid hydrochloride which has higher optical purity.

$[\alpha]_D - 103°$ (c=0.5 in methanol)

EXAMPLE 19

In a mixture of 1 ml of ethanol and 4 ml of sodium hydroxide solution (1N) is dissolved 0.15 g of 3(S)-[1(R)-ethoxycarbonyl-3-phenylpropyl]amino-4-oxo-2,3,4,5-tetrahydro-1,5-benzoxazepine-5-acetic acid hydrochloride obtained in Example 17, and the resulting mixture is allowed to stand for 2 hours and acidified slightly with 1N hydrochloric acid. The deposited powder is collected by filtration, dried and dissolved in 10 ml of ethanol. The insoluble substance is filtered off and filtrate is dried under reduced pressure to give 0.03 g of 3(S)-[1(R)-carboxy-3-phenylpropyl]amino-4-oxo-2,3,4,5-tetrahydro-1,5-benzoxazepine-5-acetic acid as a colorless powder.

Elemental Analysis for $C_{21}H_{22}N_2O_6.3/2H_2O$: Calcd.: C, 59.29; H, 5.92; N, 6.59; Found: C, 59.63; H, 5.64; N, 6.73
$[\alpha]_D^{25} - 112°$ (c=0.3 in methanol)

EXAMPLE 20

Hydrolysis of 0.16 g of 3(S)-[1(S)-ethoxycarbonyl-3-phenylpropyl]amino-4-oxo-2,3,4,5-tetrahydro-1,5-benzoxazepine-5-acetic acid hydrochloride obtained in Example 18 is carried out in a manner similar to that described in Example 19. The obtained crystals are recrystallized from ethanol to give 0.1 g of 3(S)-[1(S)-carboxy-3-phenylpropyl]amino-4-oxo-2,3,4,5-tetrahydro-1,5-benzoxazepine-5-acetic acid as a colorless prisms, melting at 127°-130° C.

Elemental Analysis for $C_{21}H_{22}N_2O_6.H_2O$: Calcd.: C, 60.57; H, 5.81; N, 6.73; Found: C, 60.44; H, 5.69; N, 6.68
$[\alpha]_D^{25} - 86.5°$ (c=0.4 in methanol)

EXAMPLE 21

Benzyl 3(S)-amino-4-oxo-2,3,4,5-tetrahydro-1,5-benzoxazepine-5-acetate hydrochloride (1.5 g) and ethyl 4-cyclohexyl-2-oxobutyrate (2.63 g) are subjected to reductive alkylation reaction in a manner similar to that described in Example 16, and the product is purified by silica gel column chromatography (hexane:ethal acetate=5:1-4:1). From the first fraction, 0.4 g of benzyl 3(S)-[1(R)-ethoxycarbonyl-3-cyclohexylpropyl]amino-4-oxo-2,3,4,5-tetrahydro-1,5-benzoxazepine-5-acetate is obtained as a colorless oil.

Elemental Analysis for $C_{30}H_{38}N_2O_6$: Calcd.: C, 68.94; H, 7.33; N, 5.36; Found: C, 69.03; H, 7.27; N, 5.57
$[\alpha]_D^{24} - 110°$ (c=1 in methanol)

The second fraction gives 0.4 g of benzyl 3(S)-[1(S)-ethoxycarbonyl-3-cyclohexylpropyl]amino-4-oxo-2,3,4,5-tetrahydro-1,5-benzoxazepine-5-acetate as a colorless oil.

Elemental Analysis for $C_{30}H_{38}N_2O_6$: Calcd.: C, 68.94; H, 7.33; N, 5.36; Found: C, 69.08; H, 7.34; N, 5.60

EXAMPLE 22

Catalytic reduction of benzyl 3(S)-[1(R)-ethoxycarbonyl-3-cyclohexylpropyl]amino-4-oxo-2,3,4,5-tetrahydro-1,5-benzoxazepine-5-acetate (0.35 g) obtained in Example 21 is carried out using 10% palladium-carbon as a catalyst in a manner similar to that described in Example 17. The oily product is dissolved in ether, and 0.5 ml of hydrogen chloride-ethyl acetate solution (5N) is added dropwise to the solution to give 0.18 g of 3(S)-[1(R)-ethoxycarbonyl-3-cyclohexylpropyl]amino-4-oxo-2,3,4,5-tetrahydro-1,5-benzoxazepine-5-acetic acid hydrochloride as a colorless powder.

Elemental Analysis for $C_{23}H_{32}N_2O_6 \cdot HCl$; Calcd.: C, 58.91; H, 7.09; N, 5.97; Found: C, 58.89; H, 7.23; N, 5.82
$[\alpha]_D^{25} - 134°$ (c=0.5 in methanol)

EXAMPLE 23

Catalytic reduction of benzyl 3(S)-[1(S)-ethoxycarbonyl-3-cyclohexylpropyl]amino-4-oxo-2,3,4,5-tetrahydro-1,5-benzoxazepine-5-acetate (0.35 g) obtained in Example 21 is carried out in a manner similar to that described in Example 17. Ether is added to the oily product to deposit 0.31 g of 3(S)-[1(S)-ethoxycarbonyl-3-cyclohexylpropyl]amino-4-oxo-2,3,4,5-tetrahydro-1,5-benzoxazepine-5-acetic acid as colorless prisms, melting at 135°–139° C.

Elemental Analysis for $C_{23}H_{32}N_2O_6 \cdot \frac{1}{2}H_2O$: Calcd.: C, 62.57; H, 7.53; N, 6.34; Found: C, 62.73; H, 7.38; N, 6.30

$[\alpha]_D^{25} - 128°$ (c=0.5 in methanol)

This product is recrystallized twice from a mixture of ethyl acetate and petroleum ether to give 3(S)-[1(S)-ethoxycarbonyl-3-cyclohexylpropyl]amino-4-oxo-2,3,4,5-tetrahydro-1,5-benzoxazepine-5-acetic acid as colorless prisms, having higher optical purity and melting point of 146°–148° C.

Elemental Analysis for $C_{23}H_{32}N_2O_6$: Calcd.: C, 63.87; H, 7.46; N, 6.48; Found: C, 64.07; H, 7.64; N, 6.45
$[\alpha]_D^{25} - 166°$ (c=0.6 in methanol)

EXAMPLE 24

In 10 ml of N,N-dimethylformamide is dissolved 0.3 g of 3(S)-[1(S)-ethoxycarbonyl-3-phenylpropyl]amino-S4-oxo-2,3,4,5-tetrahydro-1,5-benzoxazepine-5-acetic acid hydrochloride obtained in Example 18, and tert-butyl phenylalaninate (0.3 g) is added to the solution. A solution of 0.13 g of diethyl phosphorocyanidate in N,N-dimethylformamide is added dropwise to the mixture at ice bath temperature. After the resulting mixture is stirred for 10 minutes, a solution of 0.14 g of triethylamine in N,N-dimethylformamide is added dropwise at ice bath temperature and the mixture is stirred for 30 minutes. To the reaction mixture is added 200 ml of ethyl acetate and the resulting mixture is washed successively with 50 ml of water, 50 ml of 0.1N hydrochloric acid (twice), 50 ml of 0.1N sodium hydroxide solution and 50 ml of water. The ethyl acetate layer is dried over anhydrous magnesium sulfate and concentrated under reduced pressure to give 0.4 g of tert-butyl 3(S)-[1(S)-ethoxycarbonyl-3-phenylpropyl]amino-4-oxo-2,3,4,5-tetrahydro-1,5-benzoxazepine-5-yl-N-acetyl-L-phenylalaninate as a colorless oil.

IR $\nu_{max}^{neat}$ cm$^{-1}$: 3350(NH), 1730(ester), 1680, 1690(amide)

EXAMPLE 25

In 100 ml of hydrogen chloride-ethyl acetate (5N) solution is dissolved 0.4 g of tert-butyl 3(S)-[1(S)-ethoxycarbonyl-3-phenylpropyl]amino-4-oxo-2,3,4,5-tetrahydro-1,5-benzoxazepine-5-yl-N-acetyl-L-phenylalaninate obtained in Example 24 and the solution is allowed to stand for 4 hours. The reaction solution is concentrated under reduced pressure, and 50 ml of ether is added to the residue. The resulting mixture is extracted twice with 70 ml each of saturated sodium bicarbonate solution and the aqueous layer is extracted with 50 ml of ether. The aqueous layer is neutralized with 1N hydrochloric acid and extracted with 100 ml of ethyl acetate. The ethyl acetate layer is dried over anhydrous magnesium sulfate and concentrated under reduced pressure. The oily product is dissolved in 10 ml of ether, and 0.5 ml of hydrogen chloride-ethyl acetate (5N) solution is added to the solution to give 0.2 g of 3(S)-[1(S)-ethoxycarbonyl-3-phenylpropyl]amino-4-oxo-2,3,4,5-tetrahydro-1,5-benzoxazepine-5-yl-N-acetyl-L-phenylalanine hydrochloride as a colorless powder.

$[\alpha]_D^{25} - 53.5°$ (c=0.5 in methanol)

Elemental Analysis for $C_{32}H_{35}N_3O_7 \cdot HCl$: Calcd.: C, 63.00; H, 5.95; N, 6.89; Found: C, 62.75; H, 5.93; N, 6.84

EXAMPLE 26

Catalytic reduction of 2.5 g of tert-butyl 3(S)-benzyloxycarbonylamino-4-oxo-2,3,4,5-tetrahydro-1,5-benzoxazepine-5-acetate is carried out in a manner similar to that described in Example 17 to give 1.2 g of tert-butyl 3(S)-amino-4-oxo-2,3,4,5-tetrahydro-1,5-benzoxazepine-5-acetate as a colorless oil.

Elemental Analysis for $C_{15}H_{20}N_2O_4$: Calcd.: C, 61.63; H, 6.90; N, 9.58; Found: C, 61.75; H, 6.91; N, 9.37

Mass spectrum (m/e): 292(M+)

$[\alpha]_D - 253°$ (c=0.9 in methanol)

EXAMPLES 27–34

Benzyl 3(S)-amino-4-oxo-2,3,4,5-tetrahydro-1,5-benzoxazepine-5-acetate hydrochloride obtained in Example 5 is reacted with ethyl pyruvate or α-ketoester obtained in Examples 6–12 in a manner similar to that described in Example 16 to give a compound shown in Table 2 as an oil.

TABLE 2

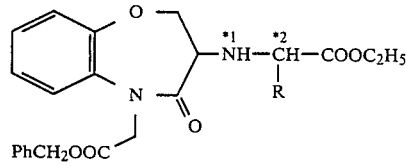

| Ex. No. | R— | config. *1 | config. *2 | Mass spectrum M+(m/e) | IR $\nu_{max}^{neat}$ cm$^{-1}$ |
|---|---|---|---|---|---|
| 27 | CH$_3$— | S | R, S* | 426 | 3330, 1740 1680 |
| 28 | CH$_3$CH$_2$\\CHCH$_2$CH$_2$—/CH$_3$CH$_2$ | S | R | 510 | 3330, 1730 1680 |

TABLE 2-continued

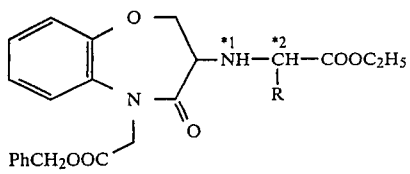

| Ex. No. | R— | config. *1 | config. *2 | Mass spectrum M+(m/e) | IR $\nu_{max}^{neat}$ cm$^{-1}$ |
|---|---|---|---|---|---|
| | CH₃CH₂—CHCH₂CH₂— / CH₃CH₂ | S | S | 510 | 3330, 1740 1670 |
| 29 | (cycloheptyl)—CH₂CH₂— | S | R | 536 | 3320, 1730 1670 |
| | (cycloheptyl)—CH₂CH₂— | S | S | 536 | 3330, 1740 1670 |
| 30 | CH₃—(C₆H₄)—CH₂CH₂— | S | R | 530 | 3330, 1740 1680 |
| | CH₃—(C₆H₄)—CH₂CH₂— | S | S | 530 | 3330, 1740 1680 |
| 31 | (tetrahydropyran-O)—CH₂CH₂— | S | R | 524 | 3330, 1740 1680 |
| | (tetrahydropyran-O)—CH₂CH₂— | S | S | 524 | 3330, 1740 1680 |
| 32 | (tetrahydrothiopyran-S)—CH₂CH₂— | S | R | 540 | 3330, 1740 1680 |
| | (tetrahydrothiopyran-S)—CH₂CH₂— | S | S | 540 | 3330, 1740 1680 |
| 33 | Ph—CH₂OC(O)—N(piperidyl)—CH₂CH₂— | S | R | 657 | 3330, 1740 1690, 1680 |
| | Ph—CH₂OC(O)—N(piperidyl)—CH₂CH₂— | S | S | 657 | 3330, 1740 1690, 1680 |

TABLE 2-continued

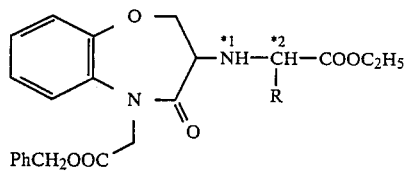

| Ex. No. | R— | config. *1 | *2 | Mass spectrum M+(m/e) | IR $\nu_{max}^{neat}$ cm$^{-1}$ |
|---|---|---|---|---|---|
| 34 | CH$_3$(CH$_2$)$_7$— | S | R, S* | 524 | 3330, 1740, 1680 |

*mixture of diastereomers
In the table, Ph represents phenyl.

EXAMPLE 35

In 10 ml of ethanol is dissolved 0.5 g of benzyl 3(S)-amino-4-oxo-2,3,4,5-tetrahydro-1,5-benzoxazepine-5-acetate hydrochloride obtained in Example 5, and triethylamine (0.49 g) and ethyl bromoacetate (0.46 g) are added to the solution. After the solution is stirred for 4 days, the solution is dried under reduced pressure. The residue is purified by silica gel column chromatography (hexane:ethyl acetate=4:3) to give 0.28 g of benzyl 3(S)-ethoxycarbonylmethylamino-4-oxo-2,3,4,5-tetrahydro-1,5-benzoxazepine-5-acetate as a pale yellow oil.

IR $\nu_{max}^{neat}$ cm$^{-1}$: 3330(NH), 1740, 1680(C=O)
Mass spectrum (m/e): 412(M+)
$[\alpha]_D$ —148° (c=0.4 in methanol)

EXAMPLE 36-48

Catalytic reduction of benzyl 1,5-benzoxazepine-5-acetate derivative obtained in Examples 27–35 is carried out using 10% palladium-carbon as a catalyst in a manner similar to that described in Example 17 to give 1,5-benzoxazepine-5-acetic acid derivative shown in Table 3.

TABLE 3

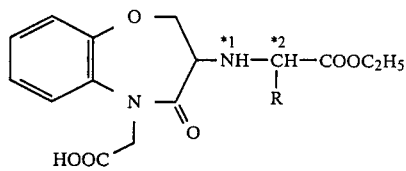

| Ex. No. | R | config. *1 | *2 | Composition formula | Elemental analysis C calcd. (Found) | H calcd. (Found) | N calcd. (Found) | Mass spectrum (m/e)M+ |
|---|---|---|---|---|---|---|---|---|
| 36 | CH$_3$— | S | S,R* | C$_{16}$H$_{20}$N$_2$O$_6$ HCl.½H$_2$O | 50.33 (50.11) | 5.80 (5.72) | 7.34 (7.32) | 336 |
| 37 | CH$_3$CH$_2$\CHCH$_2$CH$_2$—/CH$_3$CH$_2$ | S | R | C$_{22}$H$_{32}$N$_2$O$_6$ HCl.½H$_2$O | 56.70 (56.64) | 7.35 (7.34) | 6.01 (5.97) | 420 |
| 38 | CH$_3$CH$_2$\CHCH$_2$CH$_2$—/CH$_3$CH$_2$ | S | S | C$_{22}$H$_{32}$N$_2$O$_6$ HCl.½H$_2$O | 56.70 (56.81) | 7.35 (7.28) | 6.01 (6.00) | 420 |
| 39 | cyclohexyl-CH$_2$CH$_2$ | S | R | C$_{24}$H$_{34}$N$_2$O$_6$ HCl.½H$_2$O | 58.59 (58.43) | 7.38 (7.40) | 5.69 (5.60) | 446 |
| 40 | cyclohexyl-CH$_2$CH$_2$— | S | S | C$_{24}$H$_{34}$N$_2$O$_6$ HCl.½H$_2$O | 58.59 (58.29) | 7.38 (7.41) | 5.69 (5.58) | 446 |

TABLE 3-continued

Structure: benzoxazepine with NH—*1CH(R)—COOC2H5 side chain, N-CH2-COOH on ring nitrogen.

| Ex. No. | R | config. *1 | config. *2 | Composition formula | C calcd. (Found) | H calcd. (Found) | N calcd. (Found) | Mass spectrum (m/e)M+ |
|---|---|---|---|---|---|---|---|---|
| 41 | CH3—C6H4—CH2CH2— | S | S | C23H28N2O6·HCl·½H2O | 59.32 (59.29) | 6.22 (6.35) | 5.76 (5.72) | 440 |
| 42 | O-containing ring—CH2CH2— | S | R | C22H30N2O7·HCl·½H2O | 55.06 (55.11) | 6.72 (6.78) | 5.84 (5.38) | 434 |
| 43 | O-containing ring—CH2CH2— | S | S | C22H30N2O7·HCl·½H2O | 55.06 (54.73) | 6.72 (6.66) | 5.84 (5.71) | 434 |
| 44 | S-containing ring—CH2CH2— | S | R | C22H30N2O6S·HCl·½H2O | 53.27 (53.32) | 6.50 (6.47) | 5.65 (5.59) | 450 |
| 45 | S-containing ring—CH2CH2— | S | S | C22H30N2O6S·HCl·½H2O | 53.27 (53.15) | 6.50 (6.20) | 5.65 (5.77) | 450 |
| 46 | HN-containing ring—CH2CH2— | S | S | C22H31N3O6·2HCl·H2O | 50.39 (50.36) | 6.73 (6.68) | 8.01 (7.56) | 433** |
| 47 | CH3(CH2)7— | S | R,S* | C23H34N2O6·HCl·½H2O | 57.55 (57.60) | 7.56 (7.50) | 5.84 (5.93) | 434 |
| 48 | H | S | — | C15H18N2O6 | 55.90 (55.47) | 5.63 (5.62) | 8.69 (8.28) | 322 |

*mixture of diastereomers
**free base is used for measurement.

EXAMPLE 49

Reaction of 9.5 g of tert-butyl 3(S)-amino-4-oxo-2,3,4,5-tetrahydro-1,5-benzoxazepine-5-acetate obtained in Example 26 and ethyl 4-cyclohexyl-2-oxobutyrate is carried out under reductive conditions in a manner similar to that described in Example 16, and the product is purified by silica gel column chromatography (hexane:ethyl acetate=5:1). From the first fraction, 2.3 g of tert-butyl 3(S)-[1(R)-ethoxycarbonyl-3-cyclohexylpropyl]amino-4-oxo-2,3,4,5-tetrahydro-1,5-benzoxazepine-5-acetate is obtained as a colorless oil.

Elemental Analysis for $C_{27}H_{40}N_2O_6$: Calcd.: C, 66.37; H, 8.25; N, 5.73; Found: C, 66.57; H, 8.57; N, 5.48
Mass spectrum (m/e): 488 (M+)
$[\alpha]_D - 112°$ (c=0.5 in methanol)

From the second fraction, 3.2 g of tert-butyl 3(S)-[1(S)-ethoxycarbonyl-3-cyclohexylpropyl]amino-4-oxo-2,3,4,5-tetrahydro-1,5-benzoxazepine-5-acetate is obtained as a colorless oil.

Elemental Analysis for $C_{27}H_{40}N_2O_6$: Calcd.: C, 66.37; H, 8.25; N, 5.73; Found: C, 66.72; H, 8.72; N, 5.82
Mass spectrum (m/e): 488 (M+)
$[\alpha]_D - 125°$ (c=0.4 in methanol)

EXAMPLE 50

In 10 ml of ethanol is dissolved 1.5 g of tert-butyl 3(S)-[1(S)-ethoxycarbonyl-3-cyclohexylpropyl]amino-4-oxo-2,3,4,5-tetrahydro-1,5-benzoxazepine-5-acetate obtained in Example 49, and 1N sodium hydroxide solution is added dropwise over a period of 15 minutes. After stirring for 3 hours, the solution is diluted with water (200 ml) and extracted with ethyl ether (100 ml). The aqueous layer is acidified slightly with 1N hydrochloric acid to deposit crystals. This product is collected by filtration and dried to give 1.2 g of tert-butyl 3(S)-[1(S)-carboxy-3-cyclohexylpropyl]amino-4-oxo-2,3,4,5-tetrahydro-1,5-benzoxazepine-5-acetate as colorless needles, melting at 180°-183° C.

Elemental Analysis for $C_{25}H_{36}N_2O_6$: Calcd.: C, 65.20; H, 7.88; N, 6.08; Found: C, 65.18; H, 7.83; N, 6.14
$[\alpha]_D -122°$ (c=0.5 in methanol)

EXAMPLE 51

In 10 ml of N,N-dimethylformamide is dissolved 0.25 g of tert-butyl 3(S)-[1(S)-carboxy-3-cyclohexylpropyl]amino-4-oxo-2,3,4,5-tetrahydro-1,5-benzoxazepine-5-acetate obtained in Example 50, and benzyl bromide (0.14 g), sodium bicarbonate (0.7 g) and potassium iodide (0.05 g) are added to the solution. The reaction solution is stirred at room temperature for 6 hours and diluted with water (100 ml) and extracted with ethyl acetate. The extract is washed successively with 1N hydrochloric acid and water, dried over anhydrous magnesium sulfate and concentrated under reduced pressure. The oily product is purified by silica gel column chromatography (hexane:ethyl acetate=5:1) to give 0.25 g of tert-butyl 3(S)-[1(S)-benzyloxycarbonyl-3-cyclohexylpropyl]amino-4-oxo-2,3,4,5-tetrahydro-1,5-benzoxazepine-5-acetate as a colorless oil.

IR $\nu_{max}^{neat}$ cm$^{-1}$: 3330(NH), 1740, 1680 (C=O)
$[\alpha]_D -155°$ (c=0.6 in methanol)
Mass spectrum (m/e): 550(M+)

EXAMPLES 52-53

Reaction of tert-butyl 3(S)-[1(S)-carboxy-3-cyclohexylpropyl]amino-4-oxo-2,3,4,5-tetrahydro-1,5-benzoxazepine-5-acetate and halide shown in Table 4 is carried out in a manner similar to that of described in Example 51 to give a benzoxazepine derivative shown in Table 4.

TABLE 4

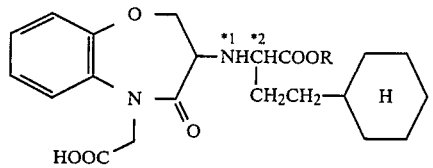

| Ex. No. | Halogenated compound used | R | Config *1 | *2 | $[\alpha]_D$ (in methanol) |
|---|---|---|---|---|---|
| 52 | BrCH$_2$COOC$_2$H$_5$ | —CH$_2$COOC$_2$H$_5$ | S | S | −145° (C = 0.7) |
| 53 | I(CH$_2$)$_3$CH$_3$ | —(CH$_2$)$_3$CH$_3$ | S | S | −200° (C = 0.5) |

EXAMPLE 54

In 10 ml of 5N hydrogen chloride-ethyl acetate solution is dissolved 0.5 g of tert-butyl 3(S)-[1(S)-ethoxycarbonyl-3-cyclohexylpropyl]amino-4-oxo-2,3,4,5-tetrahydro-1,5-benzoxazepine-5-acetate obtained in Example 49, and the solution is allowed to stand at room temperature for 4 hours. To the solution is added 200 ml of petroleum ether and the resulting mixture is shaken thoroughly. After the supernatant is removed by decantation, the residue is diluted with 50 ml of water and extracted three times with 100 ml each of ethyl acetate. The extract is washed with water, dried over anhydrous magnesium sulfate and concentrated under reduced pressure. Ethyl ether is added to the viscous residue to give 0.37 g of 3(S)-[1(S)-ethoxycarbonyl-3-cyclohexylpropyl]amino-4-oxo-2,3,4,5-tetrahydro-1,5-benzoxazepine-5-acetic acid as colorless crystals melting at 135°–139° C.

$[\alpha]_D -144°$ (c=0.3 in methanol)

This product is recrystallized from ethyl acetate and petroleum ether to give 3(S)-[1(S)-ethoxycarbonyl-3-cyclohexylpropyl]amino-4-oxo-2,3,4,5-tetrahydro-1,5-benzoxazepine-5-acetic acid as colorless prisms, which is identical with the compound obtained by recrystallization in Example 23.

EXAMPLES 55-57

Benzoxazepine-5-acetic acid tert-butyl ester derivatives obtained in Examples 51 to 53 are treated with hydrogen chloride in a manner similar to that described in Example 54 to give benzoxazepine-5-acetic acid derivatives shown in Table 5.

TABLE 5

| Ex. No. | R | Config *1 | *2 | $[\alpha]_D$ (in methanol) |
|---|---|---|---|---|
| 55 | —CH$_2$—C$_6$H$_5$ | S | S | −115° C = 0.5 |
| 56 | —CH$_2$COOC$_2$H$_5$ | S | S | −114° C = 0.6 |
| 57 | —(CH$_2$)$_3$CH$_3$ | S | S | −106° C = 0.4 |

EXAMPLE 58

In 1 ml of ethanol is dissolved 0.2 g of 3(S)-[1(S)-ethoxycarbonyl-3-cyclohexylpropyl]amino-4-oxo-2,3,4,5-tetrahydro-1,5-benzoxazepine-5-acetic acid obtained in Example 54, and 3 ml of 1N sodium hydroxide solution is added to the solution. After stirring at room temperature for 2 hours, the solution is acidified slightly with 1N hydrochloric acid. The deposited crystals are collected by filtration, washed with water, dried and recrystallized from ethanol to give 0.14 g of 3(S)-[1(S)-carboxy-3-cyclohexylpropyl]amino-4-oxo-2,3,4,5-tetrahydro-1,5-benzoxazepine-5-acetic acid as colorless crystals, melting at 202°–205° C.

Elemental Analysis for $C_{21}H_{28}N_2O_6 \cdot H_2O$: Calcd.: C, 59.70; H, 7.16; N, 6.63; Found: C, 59.81; H, 7.03; N, 6.68
$[\alpha]_D -131°$ (c=0.4 in methanol)

EXAMPLE 59

In 5 ml of 1N sodium hydroxide solution is dissolved 0.2 g of 3(S)-[1(S)-ethoxycarbonyl-3-(3,4,5,6-tetrahydro-2H-pyran-4-yl)propyl]amino-4-oxo-2,3,4,5-tetrahydro-1,5-benzoxazepine-5-acetic acid hydrochloride obtained in Example 43, and the solution is allowed to stand at room temperature for 1 hours. The solution is neutralized with 1.5 ml of acetic acid and purified by Amberlite XAD-2 column chromatography (acetone:water=1:1). The eluate is concentrated under reduced pressure and lyophilized to give 0.16 g of 3(S)-[1(S)-carboxy-3-(3,4,5,6-tetrahydro-2H-pyran-4-yl)propyl]amino-4-oxo-2,3,4,5-tetrahydro-1,5-benzoxazepine-5-acetic acid as a colorless powder.

Elemental Analysis for $C_{20}H_{26}N_2O_7 \cdot \frac{1}{2}H_2O$: Calcd.: C, 57.82; H, 6.55; N, 6.74; Found: C, 57.41; H, 6.01; N, 6.36

$[\alpha]_D - 128°$ (c=0.4 in methanol)

EXAMPLE 60

3(S)-[1(S)-Ethoxycarbonyl-3-(4-piperidyl)propyl]amino-4-oxo-2,3,4,5-tetrahydro-1,5-benzoxazepine-5-acetic acid obtained in Example 46 is subjected to hydrolysis in a manner similar to that described in Example 59, purified and lyophilized to give 3(S)-[1(S)-carboxy-3-(4-piperidyl)propyl]amino-4-oxo-2,3,4,5-tetrahydro-1,5-benzoxazepine-5-acetic acid as a colorless powder.

$[\alpha]_D - 132°$ (c=0.6 in methanol)
SIMS spectrum (m/e): 406 (MH+)

EXAMPLE 61

3(S)-[1(S)-Ethoxycarbonyl-3-(4-thianyl)propyl]amino-4-oxo-2,3,4,5-tetrahydro-1,5-benzoxazepine-5-acetic acid hydrochloride obtained in Example 45 is subjected to hydrolysis in a manner similar to that described in Example 60 and purified by Amberlite XAD-2 column chromatography. The eluate is concentrated under reduced pressure to give 3(S)-[1(S)-carboxy-3-(4-thianyl)propyl]amino-4-oxo-2,3,4,5-tetrahydro-1,5-benzoxazepine-5-acetic acid as crystals.

Elemental Analysis for $C_{20}H_{26}N_2O_6S \cdot H_2O$: Calcd.: C, 54.53; H, 6.41; N, 6.36; Found: C, 54.12; H, 6.32; N, 6.30

EXAMPLE 62

In 150 ml of acetonitrile are dissolved 5 g of benzyl 3(S)-amino-4-oxo-2,3,4,5-tetrahydro-1,5-benzoxazepine-5-acetate hydrochloride and 13 g of ethyl 2-bromo-5-phthalimidohexanoate, and 3.2 g of triethylamine is added to the solution. After heating at 80° C. for 4 days, the solution is concentrated under reduced pressure and diluted with 100 ml of water and extracted with 150 ml of ethyl acetate. The ethyl acetate layer is dried over anhydrous magnesium sulfate and concentrated under reduced pressure. Ethyl acetate (15 ml) and oxalic acid (3 g) is added to the residue. Petroleum ether (200 ml) is added to the solution and the resulting mixture is shaken. After standing, the supernatant is removed by decantation and 100 ml of water and 150 ml of ethyl acetate are added to the precipitate. The resulting mixture is neutralized with sodium bicarbonate and the ethyl acetate layer is dried over anhydrous magnesium sulfate and concentrated under reduced pressure. The resulting oil is separated and purified by silica gel column chromatography (hexane:ethyl acetate=2:1–3:2) to give firstly 2.3 g of benzyl 3(S)-[1(R)-ethoxycarbonyl-5-phthalimidopentyl]amino-4-oxo-2,3,4,5-tetrahydro-1,5-benzoxazepine-5-acetate as a colorless oil.

IR $\nu_{max}^{neat}$ cm$^{-1}$: 3330(NH), 1770, 1740, 1720, 1680 (C=O)

$[\alpha]_D - 104°$ (in methanol)

From the succeeding fraction, benzyl 3(S)-[1(S)-ethoxycarbonyl-5-phthalimidopentyl]amino-4-oxo-2,3,4,5-tetrahydro-1,5-benzoxazepine-5-acetate as a colorless oil.

IR $\nu_{max}^{neat}$ cm$^{-1}$: 3330(NH), 1760, 1710, 1680(C=O)
$[\alpha]_D - 100°$ (in methanol)

EXAMPLE 63

In 20 ml of ethanol is dissolved 0.15 g of benzyl 3(S)-[1(S)-ethoxycarbonyl-5-phthalimidopentyl]amino-4-oxo-2,3,4,5-tetrahydro-1,5-benzoxazepine-5-acetate obtained in Example 62 and catalytic reduction is carried out at ordinary temperature and under atmospheric pressure using 0.1 g of 10% palladium-carbon as a catalyst. After the absorption of hydrogen stops, the catalyst is filtered off and the filtrate is concentrated under reduced pressure. The oily product is dissolved in 3 ml of ethyl ether, and 0.5 ml of hydrogen chloride-ethyl acetate solution (5N) to the solution to give 0.12 g of 3(S)-[1(S)-ethoxycarbonyl-5-phthalimidopentyl]amino-4-oxo-2,3,4,5-tetrahydro-1,5-benzoxazepine-5-acetic acid hydrochloride as a colorless powder.

Elemental Analysis for $C_{26}H_{29}N_3O_8 \cdot HCl \cdot \frac{1}{2}H_2O$: Calcd.: C, 56.07; H, 5.61; N, 7.54; Found: C, 56.19; H, 5.31; N, 7.44

$[\alpha]_D - 104°$ (in methanol)

EXAMPLE 64

In 100 ml of acetonitrile are dissolved 2.8 g of tert-butyl 3(S)-amino-4-oxo-2,3,4,5-tetrahydro-1,5-benzoxazepine-5-acetate and 7.6 g of ethyl 2-bromo-8-phthalimidooctanoate, and 1.3 g of triethylamine is added to the solution. After heating at 80° C. for 3 days, the reaction solution is concentrated under reduced pressure, diluted with 200 ml of water and extracted with 200 ml of ethyl acetate. The ethyl acetate layer is dried over anhydrous magnesium sulfate and concentrated under reduced pressure. Ethyl acetate (10 ml) and oxalic acid (2.8 g) are added to the residue, and 200 ml of petroleum ether is added to the solution. After shaking, the resulting solution is allowed to stand. The supernatant is removed by decantation and 150 ml of water and 200 ml of ethyl acetate are added to the precipitate. The mixture is neutralized with sodium bicarbonate and the ethyl acetate layer is dried over anhydrous magnesium sulfate and concentrated under reduced pressure. The oily product is separated and purified by silica gel column chromatography to give 1.5 g of tert-butyl 3(S)-[1(R)-ethoxycarbonyl-7-phthalimidoheptyl]amino-4-oxo-2,3,4,5-tetrahydro-1,5-benzoxazepine-5-acetate from the first fraction.

IR $\nu_{max}^{neat}$ cm$^{-1}$: 3340(NH), 1770, 1740, 1710, 1670 (C=O)

$[\alpha]_D - 104°$ (in methanol)

From the second fraction, 1.7 g of tert-butyl 3(S)-[1(S)-ethoxycarbonyl-7-phthalimidoheptyl]amino-4-oxo-2,3,4,5-tetrahydro-1,5-benzoxazepine-5-acetate is obtained.

IR $\nu_{max}^{neat}$ cm$^{-1}$: 3340(NH), 1775, 1740, 1720, 1680(C=O)

$[\alpha]_D - 115°$ (in methanol)

EXAMPLE 65

In 5 ml of 5N hydrogen chloride-ethyl acetate solution is dissolved 0.12 g of tert-butyl 3(S)-[1(R)-ethoxycarbonyl-7-phthalimidoheptyl]amino-4-oxo-2,3,4,5-tetrahydro-1,5-benzoxazepine-5-acetate obtained in Example 64, and the solution is allowed to stand at room temperature for 3 hours. Petroleum ether (100 ml) is added to the solution and the deposited precipitate is dried under reduced pressure to give 0.08 g of 3(S)-[1(R)-ethoxycarbonyl-7-phthalimidoheptyl]amino-4-oxo-2,3,4,5-tetrahydro-1,5-benzoxazepine-5-acetic acid hydrochloride as a colorless powder.

$[\alpha]_D - 128°$ (in methanol)
Elemental Analysis for $C_{29}H_{33}N_3O_8 \cdot HCl \cdot \frac{1}{2}H_2O$: Calcd.: C, 58.34; H, 5.90; N, 7.03; Found: C, 58.25; H, 5.75; N, 7.08

EXAMPLE 66

In 5 ml of 5N hydrogen chloride-ethyl acetate solution is dissolved 0.11 g of tert-butyl 3(S)-[1(S)-ethoxycarbonyl-7-phthalimidoheptyl]amino-4-oxo-2,3,4,5-tetrahydro-1,5-benzoxazepine-5-acetate obtained in Example 64, and the solution is allowed to stand at room temperature for 3 hours. Petroleum ether (100 ml) is added to the solution and the deposited precipitate is dried under reduced pressure to give 0.095 g of 3(S)-[1(S)-ethoxycarbonyl-7-phthalimidoheptyl]amino-4-oxo-2,3,4,5-tetrahydro-1,5-benzoxazepine-5-acetic acid hydrochloride as a colorless powder.

Elemental Analysis for $C_{29}H_{33}N_3O_8 \cdot HCl \cdot \frac{1}{2}H_2O$: Calcd.: C, 58.34; H, 5.90; N, 7.03; Found: C, 58.43; H, 6.02; N, 6.80

$[\alpha]_D$ −104° (in methanol)

EXAMPLE 67

In 10 ml of ethanol is dissolved 0.7 g of tert-butyl 3(S)-[1(S)-ethoxycarbonyl-7-phthalimidoheptyl]amino-4-oxo-2,3,4,5-tetrahydro-1,5-benzoxazepine-5-acetate obtained in Example 64, and hydrazine hydrate (0.29 g) is added to the solution. After standing overnight, the solution is concentrated under reduced pressure, diluted with 50 ml of water and extracted five times with 30 ml each of ethyl acetate. To the ethyl acetate layer are added 50 ml of water and 0.7 g of sodium bicarbonate and 0.38 g of di-tert-butyl dicarbonate is added dropwise to the resulting mixture with stirring. After the mixture is stirring at room temperature for 0.5 hour, the ethyl acetate layer is dried over anhydrous magnesium sulfate and concentrated under reduced pressure. The residue is purified by silica gel column chromatography (hexane:ethyl acetate=2:1) to give 0.51 g of tert-butyl 3(S)-[7-tert-butoxycarbonylamino-1(S)-ethoxycarbonylheptyl]amino-4-oxo-2,3,4,5-tetrahydro-1,5-benzoxazepine-5-acetate as a colorless oil.

IR $\nu_{max}^{neat}$ cm$^{-1}$: 1740, 1710, 1680(C=O)

$[\alpha]_D$ −122° (in methanol)

EXAMPLE 68

In 10 ml of 5N hydrogen chloride-ethyl acetate solution is dissolved 1.1 g of tert-butyl 3(S)-[7-tert-butoxycarbonylamino-1(S)-ethoxycarbonylheptyl]amino-4-oxo-2,3,4,5-tetrahydro-1,5-benzoxazepine-5-acetate obtained in Example 67 and the solution is allowed to stand at room temperature for 3 hours. Petroleum ether (100 ml) is added to the solution and the deposited precipitate is dried under reduced pressure to give 0.9 g of 3(S)-[7-amino-1(S)-ethoxycarbonylheptyl]amino-4-oxo-2,3,4,5-tetrahydro-1,5-benzoxazepine-5-acetic acid dihydrochloride as a colorless powder.

$[\alpha]_D$ −108° (in methanol)

EXAMPLE 69

In 15 ml of 1N sodium hydroxide solution is dissolved 0.5 g of 3(S)-[7-amino-1(S)-ethoxycarbonylheptyl]amino-4-oxo-2,3,4,5-tetrahydro-1,5-benzoxazepine-5-acetic acid dihydrochloride obtained in Example 68, and the solution is allowed to stand at room temperature for 30 minutes. Acetic acid (3.5 ml) is added to the solution and the mixture is purified by Amberlite XAD-2 column chromatography (methanol:water=1:2). The eluate is concentrated under reduced pressure and lyophilized to give 0.31 g of 3(S)-[7-amino-1(S)-carboxyheptyl]amino-4-oxo-2,3,4,5-tetrahydro-1,5-benzoxazepine-5-acetic acid as a colorless powder.

$[\alpha]_D$ −159° (in methanol)

SIMS spectrum (m/e): 394(MH+)

EXAMPLE 70

A mixture of tert-butyl 3(S)-amino-4-oxo-2,3,4,5-tetrahydro-1,5-benzoxazepine-5-acetate (2 g), ethyl 2-bromo-7-phthalimidoheptanoate (3.9 g), acetonitrile (100 ml) and triethylamine (0.9 g) is heated at 80° C. for 3 days. After evaporation of acetonitrile, water (150 ml) and ethyl acetate (200 ml) is added to the residue, and the mixture is agitated thoroughly. The ethyl acetate layer is dried over anhydrous magnesium sulfate and concentrated in vacuo. The oily residue is dissolved in a mixture of ethyl acetate (10 ml) and oxalic acid (2 g). The resulting solution is diluted with petroleum ether (200 ml) and agitated thoroughly. The supernatant layer is removed by decantation. To the precipitate are added water (150 ml), ethyl acetate (200 ml) and sodium bicarbonate with stirring. The ethyl acetate layer is separated, dried over anhydrous magnesium sulfate and concentrated in vacuo. The oily residue is chromatographed on silica gel using hexane-ethyl acetate (2:1–1:1) as an eluent. Evaporation of the first fraction affords tert-butyl 3(S)-[1(R)ethoxycarbonyl-6-phthalimidohexyl[amino-4-oxo-2,3,4,5-tetrahydro-1,5-benzoxazepine-5-acetate (0.65 g) as a colorless oil.

IR $\nu_{max}^{neat}$ cm$^{-1}$: 3330(NH); 1770, 1740, 1710, 1680 (C=O)

$[\alpha]_D$ −110° (in methanol).

Mass spectrum (m/e): 593(M+)

Evaporation of the second fraction gives tert-butyl 3(S)-[1(S)-ethoxycarbonyl-6-phthaliminohexyl]amino-4-oxo-2,3,4,5-tetrahydro-1,5-benzoxazepine-5-acetate (0.75 g) as a colorless oil.

IR $\nu_{max}^{neat}$ cm$^{-1}$: 3320(NH):; 1770, 1740, 1710, 1670(C=O)

$[\alpha]_D$ −123° (in methanol)

Mass spectrum (m/e): 593(M+)

EXAMPLE 71

A mixture of 5N hydrogen chloride-ethyl acetate solution (5 ml) and tert-butyl 3(S)-[1(S)-ethoxycarbonyl-6-phthalimidohexyl]amino-4-oxo-2,3,4,5-tetrahydro-1,5-benzoxazepine-5-acetate (0.1 g) is allowed to stand at room temperature for 3 hours. The mixture is diluted with petroleum ether (80 ml) to precipitate colorless powder, which is collected and dried in vacuo to give 3(S)-[1(S)-ethoxycarbonyl-6-phthalimidohexyl]amino-4-oxo-2,3,4,5-tetrahydro-1,5-benzoxazepine-5-acetic acid hydrochloride (0.08 g).

$[\alpha]_D$ −108° (in methanol)

Elemental Analysis for $C_{28}H_{31}N_3O_8 \cdot HCl \cdot \frac{1}{2}H_2O$: Calcd.: C, 57.68; H, 5.53; N, 7.21; Found: C, 57.65; H, 5.65; N, 7.13

EXAMPLE 72

A mixture of tert-butyl 3(S)-[1(S)-ethoxycarbonyl-6-phthalimidohexyl]amino-4-oxo-2,3,4,5-tetrahydro-1,5-benzoxazepine-5-acetate (0.65 g), hydrazine hydrate (0.27 g) and ethanol (10 ml) is allowed to stand overnight at room temperature. The mixture is concentrated in vacuo, diluted with water (50 ml) and extracted with ethyl acetate (50 ml×4). To a mixture of the organic extract, water (50 ml) and sodium bicarbonate (0.65 g) are added dropwise di-tert-butyl dicarbonate (0.36 g) with stirring at room temperature. After stirring for 30 minutes, the ethyl acetate layer is separated, dried over anhydrous magnesium sulfate and concentrated in vacuo. The residue is subjected to silica gel column chromatography using hexane:ethyl acetate (2:1–1:1) as an eluent to yield tert-butyl 3(S)-[6-tert-butoxycarbonylamino-1(S)-ethoxycarbonylhexyl]amino-4-oxo-2,3,4,5-tetrahydro-1,5-benzoxazepine-5-acetate (0.54 g) as a colorless oil.

IR $\nu_{max}^{neat}$ cm$^{-1}$: 1740, 1720, 1680(C=O)
$[\alpha]_D$ −128° (in methanol)
Mass spectrum (m/e): 563(M+)

EXAMPLE 73

A solution of tert-butyl 3(S)-[6-tert-butoxy-carbonylamino-1(S)-ethoxycarbonylhexyl]amino-4-oxo-2,3,4,5-tetrahydro-1,5-benzoxazepine-5-acetate (0.5 g) in 5N hydrogen chloride-ethyl acetate solution (10 ml) is allowed to stand for 3.5 hours at room temperature. Petroleum ether (80 ml) is added to the solution, and the resulting precipitate is collected and dried in vacuo to give 3(S)-[6-amino-1(S)-ethoxycarbonylhexyl]amino-4-oxo-2,3,4,5-tetrahydro-1,5-benzoxazepine-5-acetic acid dihydrochloride (0.4 g) as colorless powder.

$[\alpha]_D$ −118° (in methanol)
Mass spectrum (m/e): 407(M+)

EXAMPLE 74

A solution of 3(S)-[6-amino-1(S)-ethoxycarbonylhexyl]amino-4-oxo-2,3,4,5-tetrahydro-1,5-benzoxazepine-5-acetic acid dihydrochloride (0.35 g) in 1N sodium hydroxide solution (10 ml) is allowed to stand for 30 minutes at room temperature. After addition of acetic acid (2.5 ml), the mixture is subjected to Amberlite XAD-2 column chromatography eluting with methanol-water (1:10). The eluate is concentrated under reduced pressure and lyophilized to yield 3(S)-[6-amino-1(S)-carboxyhexyl]amino-4-oxo-2,3,4,5-tetrahydro-1,5-benzoxazepine-5-acetic acid (0.17 g) as colorless powder.

$[\alpha]_D$ −157° (in methanol)
SIMS spectrum (m/e): 380(MH+)

EXAMPLE 75

A mixture of tert-butyl 3(S)-amino-4-oxo-2,3,4,5-tetrahydro-1,5-benzoxazepine-5-acetate (2.1 g), ethyl 2-bromo-9-phthalimidononanoate (3 g), acetonitrile (100 ml) and triethylamine (0.96 g) is heated at 80° C. for 3 days. After evaporation of the solvent, ethyl acetate (200 ml) and water (150 ml) are added to the residue. The ethyl acetate layer is separated, dried over anhydrous magnesium sulfate and evaporated in vacuo. The oily residue is chromatographed on silica gel using hexane-ethyl acetate (2:1–1:1) as an eluent. Evaporation of the first eluate gives tert-butyl 3(S)-[1(R)-ethoxycarbonyl-8-phthalimidooctyl]amino-4-oxo-2,3,4,5-tetrahydro-1,5-benzoxazepine-5-acetate (0.6 g) as a colorless oil.

IR $\nu_{max}^{neat}$ cm$^{-1}$: 3330(NH); 1770, 1740, 1710, 1680(C=O)
$[\alpha]_D$ −106° (in methanol)

From the second eluate is obtained tert-butyl 3(S)-[1(S)-ethoxycarbonyl-8-phthalimido-octyl]amino-4-oxo-2,3,4,5-tetrahydro-1,5-benzoxazepine-5-acetate (0.65 g) as a colorless oil.

IR $\nu_{max}^{neat}$ cm$^{-1}$: 3320(NH); 1770, 1740, 1710, 1680(C=O)
$[\alpha]_D$ −110° (in methanol)
Mass spectrum (m/e): 621(M+)

EXAMPLE 76

A mixture of 5N hydrogen chloride-ethyl acetate solution (5 ml) and tert-butyl 3(S)-[1(S)-ethoxycarbonyl-8-phthalimidooctyl]amino-4-oxo-2,3,4,5-tetrahydro-1,5-benzoxazepine-5-acetate (0.1 g) is allowed to stand at room temperature for 3 hours. The mixture is diluted with petroleum ether (80 ml) to precipitate colorless powder, which is collected and dried in vacuo to give 3(S)-[1(S)-ethoxycarbonyl-8-phthalimidooctyl]amino-4-oxo-2,3,4,5-tetrahydro-1,5-benzoxazepine-5-acetic acid.hydrochloride (0.067 g).

$[\alpha]_D$ −100° (in methanol)
Elemental analysis for $C_{30}H_{35}N_3O_8 \cdot HCl \cdot \frac{1}{2}H_2O$: Calcd.: C, 58.97; H, 6.10; N, 6.88; Found: C, 59.10; H, 6.26; N, 6.72

EXAMPLE 77

A mixture of tert-butyl 3(S)-[1(S)-ethoxycarbonyl-8-phthalimidooctyl]amino-4-oxo-2,3,4,5-tetrahydro-1,5-benzoxazepine-5-acetate (0.55 g), hydrazine hydrate (0.22 g) and ethanol (10 ml) is allowed to stand overnight at room temperature. After evaporation of ethanol, the residue is dissolved in water (50 ml) and extracted with ethyl acetate (50 ml×4). Water (50 ml) and sodium bicarbonate (0.6 g) are added to the organic extract, and to the resulting mixture is added dropwise di-tert-butyl dicarbonate (0.29 g) with stirring. After stirring for 30 minutes at room temperature, the ethyl acetate layer is separated, dried over anhydrous magnesium sulfate and concentrated in vacuo. The residue is purified by silica gel column chromatography using hexane:ethyl acetate (2:1–1:1) as an eluent to give tert-butyl 3(S)-[8-tert-butoxycarbonylamino-1(S)-ethoxycarbonyloctyl]amino-4-oxo-2,3,4,5-tetrahydro-1,5-benzoxazepine-5-acetate (0.48 g) as a colorless oil.

IR $\nu_{max}^{neat}$ cm$^{-1}$: 1740, 1720, 1680 (C=O)
$[\alpha]_D$ −102° (in methanol)
Mass spectrum (m/e): 591 (M+)

EXAMPLE 78

A mixture of tert-butyl 3(S)-[8-tert-butoxycarbonylamino-1(S)-ethoxycarbonyloctyl]amino-4-oxo-2,3,4,5-tetrahydro-1,5-benzoxazepine-5-acetate (0.45 g) and 5N hydrogen chloride-ethyl acetate solution (10 ml) is allowed to stand for 3.5 hours at room temperature. The mixture is diluted with petroleum ether (80 ml) to precipitate colorless powder, which is collected and dried in vacuo to give 3(S)-[8-amino-1(S)-ethoxycarbonyloctyl]amino-4-oxo-2,3,4,5-tetrahydro-1,5-benzoxazepine-5-acetic acid.dihydrochloride (0.37 g).

$[\alpha]_D$ −114° (in methanol)
Mass spectrum (m/e): 435(M+)

EXAMPLE 79

A solution of 3(S)-[8-amino-1(S)-ethoxycarbonyloctyl]amino-4-oxo-2,3,4,5-tetrahydro-1,5-benzoxazepine-5-acetic acid.dihydrochloride (0.3 g) in 1N sodium hydroxide solution (10 ml) is allowed to stand for 30 minutes at room temperature. After addition of acetic acid (2.5 ml), the mixture is subjected to Amberlite XAD-2 column chromatography eluting with methanol-water (1:2). The eluate is concentrated under reduced pressure and lyophilized to yield 3(S)-[8-amino-1(S)-carboxyoctyl]amino-4-oxo-2,3,4,5-tetrahydro-1,5-benzoxazepine-5-acetic acid (0.2 g) as colorless powder.

Elemental analysis for $C_{20}H_{29}N_3O_6 \cdot H_2O$: Calcd.: C, 56.46; H, 7.34; N, 9.87; Found: C, 56.61; H, 6.86; N, 9.85

[α]$_D$ −147° (in methanol)
SIMS spectrum (m/e): 408(MH+)

EXAMPLE 80

A mixture of tert-butyl 3(S)-amino-4-oxo-2,3,4,5-tetrahydro-1,5-benzoxazepine-5-acetate (1.65 g), ethyl 2-bromo-10-phthalimidodecanoate (2.4 g), acetonitrile (100 ml) and triethylamine (0.75 g) is heated at 80° C. for 4 days. After evaporation of the solvent, ethyl acetate (200 ml) and water (100 ml) are added to the residue. The ethyl acetate layer is dried over anhydrous magnesium sulfate and evaporated in vacuo. The oily residue is chromatographed on silica gel using hexane-ethyl acetate (2:1) as an eluent. Evaporation of the first fraction gives tert-butyl 3(S)-[1(R)-ethoxycarbonyl-9-phthalimidononyl]amino-4-oxo-2,3,4,5-tetrahydro-1,5-benzoxazepine-5-acetate (0.45 g) as a colorless oil.

IR $\nu_{max}^{neat}$ cm$^{-1}$: 3320(NH); 1770, 1740, 1710, 1680(C=O)

[α]$_D$ −100° (in methanol)

Mass spectrum (m/e): 635(M+)

From the second fraction is obtained tert-butyl 3(S)-[1(S)-ethoxycarbonyl-9-phthalimidononyl]amino-4-oxo-2,3,4,5-tetrahydro-1,5-benzoxazepine-5-acetate (0.55 g) as a colorless oil.

IR $\nu_{max}^{neat}$ cm$^{-1}$: 3320(NH); 1770, 1740, 1710, 1680(C=O)

[α]$_D$ −98° (in methanol)

Mass spectrum (m/e): 635(M+)

EXAMPLE 81

A mixture of tert-butyl 3(S)-[1(S)-ethoxycarbonyl-9-phthalimidononyl]amino-4-oxo-2,3,4,5-tetrahydro-1,5-benzoxazepine-5-acetate (0.08 g) and 5N hydrogen chloride-ethyl acetate solution (5 ml) is allowed to stand at room temperature for 3 hours. The mixture is diluted with petroleum ether (80 ml) to precipitate colorless powder, which is collected and dried under reduced pressure to yield 3(S)-[1(S)-ethoxycarbonyl-9-phthalimidononyl]amino-4-oxo-2,3,4,5-tertrahydro-1,5-benzoxazepine-5-acetic acid hydrochloride (0.066 g).

[α]$_D$ −101° (in methanol)

Elemental analysis for C$_{31}$H$_{37}$N$_3$O$_8$.HCl.½H$_2$O: Calcd.: C, 59.56; H, 6.29; N, 6.72; Found: C, 59.29; H, 6.48; N, 6.51

EXAMPLE 82

A mixture of tert-butyl 3(S)-[1(S)-ethoxycarbonyl-9-phthalimidononyl]amino-4-oxo-2,3,4,5-tetrahydro-1,5-benzoxazepine-5-acetate (0.46 g), hydrazine hydrate (0.18 g) and ethanol (10 ml) is allowed to stand overnight at room temperature. The mixture is concentrated under reduced pressure, diluted with water (50 ml) and extracted with ethyl acetate (50 ml×4). Water (50 ml) and sodium bicarbonate (0.5 g) are added to the organic extract, and to the resulting mixture is added dropwise di-tert-butyl dicarbonate (0.24 g) with stirring. After stirring for 30 minutes at room temperature, the ethyl acetate layer is dried over anhydrous magnesium sulfate and concentrated in vacuo. The residue is purified by silica gel column chromatography using hexane-ethyl acetate (2:1) as an eluent to yield tert-butyl 3(S)-[9-tert-butoxycarbonylamino-1(S)-ethoxycarbonylnonyl-]amino-4-oxo-2,3,4,5-tetrahydro-1,5-benzoxazepine-5-acetate (0.35 g) as a colorless oil.

IR $\nu_{max}^{neat}$ cm$^{-1}$: 1740, 1710, 1680(C=O)

[α]$_D$ −116° (in methanol)

Mass spectrum (m/e): 605(M+)

EXAMPLE 83

A mixture of terty-butyl 3(S)-[9-tert-butoxycarbonylamino-1(S)-ethoxycarbonylnonyl]amino-4-oxo-2,3,4,5-tetrahydro-1,5-benzoxazepine-5-acetate (0.33 g) and 5N hydrogen chloride-ethyl acetate solution (8 ml) is allowed to stand for 2.5 hours at room temperature. The mixture is diluted with petroleum ether (80 ml) to deposit colorless powder, which is collected and dried under reduced pressure to give 3(S)-[9-amino-1(S)-ethoxycarbonylnonyl]amino-4-oxo-2,3,4,5-tetrahydro-1,5-benzoxazepine-5-acetic acid dihydrochloride (0.25 g).

Elemental Analysis for C$_{23}$H$_{35}$N$_3$O$_6$.2HCl.H$_2$O: Calcd: C, 51.11, H, 7.27; N, 7.77; Found: C, 51.17; H, 7.57; N, 7.34

[α]$_D$ −110° (in methanol)

EXAMPLE 84

A solution of 3(S)-[9-amino-1(S)-ethoxycarbonylnonyl]amino-4-oxo-2,3,4,5-tetrahydro-1,5-benzoxazepine-5-acetic acid dihydrochloride (0.2 g) in 1N sodium hydroxide solution (6 ml) is allowed to stand for 30 minutes at room temperature. Acetic acid (1.5 ml) is added and the resulting mixture is subjected to Amberlite XAD-2 column chromatography using methanol-water (1:2) as an eluent. The eluate is concentrated in vacuo and lyophilized to yield 3(S)-[9-amino-1(S)-carboxynonyl]amino-4-oxo-2,3,4,5-tetrahydro-1,5-benzoxazepine-5-acetic acid (0.15 g) as colorless powder.

Elemental Analysis for C$_{21}$H$_{31}$N$_3$O$_6$.H$_2$O: Calcd.: C, 57.39; H, 7.57; N, 9.56; Found: C, 57.42; H, 7.27; N, 9.58

[α]$_D$ −142° (in methanol)

SIMS spectrum (m/e): 422(MH+)

EXAMPLE 85

A mixture of 3(S)-amino-2,3,4,5-tetrahydro-1,5-benzoxazepine-4-one hydrochloride (2 g), ethanol (100 ml), sodium acetate (0.8 g), acetic acid (0.6 g), molecular sieves 4A (5 g) and ethyl 4-cyclohexyl-2-oxo-butyrate (5 g) is catalytically hydrogenated over Raney nickel at room temperature under atmospheric pressure. After the absorption of hydrogen ceases, the catalyst is removed by filtration and the filtrate is evaporated in vacuo. To the residue are added water (50 ml) and ethyl acetate (200 ml), and the mixture is agitated thoroughly. The ethyl acetate layer is dried over anhydrous magnesium sulfate and evaporated in vacuo to yield an oily residue containing 3-(1-ethoxycarbonyl-3-cyclohexylpropyl)amino-2,3,4,5-tetrahydro-1,5-benzoxazepine-4-one. A mixture of this oil, potassium carbonate (4 g), tert-butyl chloroacetate (3 g), potassium iodide (0.2 g) and N,N-dimethylformamide (20 ml) is stirred overnight at room temperature, and then diluted with a mixture of water (300 ml) and ethyl acetate (200 ml). The organic layer is separated, dried over anhydrous magnesium sulfate and evaporated in vacuo to yield an oil, which is purified by silica gel column chromatography using hexaneethyl acetate (4:1) as an eluant to yield tert-butyl 3-(1-ethoxycarbonyl-3-cyclohexylpropyl-)amino-4-oxo-2,3,4,5-tetrahydro-1,5-benzoxazepine-5-acetate (1 g) as a colorless oil.

IR $\nu_{max}^{neat}$ cm$^{-1}$: 3330(NH); 1730, 1680(C=O)

EXAMPLE 86

A mixture of benzyl 3(S)-amino-4-oxo-2,3,4,5-tetrahydro-1,5-benzoxazepine-5-acetate hydrochloride (2.5 g), ethanol (30 ml), sodium acetate (0.57 g), acetic acid (0.4 g), ethyl 5-(1-benzyloxycarbonyl-4-piperidyl)-2-oxovalerate (2.5 g) and molecular sieves 3A (10 g) is stirred for 10 minutes at room temperature. To the stirred mixture is added dropwise a solution of sodium cyanoborohydride (0.4 g) in ethanol (50 ml) for 2 hours. After standing overnight at room temperature, the mixture is concentrated in vacuo and diluted with a mixture of water (300 ml) and ethyl acetate (300 ml). The resulting mixture is agitated thoroughly and filtered. The ethyl acetate layer is separated, dried over anhydrous magnesium sulfate and concentrated in vacuo. The residue is dissolved in a mixture of ethyl acetate (20 ml) and oxalic acid (2 g). This solution is diluted with petroleum ether (300 ml), and the supernatant layer is removed by decantation. To the precipitate are added water (100 ml), ethyl acetate (200 ml) and excess sodium bicarbonate. The ethyl acetate layer is separated, dried over anhydrous magnesium sulfate and evaporated in vacuo. The oily residue is subjected to silica gel column chromatography using hexane-ethyl acetate (2:1) as an eluent. Evaporation of the first fraction gives benzyl 3(S)-[4-(1-benzyloxycarbonyl-4-piperidyl)-1(R)-ethoxycarbonylbutyl]amino-4-oxo-2,3,4,5-tetrahydro-1,5-benzoxazepine-5-acetate (0.65 g) as a colorless oil.

IR $\nu_{max}^{neat}$ cm$^{-1}$: 3320(NH); 1740, 1690, 1680(C=O)
Mass spectrum (m/e): 671(M+)

From the second fraction is obtained benzyl 3(S)-[4-(1-benzyloxycarbonyl-4-piperidyl)-1-(S)-ethoxycarbonylbutyl]amino-4-oxo-2,3,4,5-tetrahydro-1,5-benzoxazepine-5-acetate (0.75 g) as a colorless oil.

IR $\nu_{max}^{neat}$ cm$^{-1}$: 3320(NH); 1740, 1690, 1680(C=O)
Mass spectrum (m/e): 671(M+)

EXAMPLE 87

A solution of benzyl 3(S)-[4-(1-benzyloxycarbonyl-4-piperidyl)-1(R)-ethoxycarbonylbutyl]amino-4-oxo-2,3,4,5-tetrahydro-1,5-benzoxazepine-5-acetate (0.65 g) in ethanol (50 ml) is subjected to catalytic hydrogenolysis over 10% palladium-carbon (1 g, 50% wet) at room temperature under atmospheric pressure. After the absorption of hydrogen ceases, the catalyst is removed by filtration and the filtrate is evaporated in vacuo. The residue is triturated four times with ethyl ether (100 ml) and then dissolved in ethanol (5 ml). To this solution is added 5N-hydrogen chloride-ethyl acetate solution (1 ml) and the resulting mixture is diluted with ethyl ether to deposit 3(S)-[1(R)-ethoxycarbonyl-4-(4-piperidyl)butyl]amino-4-oxo-2,3,4,5-tetrahydro-1,5-benzoxazepine-5-acetic acid dihydrochloride (0.12 g) as colorless powder.

Elemental analysis for $C_{23}H_{33}N_3O_6 \cdot 2HCl \cdot 2H_2O$: Calcd.: C, 49.64; H, 7.06; N, 7.55; Found: C, 49.17; H, 6.99; N, 7.52

$[\alpha]_D -121°$ (in methanol)

EXAMPLE 88

A solution of benzyl 3(S)-[4-(1-benzyloxycarbonyl-4-piperidyl)-1(S)-ethoxycarbonylbutyl]amino-4-oxo-2,3,4,5-tetrahydro-1,5-benzoxazepine-5-acetate (0.75 g) in ethanol is subjected to catalytic hydrogenolysis over 10% palladium carbon (1 g, 50% wet) at ambient temperature and pressure until the absorption of hydrogen ceases. After removal of the catalyst by filtration, the filtrate is concentrated and diluted with ethyl ether (30 ml) to precipitate colorless powder, which is collected by filtration and then dissolved in ethyl acetate (10 ml). To the solution is added 5N hydrogen chloride-ethyl acetate solution (2 ml), and the resulting mixture is diluted with ethyl ether (50 ml) to deposit colorless powder, which is collected by filtration to yield 3(S)-[1(S)-ethoxycarbonyl-4-(4-piperidyl)butyl]amino-4-oxo-2,3,4,5-tetrahydro-1,5-benzoxazepine-5-acetic acid dihydrochloride (0.45 g).

Elemental analysis for $C_{23}H_{33}N_3O_6 \cdot 2HCl \cdot 2H_2O$: Calcd.: C, 49.64; H, 7.06; N, 7.55; Found: C, 49.83; H, 7.07; N, 7.29

$[\alpha]_D -93°$ (in methanol)

EXAMPLE 89

A solution of 3(S)-[1(S)-ethoxycarbonyl-4-(4-piperidyl)butyl]amino-4-oxo-2,3,4,5-tetrahydro-1,5-benzoxazepine-5-acetic acid dihydrochloride (0.35 g) in 1N sodium hydroxide solution (8 ml) is allowed to stand for 30 minutes at room temperature. After addition of acetic acid (1.5 ml), the mixture is subjected to column chromatography on MCI gel (CHP 20P, 150–300μ, Mitsubishi Chemical) using water-methanol (2:1) as an eluent. The eluate is concentrated in vacuo and lyophilized to yield 3(S)-[1(S)-carboxy-4-(4-piperidyl)butyl]amino-4-oxo-2,3,4,5-tetrahydro-1,5-benzoxazepine-5-acetic acid (0.2 g) as colorless powder.

Elemental analysis for $C_{21}H_{29}N_3O_6 \cdot 3/2H_2O$: Calcd.: C, 56.49; H, 7.22; N, 9.41; Found: C, 56.86; H, 7.31; N, 9.41

$[\alpha]_D -133°$ (in methanol)
SIMS spectrum (m/e): 420(MN+)

EXAMPLE 90

A mixture of benzyl 3(S)-amino-4-oxo-2,3,4,5-tetrahydro-1,5-benzoxazepine-5-acetate hydrochloride (3.4 g), ethanol (30 ml), sodium acetate (0.77 g), acetic acid (0.56 g), ethyl 6-(1-benzyloxycarbonyl-4-piperidyl)-2-oxohexanoate (4.4 g) and molecular sieves 3A (10 g) is stirred for 10 minutes at room temperature. To the stirred mixture is added dropwise a solution of sodium cyanoborohydride (0.6 g) in ethanol (50 ml) for 3 hours. After standing overnight at room temperature, the mixture is concentrated in vacuo and diluted with a mixture of water (100 ml) and ethyl acetate (200 ml). The resulting mixture is agitated thoroughly and filtered. The ethyl acetate layer is separated, dried over anhydrous magnesium sulfate and concentrated in vacuo. The residue is dissolved in a mixture of ethyl acetate (20 ml) and oxalic acid (3 g). This solution is diluted with petroleum ether (100 ml), and the supernatant layer is removed by decantation. To the precipitate are added water (50 ml), ethyl acetate (200 ml) and excess sodium bicarbonate. The ethyl acetate layer is separated, dried over anhydrous magnesium sulfate and evaporated in vacuo. The oily residue is subjected to silica gel column chromatography using hexame-ethyl acetate (2:1) as an eluent. Evaporation of the first fraction gives benzyl 3(S)-[5-(1-benzyloxycarbonyl-4-piperidyl)-1(R)-ethoxycarbonylpentyl]amino-4-oxo-2,3,4,5-tetrahydro-1,5-benzoxazepine-5-acetate (0.35 g) as a colorless oil.

IR $\nu_{max}^{neat}$ cm$^{-1}$: 3320(NH); 1730, 1680(C=O)
Mass spectrum (m/e): 685(M+)

From the second fraction is obtained benzyl 3(S)-[5-(1-benzyloxycarbonyl-4-piperidyl)-1(S)-ethoxycarbonylpentyl]amino-4-oxo-2,3,4,5-tetrahydro-1,5-benzoxazepine-5-acetate (0.65 g) as a colorless oil.

IR $\nu_{max}^{neat}$ cm$^{-1}$: 3330(NH); 1730, 1680(C=O)
Mass spectrum (m/e): 685(M+)

EXAMPLE 91

A solution of benzyl 3(S)-[5-(1-benzyloxycarbonyl-4-piperidyl)-1(R)-ethoxycarbonylpentyl]amino-4-oxo-2,3,4,5-tetrahydro-1,5-benzoxazepine-5-acetate (0.35 g) in ethanol (20 ml) is subjected to catalytic hydrogenolysis over 10% palladium carbon (0.5 g, 50% wet) at ambient temperature and pressure until the absorption of hydrogen ceases. After removal of the catalyst by filtration, the filtrate is concentrated. To the residue is added 5N hydrogen chloride-ethyl acetate solution (1 ml), and the resulting mixture is diluted with ethyl ether (50 ml) to deposit 3(S)-[1(R)-ethoxycarbonyl-5-(4-piperidyl)pentyl]amino-4-oxo-2,3,4,5-tetrahydro-1,5-benzoxazepine-5-acetic acid dihydrochloride (0.25 g) as the colorless precipitate. This acid is dissolved in 1N sodium hydroxide solution (10 ml), and the resulting solution is allowed to stand for 30 minutes at room temperature. After addition of acetic acid (2 ml), the mixture is subjected to MCI gel column chromatography using water-methanol (2:1) as an eluent. The eluate is concentrated in vacuo and lyophilized to yield 3(S)-[1(R)-carboxy-5-(4-piperidyl)pentyl]amino-4-oxo-2,3,4,5-tetrahydro-1,5-benzoxazepine-5-acetic acid (0.5 g) as colorless powder.

Elemental analysis for $C_{22}H_{31}N_3O_6 \cdot 3/2H_2O$: Calcd: C, 57.38; H, 7.44; N, 9.13; Found: C, 57.39; H, 7.62; N, 9.06

$[\alpha]_D - 149°$ (in water)

SIMS spectrum (m/e): 434(MH$^+$)

EXAMPLE 92

A solution of benzyl 3(S)-[5-(1-benzyloxycarbonyl-4-piperidyl)-1(S)-ethoxycarbonylpentyl]amino-4-oxo-2,3,4,5-tetrahydro-1,5-benzoxazepine-5-acetate (0.65 g) in ethanol (40 ml) is subjected to catalytic hydrogenolysis over 10% palladium carbon (1 g, 50% wet) at ambient temperature and pressure until the absorption of hydrogen ceases. After removal of the catalyst by filtration, the filtrate is concentrated. To the residue is added 5N hydrogen chloride-ethyl acetate solution (2 ml), and the resulting mixture is diluted with ethyl ether (50 ml) to deposit 3(S)-[1(S)-ethoxycarbonyl-5-(4-piperidyl)pentyl]amino-4-oxo-2,3,4,5-tetrahydro-1,5-benzoxazepine-5-acetic acid dihydrochloride (0.45 g) as a colorless precipitate. This acid is dissolved in 1N sodium hydroxide solution (15 ml), and the resulting solution is allowed to stand for 30 minutes at room temperature. After addition of acetic acid (3 ml), the mixture is subjected to MCI gel column chromatography using water-methanol (2:1) as an eluent. When eluate is concentrated in vacuo and lyophilized to yield 3(S)-[1(S)-carboxy-5-(4-piperidyl)pentyl]amino-4-oxo-2,3,4,5-tetrahydro-1,5-benzoxazepine-5-acetic acid (0.3 g) as colorless powder.

Elemental analysis for $C_{22}H_{31}N_3O_6 \cdot 3/2H_2O$: Calcd.: C, 57.38; H, 7.44; N, 9.13; Found: C, 57.01; H, 7.76; N, 9.00

$[\alpha]_D - 118°$ (in water)

SIMS spectrum (m/e): 434(MH$^+$)

EXAMPLE 93

A mixture of tert-butyl 3(S)-amino-4-oxo-2,3,4,5-tetrahydro-1,5-benzoxazepine-5-acetate (2.4 g), ethanol (30 ml), acetic acid (0.5 g), ethyl 7-(1-benzyloxycarbonyl-4-piperidyl)-2-oxoheptanoate (3.2 g) and molecular sieves 3A (10 g) is stirred for 10 minutes. To the stirred mixture is added dropwise a solution of sodium cyanoborohydride (0.51 g) in ethanol (50 ml) for 3 hours at room temperature. After standing overnight at room temperature, the mixture is concentrated in vacuo and diluted with a mixture of water (50 ml) and ethyl acetate (200 ml). The resulting mixture is agitated thoroughly and filtered. The ethyl acetate layer is washed successively with 0.1N hydrochloric acid, 0.1N sodium hydroxide solution and water, dried over anhydrous magnesium sulfate and concentrated in vacuo. The oily residue is chromatographed on silica gel using hexane-ethyl acetate (2:1) as an eluent. Evaporation of the first fraction affords tert-butyl 3(S)-[6(1-benzyloxycarbonyl-4-piperidyl)-1(R)-ethoxycarbonylhexyl]amino-4-oxo-2,3,4,5-tetrahydro-1,5-benzoxazepine-5-acetate (0.35 g) as a colorless oil.

IR $\nu_{max}^{neat}$ cm$^{-1}$: 3320(NH); 1730, 1680(C=O)

From the second fraction is obtained tert-butyl 3(S)-[6-(1-benzyloxycarbonyl-4-piperidyl)-1(S)-ethoxycarbonylhexyl]amino-4-oxo-2,3,4,5-tetrahydro-1,5-benzoxazepine-5-acetate (0.5 g) as a colorless oil.

IR $\nu_{max}^{neat}$ cm$^{-1}$: 3320(NH); 1730, 1680(C=O)

Mass spectrum (m/e): 665(M$^+$)

EXAMPLE 94

To a solution of tert-butyl 3(S)-[6-(1-benzyloxycarbonyl-4-piperidyl)-1(R)-ethoxycarbonylhexyl]amino-4-oxo-2,3,4,5-tetrahydro-1,5-benzoxazepine-5-acetate (0.35 g) in acetic acid (1 ml) is added 30% hydrogen bromide-acetic acid solution (2 ml). The resulting mixture is allowed to stand for 1 hour at room temperature and then diluted with ethyl ether (100 ml). The supernatant layer is removed by decantation and the precipitate is dissolved in 1N sodium hydroxide solution (10 ml). The solution is allowed to stand for 60 minutes at room temperature. After addition of acetic acid (1 ml), the mixture is chromatographed on MCI gel using water-methanol (1:2) as an eluent. The eluate is concentrated in vacuo and lyophilized to give 3(S)-[1(R)-carboxy-6-(4-piperidyl)hexyl]amino-4-oxo-2,3,4,5-tetrahydro-1,5-benzoxazepine-5-acetic acid (0.13 g) as colorless powder.

$[\alpha]_D - 139°$ (in water)

SIMS spectrum (m/e): 448(MH$^+$)

EXAMPLE 95

To a solution of tert-butyl 3(S)-[6-(1-benzyloxycarbonyl-4-piperidyl)-1(S)-ethoxycarbonylhexyl]amino-4-oxo-2,3,4,5-tetrahydro-1,5-benzoxazepine-5-acetate (0.5 g) in acetic acid (1 ml) is added 30% hydrogen bromide-acetic acid solution (2 ml). The resulting mixture is allowed to stand for 1 hour at room temperature and then diluted with ethyl ether (100 ml). The supernatant layer is removed by decantation and the precipitate is dissolved in 1N sodium hydroxide solution (20 ml). The solution is allowed to stand for 30 minutes at room temperature. After addition of acetic acid (4 ml), the mixture is chromatographed on MCI gel using water-methanol (1:2) as an eluent. The eluate is concentrated in vacuo and lyophilized to give 3(S)-[1(S)-carboxy-6-(4-piperidyl)hexyl]amino-4-oxo-2,3,4,5-tetrahydro-1,5-benzoxazepine-5-acetic acid (0.23 g) as colorless powder.

$[\alpha]_D - 133°$ (in water)

SIMS spectrum (m/e): 448(MH$^+$)

EXAMPLE 96

A mixture of tert-butyl 3(S)-amino-4-oxo-2,3,4,5-tetrahydro-1,5-benzoxazepine-5-acetate (2 g), ethanol (10 ml), acetic acid (0.49 g), ethyl 8-(1-benzyloxycarbonyl-4-piperidyl)-2-oxooctanoate (3 g) and molecular sieves 3A (10 g) is stirred for 10 minutes. To the stirred mixture is added dropwise a solution of sodium cyanoborohydride (0.47 g) in ethanol (40 ml) for 3 hours at room temperature. After standing overnight at room temperature, the mixture is concentrated in vacuo and diluted with a mixture of water (100 ml) and ethyl acetate (200 ml). The resulting mixture is agitated thoroughly and filtered. The ethyl acetate layer is washed with water, dried over anhydrous magnesium sulfate and concentrated in vacuo. The oily residue is chromatographed on silica gel using hexane-ethyl acetate (5:2–2:1) as an eluent. Evaporation of the first fraction affords tert-butyl 3(S)-[7-(1-benzyloxycarbonyl-4-piperidyl)-1(R)-ethoxycarbonylheptyl]amino-4-oxo-2,3,4,5-tetrahydro-1,5-benzoxazepine-5-acetate (0.35 g) as a colorless oil.

IR $\nu_{max}^{neat}$ cm$^{-1}$: 3320(NH); 1740, 1700, 1680(C=O)

From the second fraction is obtained tert-butyl 3(S)-[7-(1-benzyloxycarbonyl-4-piperidyl)-1(S)-ethoxycarbonylheptyl]amino-4-oxo-2,3,4,5-tetrahydro-1,5-benzoxazepine-5-acetate (0.35 g) as a colorless oil.

IR $\nu_{max}^{neat}$ cm$^{-1}$: 3320(NH); 1740, 1690, 1680(C=O)

EXAMPLE 97

To a solution of tert-butyl 3(S)-[7-(1-benzyloxycarbonyl-4-piperidyl)-1(R)-ethoxycarbonylheptyl]amino-4-oxo-2,3,4,5-tetrahydro-1,5-benzoxazepine-5-acetate (0.35 g) in acetic acid (1.5 ml) is added 30% hydrogen bromide-acetic acid solution (1.5 ml). The resulting mixture is allowed to stand for 0.5 hour at room temperature and then diluted with ethyl ether (100 ml). The supernatant layer is removed by decantation and the precipitate is dissolved in 1N sodium hydroxide solution (10 ml). The solution is allowed to stand for 30 minutes at room temperature. After addition of acetic acid (2 ml), the mixture is chromatographed on Amberlite XAD-2 using water-methanol (1:1) as an eluent. The eluate is concentrated in vacuo and lyophilized to give 3(S)-[1(R)-carboxy-7-(4-piperidyl)heptyl]amino-4-oxo-2,3,4,5-tetrahydro-1,5-benzoxazepine-5-acetic acid (0.1 g) as colorless powder.

$[\alpha]_D$ −119° (in water)

SIMS spectrum (m/e): 462(MH+)

EXAMPLE 98

To a solution of tert-butyl 3(S)-[7-(1-benzyloxycarbonyl-4-piperidyl)-1(S)-ethoxycarbonylheptyl]amino-4-oxo-2,3,4,5-tetrahydro-1,5-benzoxazepine-5-acetate (0.35 g) in acetic acid (1.5 ml) is added 30% hydrogen bromide-acetic acid solution (1.5 ml). The resulting mixture is allowed to stand for 0.5 hour at room temperature and then diluted with ethyl ether (100 ml). The supernatant layer is removed by decantation and the precipitate is dissolved in 1N sodium hydroxide solution (10 ml). The solution is allowed to stand for 30 minutes at room temperature. After addition of acetic acid (2 ml), the mixture is chromatographed on MCI gel using water-methanol (1:1) as an eluent. The eluate is concentrated in vacuo and lyophilized to give 3(S)-[1(S)-carboxy-7-(4-piperidyl)heptyl]amino-4-oxo-2,3,4,5-tetrahydro-1,5-benzoxazepine-5-acetic acid (0.15 g) as colorless powder.

$[\alpha]_D$ −108° (in water)

SIMS spectrum (m/e): 462(MH+)

EXAMPLE 99

A mixture of isonicotinaldehyde (25 g), ethyl(triphenylphosphoranylidene)acetate (82 g) and toluene (300 ml) is stirred for 3 hours at 100° C. After cooling, the crystals that precipitated are removed by filtration, and the filtrate is concentrated in vacuo. The residue is dissolved in a mixture of ethyl acetate and petroleum ether (1:1, 400 ml), and the resulting solution is extracted with 5% hydrochloric acid (500 ml). The aqueous layer is extracted with ethyl acetate (50 ml) and neutralized with potassium carbonate. After cooling, the resulting crystals are collected by filtration and dried to give ethyl 3-(4-pyridyl)acrylate (34 g) as colorless prisms, mp 64°–66° C.

EXAMPLE 100

A solution of ethyl 3-(4-pyridyl)acrylate (28 g) in acetic acid (300 ml) is catalytically reduced at room temperature under atmospheric pressure over platinum oxide (1 g). After absorption of hydrogen ceases, the catalyst is filtered off, and the filtrate is evaporated in vacuo. The residue is dissolved in a mixture of water (500 ml) and ethyl acetate (300 ml). Sodium bicarbonate is added portionwise to the stirred solution until the generation of carbon dioxide ceases. Benzyloxycarbonyl chloride (5 ml) is added and the resulting mixture is stirred for 1 hour at room temperature. After further addition of benzyloxycarbonyl chloride (20 g), sodium bicarbonate (30 g) is added portionwise to the stirred mixture. After stirring for 2 hour at room temperature, the ethyl acetate layer is separated, washed with water, dried over anhydrous magnesium sulfate and concentrated in vacuo. The oily residue is purified by silica gel column chromatography using hexane-ethyl acetate (2:1) as an eluent to give ethyl 3-(1-benzyloxycarbonyl-4-piperidyl)propionate (37 g) as a colorless oil.

IR $\nu_{max}^{neat}$ cm$^{-1}$: 1730, 1700 (C=O)

EXAMPLE 101

To a stirred mixture of ethyl 4-(1-benzyloxycarbonyl-4-piperidyl)-2-oxobutyrate (17 g), acetic acid (4.5 g) and ethanol (30 ml) is added sodium cyanoborohydride (3 g) at room temperature. After stirring for 3 hours at room temperature, the mixture is diluted with water (500 ml) and extracted with methylene chloride. The organic extract is dried over anhydrous magnesium sulfate and concentrated in vacuo. The residue is purified by silica gel column chromatography using hexane-ethyl acetate (2:1–1:1) as an eluent to give ethyl 4-(1-benzyloxycarbonyl-4-piperidyl)-2-hydroxybutyrate (11.5 g) as a colorless oil.

IR $\nu_{max}^{neat}$ cm$^{-1}$: 3430(OH); 1730, 1690(C=O)

NMR(in CDCl$_3$-D$_2$O) δ: 7.3(5H), 5.1(2H), 3.9–4.4(5H), 2.5–3.1(2H), 1.0–2.0(12H)

EXAMPLE 102

To a mixture of ethyl 4-(1-benzyloxycarbonyl-4-piperidyl)-2-hydroxybutyrate (11.5 g), ethyl acetate (200 ml) and pyridine (12 g) is added thionyl chloride (5 ml), and the resulting mixture is refluxed for 1 hour with stirring. After cooling, the mixture is diluted with water (500 ml) and ethyl acetate (100 ml). The organic layer is separated, washed successively with 0.1N hydrochloric acid and water, dried over anhydrous magnesium sulfate, treated with activated carbon and then evaporated in vacuo to give ethyl 4-(1-benzyloxycarbonyl-4-piperidyl)-2-chlorobutyrate (10.5 g) as a pale yellow oil.

IR $\nu_{max}^{neat}$ cm$^{-1}$: 1740, 1690(C=O)

EXAMPLE 103

A solution of ethyl 4-(1-benzyloxycarbonyl-4-piperidyl)-2-chlorobutyrate (10.5 g) in ethanol (20 ml) is catalytically hydrogenated over 10% Palladium-carbon (5 g, 50% wet) as a catalyst at ordinary temperature under atmospheric pressure. After the absorption of hydrogen ceases, the catalyst is removed by filtration and the filtrate is concentrated in vacuo to yield ethyl 4-(4-piperidyl)butyrate, which is dissolved in a mixture of ethyl acetate (200 ml) and water (100 ml). To the solution is added sodium bicarbonate (6 g), and the resulting mixture is stirred at room temperature. Benzyloxycarbonyl chloride (6 ml) is added dropwise to the stirred mixture, and the stirring is continued for 1.5 hours at room temperature. The ethyl acetate layer is separated, dried over anhydrous magnesium sulfate and concentrated in vacuo. The residue is purified by silica gel column chromatography using hexane:ethyl acetate (3:1) as an eluent to yield ethyl 4-(1-benzyloxycarbonyl-4-piperidyl)butyrate (5.3 g) as a colorless oil.

IR $\nu_{max}^{neat}$ cm$^{-1}$: 1730, 1700(C=O)

EXAMPLE 104

To a solution of sodium (0.48 g) in ethanol (10 ml) are added ethyl 4-(1-benzyloxycarbonyl-4-piperidyl)butyrate (5.3 g) and diethyl oxalate (2.8 g). The mixture is evaporated under reduced pressure at 60°–70° C. for 30 minutes. After cooling, water (300 ml) is added to the brown residue, and the resulting mixture is acidified with 1N hydrochloric acid and extracted with ethyl acetate (100 ml×2). The organic extract is dried over anhydrous magnesium sulfate and concentrated in vacuo. The oily residue is dissolved in a mixture of dimethylsulfoxide (45 ml), water (5 ml) and lithium chloride (0.8 g). The resulting mixture stirred for 1.5 hours at 135°–140° C. and then for 30 minutes at 140°–145° C. After cooling, the mixture is diluted with water (500 ml) and extracted with ethyl acetate (300 ml). The extract is dried over anhydrous magnesium sulfate and concentrated in vacuo to give ethyl 5-(1-benzyloxycarbonyl-4-piperidyl)-2-oxovalerate (5 g) as an oil.

IR $\nu_{max}^{neat}$ cm$^{-1}$: 1730, 1700(C=O)
Mass spectrum (m/e): 361(M+)

EXAMPLE 105

To a stirred mixture of methylene chloride (400 ml) and water (40 ml) are added dropwise benzyloxycarbonyl chloride (100 g) and a solution of 3-(4-piperidyl)propanol (84 g) and triethylamine (65 g) in methylene chloride (100 ml) for 45 minutes at room temperature. After addition is completed, stirring is continued for further 1 hour. The methylene chloride layer is separated, washed with water, dried over anhydrous magnesium sulfate and concentrated under reduced pressure. Vacuum distillation of the oily residue is carried out to remove the low boiling material (50°–60° C./5 mmHg). 3-(1-Benzyloxycarbonyl-4-piperidyl)propanol (110 g) is obtained as a yellow oily residue.

IR $\nu_{max}^{neat}$ cm$^{-1}$: 3400(OH), 1680(C=O)

EXAMPLE 106

To a chilled mixture of 3-(1-benzyloxycarbonyl-4-piperidyl)propanol (110 g) and pyridine (500 ml) is added portionwise tosyl chloride (100 g) for 2 hours with stirring. After stirring for further 1 hour, ice water (1 l) is added dropwise to the mixture. The resulting mixture is acidified by dropwise addition of concentrated hydrochloric acid at ice-bath temperature and extracted with ethyl acetate (1 l). The extract is washed successively with diluted hydrochloric acid and water, dried over anhydrous magnesium sulfate and concentrated in vacuo. The residue is crystallized from ethanol to give 3-(1-benzyloxycarbonyl-4-piperidyl)propyl p-toluenesulfonate (99 g) as a colorless crystals, mp 59°–60° C.

Elemental analysis for C$_{23}$H$_{29}$NO$_5$S: Calcd.: C, 64.01; H, 6.77; N, 3.25; Found: C, 64.25; H, 6.78; N, 3.26

EXAMPLE 107

To a solution of sodium (5.8 g) in ethanol (300 ml) are added diethyl malonate (40 g) and 3-(1-benzyloxycarbonyl-4-piperidyl)propyl p-toluenesulfonate (90.5 g). The resulting mixture is refluxed for 2 hours with stirring, cooled, diluted with water (1 l) and extracted with ethyl acetate (500 ml). The extract is dried over magnesium sulfate and evaporated in vacuo to give ethyl 5-(1-benzyloxycarbonyl-4-piperidyl)-2-ethoxycarbonylvalerate as an oil. To the stirred solution of this oil in ethanol (200 ml) is added dropwise a solution of sodium hydroxide (34 g) in water (200 ml). After the addition is complete, the mixture is diluted with water (300 ml) and extracted with a mixture of ether and petroleum ether (1:1, 300 ml). The aqueous layer is acidified with concentrated hydrochloric acid and extracted with ethyl acetate (500 ml). The extract is washed with water, dried over anhydrous magnesium sulfate and evaporated in vacuo to yield 5-(1-benzyloxycarbonyl-4-piperidyl)-2-carboxyvaleric acid as an oil. This oil is heated at 160°–170° C. for 45 minutes with stirring to give 5-(1-benzyloxycarbonyl-4-piperidyl)valeric acid (50 g) as an oil.

IR $\nu_{max}^{neat}$ cm$^{-1}$: 1730, 1700(C=O)

EXAMPLE 108

A mixture of 5-(1-benzyloxycarbonyl-4-piperidyl)valeric acid (54.8 g), sodium bicarbonate (29 g), ethyl iodide (21 ml) and N,N-dimethylformamide (150 ml) is stirred for 3 hours at 70°–80° C. After further addition of ethyl iodide (10 ml), the stirring is continued for further 3 hours at 90°–100° C. After cooling, the mixture is diluted with water and extracted with ethyl acetate (1 l). The extract is washed successively with water, 1N hydrochloric acid and sodium bicarbonate solution, dried over anhydrous magnesium sulfate and evaporated in vacuo to yield ethyl 5-(1-benzyloxycarbonyl-4-piperidyl)valerate (58 g) as a pale yellow oil.

IR $\nu_{max}^{neat}$ cm$^{-1}$: 1730, 1700(C=O)
NMR (in CDCl$_3$): 7.3(5H), 5.1(2H), 3.9–4.4(4H), 2.5–3.1(2H), 2.1–2.5(2H), 1.0–1.9(14H)

EXAMPLE 109

To a solution of sodium (2.2 g) in ethanol (50 ml) are added ethyl 5-(1-benzyloxycarbonyl-4-piperidyl)valerate (30 g) and diethyl oxalate (14 g). The mixture is evaporated under reduced pressure at 60° C. for 1 hour and then at 60°–70° C. for 30 minutes. After cooling, water (500 ml) is added to the brown residue. The resulting mixture is acidified with hydrochloric acid and extracted with ethyl acetate (300 ml). The extract is dried over anhydrous magnesium sulfate and evaporated in vacuo to yield an oil. This oil is dissolved in a mixture of dimethylsulfoxide (150 ml), water (15 ml) and lithium chloride (5 g) and the mixture is stirred for 35 minutes at 150°–155° C., cooled, diluted with water (500 ml) and extracted with ethyl acetate (300 ml). The extract is dried over anhydrous magnesium sulfate and evaporated in vacuo to give ethyl 6-(1-benzyloxycarbonyl-4-piperidyl)-2-oxohexanoate (26 g) as an oil.

IR $\nu_{max}^{neat}$ cm$^{-1}$: 1730, 1690(C=O)

Mass spectrum (m/e): 375(M+)

EXAMPLE 110

To a chilled mixture of ethyl 6-(1-benzyloxycarbonyl-4-piperidyl)-2-oxohexanoate (26 g), ethanol (40 ml) and acetic acid (6.2 g) is added sodium cyanoborohydride (4.4 g) with stirring. After being stirred for 1 hour, the mixture is allowed to stand overnight at room temperature, diluted with water (500 ml) and extracted with methylene chloride. The extract is dried over anhydrous magnesium sulfate and concentrated in vacuo. The residue is purified by silica gel column chromatography using hexane-ethyl acetate (2:1) as an eluent to yield ethyl 6-(1-benzyloxycarbonyl-4-piperidyl)-2-hydroxyhexanoate (16 g) as a colorless oil.

IR $\nu_{max}^{neat}$ cm$^{-1}$: 3450(OH); 1730, 1690(C=O)

EXAMPLE 111

To a mixture of ethyl 6-(1-benzyloxycarbonyl-4-piperidyl)-2-hydroxyhexanoate (12.8 g), ethyl acetate (120 ml) and pyridine (13 g) is added thionyl chloride (5.1 ml). The mixture is refluxed for 45 minutes with stirring. After cooling, the mixture is diluted with water (500 ml) and extracted with ethyl acetate (200 ml). The extract is washed successively with 0.1N hydrochloric acid and water, dried over anhydrous magnesium sulfate and concentrated in vacuo. The oily residue is chromatographed on silica gel using hexane-ethyl acetate (4:1) as an eluent to yield ethyl 6-(1-benzyloxycarbonyl-4-piperidyl)-2-chlorohexanoate (10 g) as a colorless oil.

IR $\nu_{max}^{neat}$ cm$^{-1}$: 1740, 1690(C=O)

EXAMPLE 112

A solution of ethyl 6-(1-benzyloxycarbonyl-4-piperidyl)-2-chlorohexanoate (10 g) in ethanol (200 ml) is catalytically hydrogenated over 10% palladium-carbon (5 g, 50% wet) at ordinary temperature under atmospheric pressure. After the absorption of hydrogen has ceased, the catalyst is removed by filtration and the filtrate is evaporated in vacuo to yield ethyl 6-(4-piperidyl)hexanoate. This ester is dissolved in a mixture of water (100 ml), ethyl acetate (200 ml) and sodium bicarbonate (10 g). Benzyloxycarbonyl chloride (7.2 ml) is added dropwise at room temperature and the resulting mixture is stirred overnight. The ethyl acetate layer is separated, dried over anhydrous magnesium sulfate and evaporated in vacuo. The residue is purified by silica gel column chromatography using hexane-ethyl acetate (4:1) as an eluent to give ethyl 6-(1-benzyloxycarbonyl-4-piperidyl)hexanoate (7.7 g) as a colorless oil.

IR $\nu_{max}^{neat}$ cm$^{-1}$: 1730, 1690(C=O)

EXAMPLE 113

To a solution of sodium (0.56 g) in ethanol (20 ml) are added ethyl 6-(1-benzyloxycarbonyl-4-piperidyl)hexanoate (7.3 g) and diethyl oxalate (3.5 g). The mixture is evaporated under reduced pressure at 60°–70° C. for 20 minutes and then at 75° C. for 20 minutes. After cooling, water (100 ml) is added to the brown residue, the resulting mixture is acidified with hydrochloric acid and extracted with ethyl acetate (300 ml). The extract is dried over anhydrous magnesium sulfate and evaporated in vacuo to give an oil. This oil is dissolved in a mixture of dimethylsulfoxide (50 ml), water (5 ml) and lithium chloride (1.5 g). The mixture is stirred for 40 minutes at 140°–160° C., cooled, diluted with water (300 ml) and extracted with ethyl acetate (300 ml). The extract is dried over anhydrous magnesium sulfate and evaporated in vacuo to yield ethyl 7-(1-benzyloxycarbonyl-4-piperidyl)-2-oxoheptanoate (6.5 g) as an oil.

IR $\nu_{max}^{neat}$ cm$^{-1}$: 1720, 1690(C=O)

Mass spectrum (m/e): 389(M+)

EXAMPLE 114

To a stirred mixture of ethyl 5-(1-benzyloxycarbonyl-4-piperidyl)valerate (26.8 g), tetrahydrofuran (200 ml) and sodium borohydride (13.4 g) is added dropwise methanol (40 ml) for 1.5 hours at 70°–80° C. After the addition is complete, the mixture is refluxed for 2 hours with stirring. After evaporation of solvent, the residue is diluted with water (300 ml) and extracted with ethyl acetate (300 ml). The extract is washed successively with 1N hydrochloric acid and water, dried over anhydrous magnesium sulfate and evaporated in vacuo to give 5-(1-benzyloxycarbonyl-4-piperidyl)pentanol (23 g) as a colorless oil.

IR $\nu_{max}^{neat}$ cm$^{-1}$: 3400(OH), 1690(C=O)

NMR (in CDCl$_3$) δ: 7.3(5H), 5.1(2H), 3.9–4.4(2H), 3.5–3.8(2H), 2.4–3.0(3H), 1.0–1.9(13H)

EXAMPLE 115

To a chilled mixture of 5-(1-benzyloxycarbonyl-4-piperidyl)pentanol (18 g) and pyridine (150 ml) is added portionwise tosyl chloride (14.6 g) for 30 minutes with stirring. After stirring for further 1 hour at ice-bath temperature, ice water (2 ml) is added dropwise and the resulting mixture is dissolved in ethyl acetate (500 ml). This solution is washed successively with 2N hydrochloric acid (500 ml), 1N hydrochloric acid (500 ml×2), sodium bicarbonate solution and water. The organic layer is dried over anhydrous magnesium sulfate and concentrated in vacuo. The oily residue is purified by silica gel column chromatography using hexane-ethyl acetate (3:1–2:1) to give 5-(1-benzyloxycarbonyl-4-piperidyl)pentyl p-toluenesulfonate (18 g) as an oil.

IR $\nu_{max}^{neat}$ cm$^{-1}$: 1700(C=O)

EXAMPLE 116

To a solution of sodium (0.95 g) in ethanol (80 ml) are added diethyl malonate (7.2 g) and 5-(1-benzyloxycarbonyl-4-piperidyl)pentyl p-toluenesulfonate (13.7 g). The mixture is refluxed for 2 hours with stirring. After the further addition of a mixture of sodium (0.25 g), ethanol (25 ml) and diethyl malonate (1.8 g), the reflux is continued for further 2 hours. After evaporation of ethanol, the residue is diluted with water (200 ml) and extracted with ethyl acetate (300 ml). The extract is dried over anhydrous magnesium sulfate and evaporated in vacuo to give ethyl 7-(1-benzyloxycarbonyl-4-piperidyl)-2-ethoxycarbonylheptanoate as an oil. To a mixture of this ester and ethanol (30 ml) is added dropwise a solution of sodium hydroxide (6 g) in water (50 ml). After the addition is complete, the mixture is diluted with water (150 ml) and extracted with a mixture of ether and petroleum ether (1:1, 150 ml). The aqueous layer is acidified with concentrated hydrochloric acid and extracted with ethyl acetate (300 ml). The organic extract is washed with water, dried over anhydrous magnesium sulfate and evaporated in vacuo to give 7-(1-benzyloxycarbonyl-4-piperidyl)-2-carboxyheptanoic acid as an oil. This acid is heated for 1 hour at 160°–165° C. with stirring. The resulting oil is purified by silica gel column chromatography using hexane-ethyl acetate (3:1–1:1) as an eluent to yield 7-(1-benzyloxycarbonyl-4-piperidyl)heptanoic acid (6.4 g) as a colorless oil.

IR $\nu_{max}^{neat}$ cm$^{-1}$: 1730, 1710 (C=O)

EXAMPLE 117

A mixture of 7-(1-benzyloxycarbonyl-4-piperidyl)-heptanoic acid (6.4 g), sodium bicarbonate (3.1 g) and ethyl iodide (8.6 g) and N,N-dimethylformamide (20 ml) is stirred for 3 hours at 100° C. After further addition of ethyl iodide (2.9 g) and sodium bicarbonate (1 g), the stirring is continued for further 2.5 hours at 100° C. After cooling, the mixture is diluted with water (200 ml) and extracted with ethyl acetate (300 ml). The extract is washed successively with water, 0.1N hydrochloric acid and sodium bicarbonate solution, dried over anhydrous magnesium sulfate and evaporated in vacuo to give ethyl 7-(1-benzyloxycarbonyl-4-piperidyl)heptanoate (5 g) as an oil.

IR $\nu_{max}^{neat}$ cm$^{-1}$: 1730, 1700(C=O)
NMR (in CDCl$_3$) δ: 7.3(5H), 5.1(2H), 4.0–4.3(4H), 2.5–3.0(2H), 2.1–2.4(2H), 1.0–1.9(18H)

EXAMPLE 118

To a solution of sodium (0.48 g) in ethanol (30 ml) are added ethyl 7-(1-benzyloxycarbonyl-4-piperidyl)heptanoate (6.5 g) and diethyl oxalate (3 g). The mixture is evaporated under reduced pressure at 60°–70° C. for 1 hour. After cooling, water (150 ml) is added to the residue. The mixture is acidified with hydrochloric acid and extracted with ethyl acetate (300 ml). The extract is dried over anhydrous magnesium sulfate and evaporated in vacuo. The oily residue is dissolved in a mixture of dimethylsulfoxide (54 ml), water (6 ml) and lithium chloride (1 g). The resulting solution is stirred for 1 hour at 140° C., cooled, diluted with water (150 ml) and extracted with ethyl acetate (300 ml). The extract is washed with water, dried over anhydrous magnesium sulfate and evaporated in vacuo to yield ethyl 8-(1-benzyloxycarbonyl-4-piperidyl)-2-oxooctanoate (6 g) as an oil.

IR $\nu_{max}^{neat}$ cm$^{-1}$: 1730, 1700(C=O)
Mass spectrum (m/e): 403(M+)

EXAMPLE 119

A mixture of 4-(3,4,5,6-tetrahydro-2H-pyran)carbaldehyde (13.2 g), ethyl(triphenylphosphoranylidene)acetate (44 g) and toluene (200 ml) is stirred for 3 hours at 100° C. After the mixture is concentrated in vacuo, petroleum ether (200 ml) is added to the residue. The resulting precipitate is removed by filtration and the filtrate is concentrated in vacuo. The oily residue is purified by vacuum distillation to give ethyl 3-(3,4,5,6-tetrahydro-2H-pyran-4-yl)acrylate (17 g) as an oil.

bp 132°–134° C. (16 mmHg)
IR $\nu_{max}^{neat}$ cm$^{-1}$: 1720(C=O), 1650(C=C)
NMR (in CDCl$_3$) δ: 6.6–7.1(1H), 5.6–6.9(1H), 3.7–4.4(4H), 3.2–3.7(2H), 2.0–2.7(1H), 1.1–1.9(7H)

EXAMPLE 120

A solution of ethyl 3-(3,4,5,6-tetrahydro-2H-pyran-4-yl)acrylate (17 g) in ethanol (200 ml) is catalytically hydrogenated over 10% palladium-carbon (4 g, 50% wet) at room temperature under atmospheric pressure. After the absorption of hydrogen has ceased, the catalyst is removed by filtration and the filtrate is concentrated in vacuo. The oily residue is purified by vacuum distillation to give ethyl 3-(3,4,5,6-tetrahydro-2H-pyran-4-yl)propionate (15 g) as an oil.

bp 121°–123° C./16 mmHg
IR $\nu_{max}^{neat}$ cm$^{-1}$: 1740(C=O)
NMR (in CDCl$_3$) δ: 3.7–4.4(4H), 3.0–3.7(2H), 2.1–2.7(2H), 1.0–1.9(10H)

EXAMPLE 121

To a stirred solution of oxalyl chloride (10.2 ml) in methylene chloride (200 ml) is added dropwise a solution of dimethylsulfoxide (18.2 ml) in methylene chloride (200 ml) at −65° C. for 10 minutes. After stirring for 10 minutes, a solution of 4-thianylmethanol (14.1 g) in methylene chloride (100 ml) is added dropwise for 10 minutes, and the mixture is stirred for 20 minutes at −65° C. Triethylamine (74 ml) is added dropwise for 10 minutes and the resulting mixture is stirred for 15 minutes under cooling. After the cooling bath is removed, the stirring is continued for 10 minutes at room temperature and 3N hydrochloric acid (215 ml) is added. The resulting mixture is stirred for further 1 hour at room temperature. The organic layer is separated, washed with water, dried over anhydrous magnesium sulfate and evaporated in vacuo to yield 4-thianylcarbaldehyde (11 g) as a pale yellow oil.

IR $\nu_{max}^{neat}$ cm$^{-1}$: 1730(C=O)
NMR (in CDCl$_3$) δ: 9.5(1H), 3.0–4.5(1H), 2.5–3.0(4H), 1.0–2.5(4H)

EXAMPLE 122

A mixture of 4-thianylcarbaldehyde (11 g), ethyl(triphenylphosphoranylidene)acetate (32.3 g) and toluene (200 ml) is stirred at 100° C. for 4 hours. After removal of the solvent, petroleum ether (200 ml) is added to the residue and the resulting precipitate is removed by filtration. The filtrate is concentrated in vacuo to give an oily residue, which is purified by vacuum distillation to yield ethyl 3-(4-thianyl)acrylate (10.4 g) as an oil.

bp 155°–157° C. (15 mmHg)
IR $\nu_{max}^{neat}$ cm$^{-1}$: 1720(C=O), 1650(C=C)
NMR (in CDCl$_3$) δ: 6.6–7.1(1H), 5.6–6.0(1H), 4.0–4.4(2H), 2.6–2.9(4H), 1.5–2.4(5H), 1.2–1.5(3H)

EXAMPLE 123

A solution of ethyl 3-(4-thianyl)acrylate (10 g) in ethanol (150 ml) is hydrogenated over 10% palladium-carbon (9 g, 50% wet) under atmospheric pressure. After the mixture is stirred for 20 minutes at room temperature and then for 8 hours at 50° C., the catalyst is removed by filtration. To the filtrate 10% palladium carbon (9 g, 50% wet) is added and the mixture is hydrogenated at 50° C. for 1 day. After the catalyst is removed by filtration, the filtrate is evaporated in vacuo to give ethyl 3-(4-thianyl)propionate (9.1 g) as an oil.

IR $\nu_{max}^{neat}$ cm$^{-1}$: 1740(C=O)
NMR (in CDCl$_3$) δ: 3.9–4.3(2H), 2.4–2.8(4H), 1.8–2.4(4H), 1.0–1.8(8H)

EXPERIMENT EXAMPLE 1

Experiment of Inhibition of Angiotensin I Converting Enzyme (ACE) by the Compounds of this Invention

Experimental Method

The experiment was conducted in accordance with a modification of the method described by Cushman et al.

(Biochemical Pharmacology, Vol. 20, pp. 1637, 1971). That is, using hippuryl-L-histidyl-L-leucine (HHL) as the substrate, the ACE inhibitory activity was determined in terms of percent inhibition on the amount of hippuric acid produced by ACE when the compound of the present invention was added. A solution of the compound of the present invention dissolved in 0.02 to 0.5% dimethylsulfoxide-100 mM borate-HCl buffer solution (pH 8.3, containing 300 mM sodium chloride) was added to 100 μl of ACE (protein concentration, 20 mg/ml) and 100 μl of 1.25 mM HHL. In this experiment, a borate-HCl buffer solution containing dimethylsulfoxide at a concentration equal to that of the test solution was used as a control. After warming the solution at 37° C. for 1 hour, 150 μl of 1N hydrochloric acid was added to the solution to terminate the reaction. After 0.8 ml of ethyl acetate was added the solution was centrifuged at 11500 rpm for 2 minutes. A 0.5 ml aliquot was separated from the ethyl acetate layer and dried at a temperature below 40° C. under nitrogen gas streams. The residue was mixed thoroughly with 4.5 ml of distilled water, and the mixture was subjected to colorimetry at a wavelength of 228 nm.

TEST RESULTS

The test results obtained with regard to the compounds of the present invention are as shown in Table 6.

TABLE 6

| Ex. No. of tested compound | Concentration (μM) | ACE inhibitory activity (%) |
| --- | --- | --- |
| 20 | 0.1 | 91 |
|  | 1 | 99 |
| 58 | 0.1 | 95 |
|  | 1 | 100 |
| 59 | 0.1 | 93 |
| 60 | 0.1 | 95 |
|  | 1 | 99 |
| 61 | 0.1 | 93 |
| 69 | 0.1 | 99 |
|  | 1 | 100 |
| 89 | 0.1 | 95 |
| 92 | 0.1 | 99 |
| 95 | 0.1 | 99 |
| 98 | 0.1 | 99 |

EXPERIMENT EXAMPLE 2

Effect of the Compounds of the Present Invention against Hypertensive Activity of Angiotensin I

Experimental Method

Male rats (Sprague-Dawley) weighing 250 to 350 g which were fed under free access to drinking water and feed were used as experimental animals. The rats were anesthetized with intraperitoneal administration of pentobarbital sodium (50 mg/kg) on the day before the test day and a polyethylene tube was inserted into each of the femoral artery for measurement of blood pressure and the femoral vein for injection of angiotensin I and II. And the tubes were fixed.

On the test day, an average blood pressure in the control phase was measured by an electric hemodynamometer (MPU-0.5-290-0-III model manufactured by NEC-Sanei, Japan) and recorded by a polygraph (NEC-Sanei, Type 365 or Nippon Kohden Type RM-45), and thereafter angiotensin I and then angiotensin II were injected through the femoral vein at a dose of 300 ng/kg and 100 ng/kg, respectively, to measure the hypertensive activity. Then, 10 mg/kg of the compound of the present invention was administered orally as an aqueous solution or an aqueous gum arabic suspension, and 20, 60 and 120 minutes after the administration, angiotensin I and II were injected repeatedly to trace hypertensive reactions. In calculating the percent inhibition to the hypertensive activity of angiotensin I, the percent inhibitory value was corrected based on the variation with time in the hypertensive reaction by angiotensin II.

Test Results

The test results obtained with regard to the compounds of the present invention are as shown in Table 7.

TABLE 7

| Ex. No. of tested compound | Dose mg/kg (orally) | Inhibition against hypertensive reaction by angiotensin I (%) | | |
| --- | --- | --- | --- | --- |
| | | After 20 min. | After 60 min. | After 120 min. |
| 18 | 10 | 82 | 58 | 60 |
| 23 | 10 | 97 | 89 | 86 |
| 57 | 10 | 98 | 96 | 86 |
| 55 | 10 | 87 | 78 | 82 |
| 38 | 10 | 93 | 73 | 63 |

EXPERIMENT EXAMPLE 3

Effect of the Compounds of the Present Invention against Hypertensive Activity of Angiotensin I

Experimental Method

Male rats (Sprague-Dawley) weighing 300 to 400 g which were fed under free access to drinking water and feed were used as experimental animals. The rats were anesthetized with intraperitoneal administration of pentobarbital sodium (50 mg/kg) on the day before the test day and a polyethylene tube was inserted into each of the femoral artery for measurement of blood pressure and the femoral vein for injection of angiotensin I and II and the tubes were fixed.

On the test day, an average blood pressure in the control phase was measured by an electric hemodynamometer (MPU-0.5-290-0-III model manufactured by NEC-Sanei, Japan) and recorded by a polygraph (NEC-Sanei, Type 365 or Nippon Kohden Type RM-45), and thereafter angiotensin I and then angiotensin II were injected through the femoral vein at a dose of 300 ng/kg and 100 ng/kg, respectively, to measure the hypertensive activity. Then, 300 ng/kg of the compound of the present invention were administered intravenously as a saline solution, and 5, 10, 30, 60, 90 and 120 minutes after the administration, angiotensin I and II were injected repeatedly to trace hypertensive reactions. In calculating the percent inhibition to the hypertensive activity of angiotensin I, the percent inhibitory value was corrected based on the variation with time in the hypertensive reaction by angiotensin II.

Test Results

The test results obtained with regard to the compounds of the present invention are as shown in Table 8.

TABLE 8

| Ex. No. of tested compound | Dose µg/kg (i.v.) | Inhibition against hypertensive reaction by angiotensin I (%) | | | | | |
|---|---|---|---|---|---|---|---|
| | | After 5 min | After 10 min | After 30 min | After 60 min | After 90 min | After 120 min |
| 60 | 300 | 100 | 98 | 97 | 74 | 52 | 26 |
| 68 | 300 | 100 | 100 | 97 | 93 | 82 | 65 |
| 69 | 300 | 99 | 100 | 93 | 86 | 75 | 65 |
| 79 | 300 | 100 | 100 | 100 | 99 | 85 | 71 |
| 92 | 300 | 100 | 100 | 100 | 100 | 100 | 100 |
| 95 | 300 | 100 | 100 | 100 | 99 | 96 | 78 |

Preparation Example

The compounds (I) of the present invention can be used, for example, for treatment of hypertention in the following examples of formulation.

1. Tablets

| | |
|---|---|
| (1) 3(S)—[1(S)—Ethoxycarbonyl-3-phenylpropyl]-amino-4-oxo-2,3,4,5-tetrahydro-1,5-benzoxazepine-5-acetic acid hydrochloride | 10 g |
| (2) Lactose | 90 g |
| (3) Corn starch | 29 g |
| (4) Magnesium stearate | 1 g |
| | 130 g for 1000 tablets |

The above ingredients (1) and (2) and 17 g of (3) are blended, and granulated together with a paste prepared from 7 g of the ingredient (3). Five g of the ingredient (3) and the ingredient (4) are added to the resulting granules, and the mixture is compressed by a tabletting machine to prepare 1000 tablets of a diameter of 7 mm each containing 10 mg of the ingredient (1).

2. Capsules

| | |
|---|---|
| (1) 3(S)—[1(S)—Ethoxycarbonyl-3-cyclohexylpropyl]-amino-4-oxo-2,3,4,5-tetrahydro-1,5-benzoxazepine-5-acetic acid hydrochloride | 10 g |
| (2) Lactose | 135 g |
| (3) Finely powdered cellulose | 70 g |
| (4) Magnesium stearate | 5 g |
| | 220 g for 1000 capsules |

All of the above ingredients are blended and filled into 1000 capsules of Gelatin Capsule No. 3 (X Japanese Pharmacopoiea) to prepare 1000 capsules each containing 10 mg of the ingredient (1).

3. Injectable solution

| | |
|---|---|
| (1) 3(S)—[1(S)—Carboxy-3-(4-piperidyl)propyl]-amino-4-oxo-2,3,4,5-tetrahydro-1,5-benzoxazepine-5-acetic acid | 10 g |
| (2) Sodium chloride | 9 g |

All of the above ingredients are dissolved in 1000 ml of distilled water and charged into 1000 brown ampoules each containing 1 ml of the solution. The air in the ampoules is replaced with nitrogen gas and the ampoules are sealed. The entire preparation steps are conducted under sterile conditions.

4. Tablets

| | |
|---|---|
| (1) 3(S)—[1(S)—Carboxy-6-(4-piperidyl)hexyl]amino-4-oxo-2,3,4,5-tetrahydro-1,5-benzoxazepine-5-acetic acid | 10 g |
| (2) Lactose | 90 g |
| (3) Corn starch | 29 g |
| (4) Magnesium stearate | 1 g |
| | for 1000 tablets |

The above ingredients (1) and (2) and 17 g of (3) are blended, and granulated together with a paste prepared from 7 g of the ingredient (3). Five g of the ingredient (3) and the ingredient (4) are added to the resulting granules, and the mixture is compressed by a tabletting machine to prepare 1000 tablets of the diameter of 7 mm each containing 10 mg of the ingredient (1).

5. Capsules

| | |
|---|---|
| (1) 3(S)—[1(S)—Carboxy-5-(4-piperidyl)pentyl]amino-4-oxo-2,3,4,5-tetrahydro-1,5-benzoxazepine-5-acetic acid | 10 g |
| (2) Lactose | 135 g |
| (3) Finely powdered cellulose | 70 g |
| (4) Magnesium stearate | 5 g |
| | for 1000 capsules |

All of the above ingredients are blended and filled into 1000 capsules of Gelatin Capsule No. 3 (X Japanese Pharmacopoiea) to prepare 1000 capsules each containing 10 mg of the ingredient (1).

6. Injectable solution

| | |
|---|---|
| (1) 3(S)—[8-Amino-1(S)—ethoxycarbonyloctyl]-amino-4-oxo-2,3,4,5-tetrahydro-1,5-benzoxazepine-5-acetic acid dihydrochloride | 10 g |
| (2) Sodium chloride | 9 g |

All of the above ingredients are dissolved in 1000 ml of distilled water and charged into 1000 brown ampoules each containing 1 ml of the solution. The air in the ampoules is replaced with nitrogen gas and the ampoules are sealed. The entire preparation steps are conducted under sterile conditions.

We claim:

1. A compound of the formula

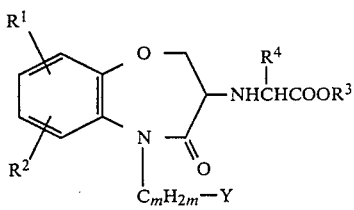

wherein $R^1$ and $R^2$ are independently hydrogen, halogen, trifluoromethyl, $C_{1-4}$ alkyl or $C_{1-4}$ alkoxy, or both jointly form tri- or tetramethylene, $R^3$ is hydrogen; optionally carboxy, $C_{1-4}$ alkoxycarbonyl, phenoxycarbonyl or phenyl-$C_{1-4}$ alkoxycarbonyl substituted $C_{1-6}$ alkyl; or optionally halogen, $C_{1-4}$ alkyl, $C_{1-4}$ alkoxy, methylenedioxy, amino, nitro or hydroxy substituted phenyl-$C_{1-4}$ alkyl, $R^4$ is $C_{1-16}$ alkyl substituted by oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiadinyl, oxathianyl, perhydrodiazepinyl, oxathiepanyl, dioxepanyl, dithiepanyl, perhydroxazepinyl, perhydrothiazepinyl, perhydroxazocinyl, perhydrothiazocinyl, oxathiocanyl, perhydro-diazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydro-benzo[b]thienyl, 1,3-dihydrobenzo[c]thienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiazinyl, 2,3-dihydro-1,4-benzoxathienyl, 3,4-dihydro-2H-1,5-benzodioxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydro-isoquinolyl, perhydro-1-thianaphthyl or perhydro-2-thianaphthyl, each of said groups being unsubstituted or substituted by $C_{1-4}$ alkyl, phenyl, naphthyl, phenyl-$C_{1-4}$ alkyl, oxo, $C_{1-5}$ alkanoyl, benzoyl, phenyl-$C_{1-4}$ alkoxycarbonyl or $C_{1-4}$ alkoxycarbonyl, Y is carboxyl, $C_{1-4}$ alkoxycarbonyl, phenyl-$C_{1-4}$ alkoxycarbonyl or carboxyl amidated by an α-amino acid whose carboxyl group may be substituted by $C_{1-4}$ alkyl or phenyl-$C_{1-4}$ alkyl, the α-amino acid being glycine, valine, leucine, isoleucine, threonine, $N^\alpha$-lysine, methionine, phenylalanine or tryptophan, and the group $C_mH_{2m}$ represents methylene, ethylene or ethylidene, or a pharmaceutically acceptable salt thereof.

2. A compound according to claim 1, wherein $R^4$ is $C_{2-9}$ alkyl substituted by oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiadinyl, oxathianyl, perhydrodiazepinyl, oxathiepanyl, dioxepanyl, dithiepanyl, perhydroxazepinyl, perhydrothiazepinyl, perhydroxazocinyl, perhydrothiazocinyl, oxathiocanyl, perhydro-diazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydro-benzo[b]thienyl, 1,3-dihydrobenzo[c]thienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiazinyl, 2,3-dihydro-1,4-benzoxathienyl, 3,4-dihydro-2H-1,5-benzodioxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2 H-1,5-benzodithiepinyl, 2,3-dihydro-5H-1,4-benzodithiepinyl, perhydroindolyl, perhydroisoindolyl, perhydroquinolyl, perhydro-isoquinolyl, perhydro-1-thianaphthyl or perhydro-2-thianaphthyl, each of said groups being substituted or substituted by $C_{1-4}$ alkyl, phenyl, naphthyl, phenyl-$C_{1-4}$ alkyl, oxo, $C_{1-5}$ alkanoyl, benzoyl, phenyl-$C_{1-4}$ alkoxycarbonyl or $C_{1-4}$ alkoxycarbonyl.

3. A compound according to claim 1, wherein $R^4$ is $C_{2-6}$ alkyl substituted by oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiadinyl, oxathianyl, perhydrodiazepinyl, oxathiepanyl, dioxepanyl, dithiepanyl, perhydroxazepinyl, perhydrothiazepinyl, perhydroxazocinyl, perhydrothiazocinyl, oxathiocanyl, perhydro-diazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydro-benzo[b]thienyl, 1,3-dihydrobenzo[c]thienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2-(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3,-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiazinyl, 2,3-dihydro-1,4-benzoxathienyl, 3,4-dihydro-2H-1,5-benzodioxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydro-isoquinolyl, perhydro-1-thianaphthyl or perhydro-2-thianaphthyl, each of said groups being unsubstituted or substituted by $C_{1-4}$ alkyl, phenyl, naphthyl, phenyl-$C_{1-4}$ alkyl, oxo, $C_{1-5}$ alkanoyl, benzoyl, phenyl-$C_{1-4}$ alkoxycarbonyl or $C_{1-4}$ alkoxycarbonyl.

4. A compound according to claim 1, wherein $R^4$ is $C_{2-9}$ alkyl substituted by oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiadinyl, oxathianyl, perhydrodiazepinyl, oxathiepanyl, dioxepanyl, dithiepanyl, perhydroxazepinyl, perhydrothiazepinyl, perhydroxazocinyl, perhydrothiazocinyl, oxathiocanyl, perhydro-diazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydro-benzo[b]thienyl, 1,3-dihydrobenzo[c]thienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiazinyl, 2,3-dihydro-1,4-benzoxathienyl, 3,4-dihydro-2H-1,5-benzodioxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydro-isoquinolyl, perhydro-1-thianaphthyl or perhydro-2-thianaphthyl.

5. A compound according to claim 1, wherein $R^4$ is $C_{2-6}$ alkyl substituted by oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiadinyl, oxathianyl, perhydrodiazepinyl, oxathiepanyl, dioxepanyl, dithiepanyl, perhydroxazepinyl, perhydrothiazepinyl, perhydroxazocinyl, perhydrothiazocinyl, oxathiocanyl, perhydro-diazocinyl, dithiocanyl, dixocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydro-benzo[b]thienyl, 1,3-dihydro-benzo[c]thienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiazinyl, 2,3-dihydro-1,4-benzoxathienyl, 3,4-dihydro-2H-1,5-benzodioxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodi-
thiepinyl, 2,3-dihydro-5H-1,4-benzodithiepinyl, perhydroindolyl, perhydroisoindolyl, perhydroquinolyl, perhydro-isoquinolyl, perhydro-1-thianaphthyl or perhydro-2-thianaphthyl.

6. A compound according to claim 1, wherein $R^4$ is $C_{1-16}$ alkyl substituted by oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl or perhydroazocinyl, each of said groups being unsubstituted or substituted by $C_{1-4}$ alkyl, phenyl, naphthyl, phenyl-$C_{1-4}$ alkyl, oxo, $C_{1-5}$ alkanoyl, benzoyl, phenyl-$C_{1-4}$ alkoxycarbonyl or $C_{1-4}$ alkoxycarbonyl.

7. A compound according to claim 1, wherein $R^1$ and $R^2$ are hydrogen.

8. A compound according to claim 1, wherein $R^3$ is hydrogen, $C_{1-6}$ alkyl or phenyl-$C_{1-4}$ alkyl.

9. A compound according to claim 1, wherein $R^4$ is $C_{2-9}$ alkyl substituted by piperidyl, oxanyl or thianyl.

10. A compound according to claim 1, wherein $R^4$ is $C_{2-9}$ alkyl substituted by piperidyl.

11. A compound according to claim 1, wherein $R^4$ is $C_{2-9}$ alkyl substituted by 4-piperidyl.

12. A compound according to claim 1, wherein $R^4$ is (4-piperidyl)butyl.

13. A compound according to claim 1, wherein Y is carboxyl.

14. A compound according to claim 1, wherein the group $C_mH_{2m}$ is methylene.

15. The compound according to claim 1, which is 3(S)-[1(S)-carboxy-6-(4-piperidyl)hexyl]amino-4-oxo-2,3,4,5-tetrahydro-1,5-benzoxazepine-5-acetic acid.

16. The compound according to claim 1, which is 3(S)-[1(S)-ethoxycarbonyl-5-(4-piperidyl)pentyl]amino-4-oxo-2,3,4,5-tetrahydro-1,5-benzoxazepine-5-acetic acid.

17. The compound according to claim 1, which is 3(S)-[1(S)-carboxy-5-(4-piperidyl)pentyl]amino-4-oxo-2,3,4,5-tetrahydro-1,5-benzoxazepine-5-acetic acid.

18. An antihypertensive pharmaceutical composition containing an antihypertensive amount of a compound of the formula

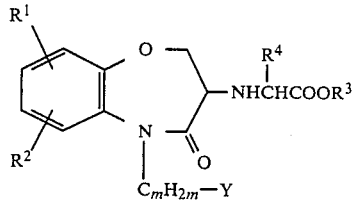

wherein $R^1$ and $R^2$ are independently hydrogen, halogen, trifluoromethyl, $C_{1-4}$ alkyl or $C_{1-4}$ alkoxy, or both jointly form tri- or tetramethylene, $R^3$ is hydrogen; optionally carboxy, $C_{1-4}$ alkoxycarbonyl, phenoxycarbonyl or phenyl-$C_{1-4}$ alkoxycarbonyl substituted $C_{1-6}$ alkyl; or optionally halogen, $C_{1-4}$ alkyl, $C_{1-4}$ alkoxy, methylenedioxy, amino, nitro or hydroxy substituted phenyl-$C_{1-4}$ alkyl, $R^4$ is $C_{1-16}$ alkyl substituted by oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiadinyl, oxathianyl, perhydrodiazepinyl, oxathiepanyl, dioxepanyl, dithiepanyl, perhydroxazepinyl, perhydrothiazepinyl, perhydroxazocinyl, perhydrothiazocinyl, oxathiocanyl, perhydro-diazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydro-benzo[b]thienyl, 1,3-dihydrobenzo[c]thienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3,-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiazinyl, 2,3-dihydro-1,4-benzoxathienyl, 3,4-dihydro-2H-1,5-benzodioxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydro-isoquinolyl, perhydro-1-thianaphthyl or perhydro-2-thianaphthyl, each of said groups being unsubstituted or substituted by $C_{1-4}$ alkyl, phenyl, naphthyl, phenyl-$C_{1-4}$ alkyl, oxo, $C_{1-5}$ alkanoyl, benzoyl, phenyl-$C_{1-4}$ alkoxycarbonyl or $C_{1-4}$ alkoxycarbonyl, Y is carboxyl, $C_{1-4}$ alkoxycarbonyl, phenyl-$C_{1-4}$ alkoxycarbonyl or carboxyl amidated by an α-amino acid whose carboxyl group may be substituted by $C_{1-4}$ alkyl or phenyl-$C_{1-4}$ alkyl, the α-amino acid being glycine, valine, leucine, isoleucine, threonine, $N^α$-lysine, methionine, phenylalanine or tryptophan, and the group $C_mH_{2m}$ represents methylene, ethylene or ethylidene, or a pharmaceutically acceptable salt thereof and a pharmaceutically acceptable carrier, excipient or diluent therefor.

19. Method for treatment of hypertension which comprises administration of an effective antihypertensive amount of a compound

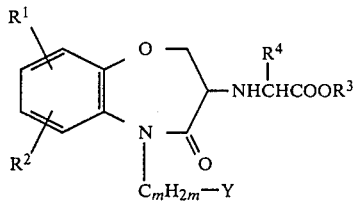

wherein $R^1$ and $R^2$ are independently hydrogen, halogen, trifluoromethyl, $C_{1-4}$ alkyl or $C_{1-4}$ alkoxy, or both jointly form tri- or tetramethylene, $R^3$ is hydrogen; optionally carboxy, $C_{1-4}$ alkoxycarbonyl, phenoxycarbonyl or phenyl-$C_{1-4}$ alkoxycarbonyl substituted $C_{1-6}$ alkyl; or optionally halogen, $C_{1-4}$ alkyl, $C_{1-4}$ alkoxy, methylenedioxy, amino, nitro or hydroxy substituted phenyl-$C_{1-4}$ alkyl, $R^4$ is $C_{1-16}$ alkyl substituted by oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiadinyl, oxathianyl, perhydrodiazepinyl, oxathiepanyl, dioxepanyl, dithiepanyl, perhydroxazepinyl, perhydrothiazepinyl, perhydroxazocinyl, perhydrothiazocinyl, oxathiocanyl, perhydro-diazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydro-benzo[b]thienyl, 1,3-dihydrobenzo[c]thienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiazinyl, 2,3-dihydro-1,4-benzoxathienyl, 3,4-dihydro-2H-1,5-benzodioxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydro-isoquinolyl, perhydro-1-thianaphthyl or perhydro-2-thianaphthyl, each of said groups being unsubstituted or substituted by $C_{1-4}$ alkyl, phenyl, naphthyl, phenyl-$C_{1-4}$ alkyl, oxo, $C_{1-5}$ alkanoyl, benzoyl, phenyl-$C_{1-4}$ alkoxycarbonyl or $C_{1-4}$ alkoxycarbonyl, Y is carboxyl, $C_{1-4}$ alkoxycarbonyl, phenyl-$C_{1-4}$ alkoxycarbonyl or carboxyl amidated by an α-amino acid whose carboxyl group may be substituted by $C_{1-4}$ alkyl or phenyl-$C_{1-4}$ alkyl, the α-amino acid being glycine, valine, leucine, isoleucine, threonine, $N^α$-lysine, methionine, phenylalanine or tryptophan, and the group $C_mH_{2m}$ represents methylene, ethylene or ethylidene, or a pharmaceutically acceptable salt thereof.

* * * * *